(12) United States Patent
Oh et al.

(10) Patent No.: US 11,491,181 B2
(45) Date of Patent: Nov. 8, 2022

(54) GLYCOLIPID COMPOSITIONS AND METHODS OF USE

(71) Applicant: President and Fellows of Harvard College, Cambridge, MA (US)

(72) Inventors: Sungwhan Oh, Cambridge, MA (US); Deniz Erturk-Hasdemir, Cambridge, MA (US); Dennis L. Kasper, Cambridge, MA (US); Kailyn L. Stefan, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 44 days.

(21) Appl. No.: 16/317,794

(22) PCT Filed: Jul. 15, 2017

(86) PCT No.: PCT/US2017/042282
§ 371 (c)(1),
(2) Date: Jan. 14, 2019

(87) PCT Pub. No.: WO2018/014012
PCT Pub. Date: Jan. 18, 2018

(65) Prior Publication Data
US 2019/0290680 A1    Sep. 26, 2019

Related U.S. Application Data

(60) Provisional application No. 62/362,630, filed on Jul. 15, 2016.

(51) Int. Cl.
| | |
|---|---|
| A61K 31/739 | (2006.01) |
| A61K 9/00 | (2006.01) |
| A61K 39/00 | (2006.01) |
| A61K 39/39 | (2006.01) |
| A61K 45/06 | (2006.01) |
| A61K 9/107 | (2006.01) |
| C07H 13/06 | (2006.01) |
| A61P 37/04 | (2006.01) |
| A61K 31/7024 | (2006.01) |

(52) U.S. Cl.
CPC .......... *A61K 31/739* (2013.01); *A61K 9/0019* (2013.01); *A61K 9/0053* (2013.01); *A61K 9/1075* (2013.01); *A61K 31/7024* (2013.01); *A61K 39/0008* (2013.01); *A61K 39/39* (2013.01); *A61K 45/06* (2013.01); *A61P 37/04* (2018.01); *C07H 13/06* (2013.01); *A61K 2039/52* (2013.01)

(58) Field of Classification Search
CPC ............... A61K 31/739; A61K 9/0019; A61K 39/0008; A61K 39/39; A61K 45/06; A61K 2039/52
USPC .......................................................... 514/54
See application file for complete search history.

(56) References Cited

U.S. PATENT DOCUMENTS

| | | |
|---|---|---|
| 3,723,506 A | 3/1973 | Deslongchamps |
| 3,849,550 A | 11/1974 | Teitelbaum et al. |
| 4,316,982 A | 2/1982 | Holst |
| 4,356,170 A | 10/1982 | Jennings et al. |
| 4,619,995 A | 10/1986 | Hayes |
| 4,740,480 A | 4/1988 | Ooka |
| 4,775,626 A | 10/1988 | Armenta et al. |
| 4,782,067 A | 11/1988 | Blythin et al. |
| 4,819,617 A | 4/1989 | Goldberg |
| 4,835,252 A | 5/1989 | Kaiser et al. |
| 4,886,787 A | 12/1989 | de Belder et al. |
| 4,937,270 A | 6/1990 | Hamilton et al. |
| 4,952,524 A | 8/1990 | Lee et al. |
| 5,126,141 A | 6/1992 | Henry |
| 5,130,417 A | 7/1992 | Stanley et al. |
| 5,140,016 A | 8/1992 | Goldberg et al. |
| 5,158,939 A | 10/1992 | Takayama et al. |
| 5,196,510 A | 3/1993 | Rodwell et al. |
| 5,215,896 A | 6/1993 | Keck et al. |
| 5,229,315 A | 7/1993 | Jun et al. |
| 5,331,573 A | 7/1994 | Balaji et al. |
| 5,468,676 A | 11/1995 | Madan |
| 5,514,581 A | 5/1996 | Ferrari et al. |
| 5,532,221 A | 7/1996 | Huang et al. |
| 5,565,204 A | 10/1996 | Kuo et al. |
| 5,576,002 A | 11/1996 | Jennings et al. |
| 5,576,241 A | 11/1996 | Sakai |
| 5,605,938 A | 2/1997 | Roufa et al. |
| 5,679,654 A | 10/1997 | Tzianabos et al. |
| 5,679,658 A | 10/1997 | Elson |
| 5,700,787 A | 12/1997 | Tzianabos et al. |
| 5,700,906 A | 12/1997 | Arnot et al. |
| 5,705,178 A | 1/1998 | Roufa et al. |

(Continued)

FOREIGN PATENT DOCUMENTS

| | | |
|---|---|---|
| CN | 1818061 A | 8/2006 |
| DE | 3704389 A1 | 8/1988 |

(Continued)

OTHER PUBLICATIONS

Fukuoka et al. (Eur. J. Biochem. 250, 55-62 (1997)).*

(Continued)

*Primary Examiner* — Shaojia A Jiang
*Assistant Examiner* — Michael C Henry
(74) *Attorney, Agent, or Firm* — Wolf, Greenfield & Sacks, P.C.

(57) ABSTRACT

The invention provides immunostimulatory glycolipids and compositions thereof and methods of use thereof.

19 Claims, 13 Drawing Sheets

(56) References Cited

U.S. PATENT DOCUMENTS

| | | |
|---|---|---|
| 5,760,200 A | 6/1998 | Miller et al. |
| 5,851,808 A | 12/1998 | Elledge et al. |
| 5,853,718 A | 12/1998 | Molin et al. |
| 5,868,870 A | 2/1999 | Fazan et al. |
| 5,888,741 A | 3/1999 | Hendry |
| 5,929,049 A | 7/1999 | Singh et al. |
| 5,936,076 A | 10/1999 | Higa et al. |
| 5,993,825 A | 11/1999 | Jennings et al. |
| 6,027,733 A | 2/2000 | Wang et al. |
| 6,110,672 A | 8/2000 | Mandel et al. |
| 6,150,459 A | 11/2000 | Mayes et al. |
| 6,274,144 B1 | 8/2001 | Wang et al. |
| 6,294,518 B1 | 9/2001 | Potter et al. |
| 6,358,939 B1 | 3/2002 | Hayes et al. |
| 6,447,765 B1 | 9/2002 | Horwitz |
| 6,670,146 B2 | 12/2003 | Barrat et al. |
| 6,749,831 B1 | 6/2004 | Bennett-Guerrero et al. |
| 6,995,237 B1 | 2/2006 | Zimmerman |
| 7,026,285 B2 | 4/2006 | Tzianabos et al. |
| 7,083,777 B1 | 8/2006 | Tzianabos et al. |
| 7,163,683 B2 | 1/2007 | Barstad et al. |
| 7,166,455 B2 | 1/2007 | Comstock et al. |
| 7,384,645 B2 | 6/2008 | Foster et al. |
| 7,629,330 B2 | 12/2009 | Wang et al. |
| 7,678,558 B2 | 3/2010 | Comstock et al. |
| 7,803,602 B2 | 9/2010 | Comstock et al. |
| 7,807,154 B2 | 10/2010 | Strasburger et al. |
| 8,008,276 B2 | 8/2011 | Wang et al. |
| 8,206,726 B2 | 6/2012 | Kasper et al. |
| 8,580,278 B2 | 11/2013 | Kasper et al. |
| 8,586,029 B2 | 11/2013 | Kasper et al. |
| 9,057,070 B2 | 6/2015 | Mazmanian et al. |
| 9,265,790 B2 | 2/2016 | Tzianabos et al. |
| 9,539,281 B2 | 1/2017 | Kasper et al. |
| 2001/0001788 A1 | 5/2001 | Satoh et al. |
| 2002/0022019 A1 | 2/2002 | Laulund |
| 2002/0090357 A1 | 7/2002 | Barrat et al. |
| 2002/0155436 A1 | 10/2002 | Classen |
| 2003/0044425 A1 | 3/2003 | Burt et al. |
| 2003/0059462 A1 | 3/2003 | Barenholz et al. |
| 2003/0147865 A1 | 8/2003 | Salomon et al. |
| 2003/0219413 A1 | 11/2003 | Comstock et al. |
| 2004/0185057 A1 | 1/2004 | Kirkby et al. |
| 2004/0039056 A1 | 2/2004 | Bollag et al. |
| 2004/0092433 A1 | 5/2004 | Wang et al. |
| 2004/0219160 A1 | 11/2004 | Tzianabos et al. |
| 2005/0020515 A1 | 1/2005 | Graff et al. |
| 2005/0063979 A1 | 3/2005 | Pickl et al. |
| 2005/0101012 A1 | 5/2005 | Schuler et al. |
| 2005/0119164 A1 | 6/2005 | Taylor et al. |
| 2005/0147624 A1 | 7/2005 | Jennings et al. |
| 2005/0181021 A1 | 8/2005 | Lamb |
| 2005/0271643 A1 | 12/2005 | Sorokulova et al. |
| 2006/0014717 A1 | 1/2006 | Angstrom et al. |
| 2006/0110412 A1 | 5/2006 | Desmons et al. |
| 2006/0116332 A1 | 6/2006 | Strober et al. |
| 2006/0153832 A1 | 7/2006 | Tzianabos et al. |
| 2006/0257852 A1 | 11/2006 | Rappuoli et al. |
| 2006/0275752 A1 | 12/2006 | Sindhi |
| 2007/0020730 A1 | 1/2007 | Comstock et al. |
| 2007/0154991 A1 | 7/2007 | Comstock et al. |
| 2007/0207526 A1 | 9/2007 | Coit et al. |
| 2007/0238747 A1 | 10/2007 | van Duzer et al. |
| 2008/0057565 A1 | 3/2008 | Comstock et al. |
| 2008/0131445 A1 | 6/2008 | Bluestone et al. |
| 2008/0286252 A1 | 11/2008 | Sinnott |
| 2009/0017472 A1 | 1/2009 | Stuhlmuller et al. |
| 2009/0124573 A1 | 5/2009 | Mazmanian et al. |
| 2009/0252708 A1 | 10/2009 | Fitzpatrick et al. |
| 2009/0317410 A1 | 12/2009 | Wang et al. |
| 2009/0317427 A1 | 12/2009 | Kasper et al. |
| 2010/0080760 A1 | 4/2010 | Hyde et al. |
| 2010/0112002 A1 | 5/2010 | Lien et al. |
| 2010/0221269 A1 | 9/2010 | Boons et al. |
| 2010/0221315 A1 | 9/2010 | Constantino et al. |
| 2010/0221755 A1 | 9/2010 | Lee et al. |
| 2010/0275282 A1 | 10/2010 | Round et al. |
| 2010/0311686 A1 | 12/2010 | Kasper et al. |
| 2010/0330067 A1 | 12/2010 | O'Neill et al. |
| 2010/0330166 A1 | 12/2010 | Ishida et al. |
| 2011/0002965 A1 | 1/2011 | Round et al. |
| 2011/0009360 A1 | 1/2011 | Kasper et al. |
| 2011/0059125 A1 | 3/2011 | Tzianabos et al. |
| 2011/0086011 A1 | 4/2011 | Kasper et al. |
| 2011/0150852 A1 | 6/2011 | Chambaud et al. |
| 2011/0229513 A1* | 9/2011 | Cox .................. A61P 31/04 424/197.11 |
| 2011/0251156 A1 | 10/2011 | Shen et al. |
| 2011/0287048 A1 | 11/2011 | Round et al. |
| 2012/0087895 A1 | 4/2012 | Mazmanian et al. |
| 2012/0094950 A1 | 4/2012 | Kasper et al. |
| 2012/0309955 A1 | 12/2012 | Kasper et al. |
| 2012/0315264 A1 | 12/2012 | Tzianabos et al. |
| 2013/0039949 A1 | 2/2013 | Mazmanian et al. |
| 2013/0058997 A1 | 3/2013 | Reed et al. |
| 2013/0064859 A1 | 3/2013 | Mazmanian et al. |
| 2013/0121966 A1 | 5/2013 | Mazmanian et al. |
| 2013/0195802 A1 | 8/2013 | Moore |
| 2014/0030807 A1 | 1/2014 | Kasper et al. |
| 2014/0072534 A1 | 3/2014 | Mazmanian et al. |
| 2014/0099331 A1 | 4/2014 | Tzianabos et al. |
| 2014/0243285 A1 | 8/2014 | Kasper et al. |
| 2014/0335131 A1 | 11/2014 | Mazmanian et al. |
| 2016/0022727 A1 | 1/2016 | Round et al. |
| 2016/0030464 A1 | 2/2016 | Mazmanian et al. |
| 2019/0211334 A1 | 7/2019 | Lizasoain Hernandez et al. |
| 2019/0046560 A1 | 9/2019 | Oh et al. |
| 2019/0367959 A1 | 12/2019 | Ernst et al. |
| 2021/0315923 A1 | 10/2021 | Sungwhan et al. |

FOREIGN PATENT DOCUMENTS

| | | |
|---|---|---|
| EP | 0382576 A1 | 8/1990 |
| EP | 0497524 A2 | 8/1992 |
| EP | 1358885 A1 | 11/2003 |
| EP | 1459757 A1 | 9/2004 |
| EP | 0371414 A2 | 6/2006 |
| GB | 2286193 A | 8/1995 |
| JP | 56128721 | 10/1981 |
| JP | H10-507746 | 7/1998 |
| JP | 2002541113 | 12/2002 |
| JP | 2004536028 | 12/2004 |
| JP | 2006522135 | 9/2006 |
| JP | 2012-524910 A | 10/2012 |
| JP | 2014-520932 A | 8/2014 |
| WO | WO 84/04526 A1 | 11/1984 |
| WO | WO 95/31990 A1 | 11/1995 |
| WO | WO 96/07427 A1 | 3/1996 |
| WO | WO 96/32119 A1 | 10/1996 |
| WO | WO 96/35433 A1 | 11/1996 |
| WO | WO 98/42718 A1 | 10/1998 |
| WO | WO 98/45335 A1 | 10/1998 |
| WO | WO 00/01733 A1 | 1/2000 |
| WO | WO 00/59515 A2 | 10/2000 |
| WO | WO 02/07741 A1 | 1/2002 |
| WO | WO 02/045708 A2 | 6/2002 |
| WO | WO 03/075953 A2 | 9/2003 |
| WO | WO 2003/077863 A2 | 9/2003 |
| WO | WO 03/095606 A2 | 11/2003 |
| WO | WO 04/050909 A2 | 6/2004 |
| WO | WO 2004/089407 A2 | 10/2004 |
| WO | WO 2005/010215 A2 | 2/2005 |
| WO | WO 2007/040446 A1 | 4/2007 |
| WO | WO 2007/092451 A2 | 8/2007 |
| WO | WO 2008/095141 A2 | 8/2008 |
| WO | WO 2009/062132 A2 | 5/2009 |
| WO | WO 2009/149149 A1 | 12/2009 |
| WO | WO 2010/124256 A2 | 10/2010 |
| WO | WO 2011/056703 A1 | 5/2011 |
| WO | WO 2011/127302 A2 | 10/2011 |
| WO | WO 2011/146910 A1 | 11/2011 |
| WO | WO 2011/153226 A2 | 12/2011 |
| WO | WO 2012/027032 A1 | 3/2012 |
| WO | WO 2012/103532 A1 | 8/2012 |

(56) References Cited

FOREIGN PATENT DOCUMENTS

| WO | WO 2013/009945 A1 | 1/2013 |
|---|---|---|
| WO | WO 2013/019896 A1 | 2/2013 |
| WO | WO 2013/036290 A1 | 3/2013 |
| WO | WO 2013/052099 A2 | 4/2013 |
| WO | WO 2014/182966 A1 | 11/2014 |
| WO | WO 2015/147899 A1 | 10/2015 |
| WO | WO 2017/031431 A1 | 2/2017 |

OTHER PUBLICATIONS

Extended European Search Report for Application No. 17828599.5, dated Feb. 19, 2020.
International Search Report and Written Opinion for Application No. PCT/US2017/042282, dated Oct. 2, 2017.
International Preliminary Report on Patentability for Application No. PCT/US2017/042282, dated Jan. 24, 2019.
GenBank Accession No. AJ277832; Hutloff Jan. 19, 2001.
GenBank Accession No. CAC06612; Hutloff Jan. 19, 2001.
GenBank Accession No. NM_012092; Dec. 20, 2003.
GenBank Accession No. NP_036224 Dec. 20, 2003.
[No Author Listed] Excerpts from Immunobiology, $7^{th}$ ed. 2008. Part IV: The Adaptive Immune Response. Chapter 9 T Cell-Mediated Immunity.
[No Author Listed] Acute Respiratory Disease Syndrome: What is acute respiratory disease syndrome? American Lung Association. 3 pages. http://www.lungusa.org/site/apps/nlnet/content3.aspx?c=dvLUK9O0E&b=2058817&content. Sep. 24, 2008.
[No Author Listed] Lupus study. Meet A Lupus Researcher. www.lupusstudy.org/updates.php. Nov. 2005; 1-2.
[No Author Listed] Polyethylene Glycols (PEGs). Accessed Mar. 7, 2005. 1 page. http://www.mindfully.org/Plastic/Polymers/Polyethylene-Glycols-PEGs.htm.
[No Author Listed] The Merck Index . Eleventh Edition 1989:734-735.
[No Author Listed] VAXA, Systemic lupus erythematosus (SLE), damaging and unpredictable. http://www.vaxa.com/arthritis-systemic-lupus-erythematosus.cfm. 1 page. Accessed Apr. 3, 2008.
[No Author Listed] "Asthma" from the Centers for Disease Control and Prevention. Retrieved Nov. 13, 2012. www.cdc.gov/asthma/aag/2010/overview.html, pp. 1-2.
[No Author Listed] Drug Absorption, Bioavailability, and Routes of Administration. Goodman & Gilman's The Pharmacological Basis of Therapeutics, Tenth Edition, McGraw-Hill Medical Publishing Edition, New York, 2001, pp. 5-8.
[No Author Listed] MS the Disease. National Multiple Sclerosis Society. http://www.nationalmssociety.org/. 4 pages.
[No Author Listed] National Public Health Partnership, The Language of Prevention. Melbourne: NPHP. 2006. 9 pages.
[No Author Listed] Progress in Autoimmune Diseases Research. National Institutes of Health. The Autoimmune Diseases Coordinating Committee. Report to Congress. U.S. Department of Health and Human Service. Mar. 2005. 146 pages.
[No Author Listed] NCBI Sequence View "Toxin" [*Salmonella typhimurium* LT2]. http://www.ncbi.nim.nih.gov/entrez/viewer.fcgi?db=protein&id=17233414, pp. 1-2.
Abreu et al., Measurement of vitamin D levels in inflammatory bowel disease patients reveals a subset of Crohn's disease patients with elevated 1,25-dihydroxyvitamin D and low bone mineral density. Gut. Aug. 2004;53(8):1129-36.
Abt et al., Commensal bacteria calibrate the activation threshold of innate antiviral immunity. Immunity. Jul. 27, 2012;37(1):158-70. doi: 10.1016/j.immuni.2012.04.011. Epub Jun. 14, 2012.
Adams et al., Extrarenal expression of the 25-hydroxyvitamin D-1-hydroxylase. Arch Biochem Biophys. Jul. 1, 2012;523(1):95-102. doi: 10.1016/j.abb.2012.02.016. Epub Mar. 14, 2012.
Adams et al., Unexpected actions of vitamin D: new perspectives on the regulation of innate and adaptive immunity. Nat Clin Pract Endocrinol Metab. Feb. 2008;4(2):80-90. doi: 10.1038/ncpendmet0716.
Adkins, T-cell function in newborn mice and humans. Immunol Today. Jul. 1999;20(7):330-5.
Adkins, Development of neonatal Th1/Th2 function. Int Rev Immunol. 2000;19(2-3):157-71.
Adkins et al., Early block in maturation is associated with thymic involution in mammary tumor-bearing mice. J Immunol. Jun. 1, 2000;164(11):5635-40.
Adkins et al., Exclusive Th2 primary effector function in spleens but mixed Th1/Th2 function in lymph nodes of murine neonates. J Immunol. Mar. 1, 2000;164(5):2347-53.
Afzali, The role of T helper 17 (Th17) and regulatory T cells (Treg) in human organ transplantation and autoimmune disease. Clin Exp Immunol. Apr. 2007;148(1):32-46.
Aharoni et al., Copolymer 1 induces T cells of the T helper type 2 that crossreact with myelin basic protein and suppress experimental autoimmune encephalomyelitis. Proc Natl Acad Sci U S A. Sep. 30, 1997;94(20):10821-6.
Aharoni et al., Bystander suppression of experimental autoimmune encephalomyelitis by T cell lines and clones of the Th2 type induced by copolymer 1. J Neuroimmunol. Nov. 2, 1998;91(1-2):135-46.
Aharoni et al., Studies on the mechanism and specificity of the effect of the synthetic random copolymer GLAT on graft-versus-host disease. Immunol Lett. Jul. 1997;58(2):79-87.
Akbari et al., Antigen-specific regulatory T cells develop via the ICOS-ICOS-ligand pathway and inhibit allergen-induced airway hyperreactivity. Nat Med. Sep. 2002;8(9):1024-32. Epub Jul. 29, 2002.
Al-Bader et al., Activation of human dendritic cells is modulated by components of the outer membranes of Neisseria meningitidis. Infect Immun. Oct. 2003;71(10):5590-7.
Allen et al., A pilot study of the immunological effects of high-dose vitamin D in healthy volunteers. Mult Scler. Dec. 2012;18(12):1797-800. doi: 10.1177/1352458512442992. Epub Mar. 28, 2012.
Amsen et al., Instruction of distinct CD4 T helper cell fates by different notch ligands on antigen-presenting cells. Cell. May 14, 2004;117(4):515-26.
Anderson et al., A transgenic model of central nervous system autoimmunity mediated by CD4+ and CD8+ T and B cells. J Immunol. Mar. 1, 2012;188(5):2084-92. doi: 10.4049/jimmunol.1102186. Epub Jan. 25, 2012.
Arnon et al., New insights into the mechanism of action of copolymer 1 in experimental allergic encephalomyelitis and multiple sclerosis. J Neurol. Apr. 1996;243(4 Suppl 1):S8-13. Review.
Asadullah et al., Interleukin-10 therapy—review of a new approach. Pharmacol Rev. Jun. 2003;55(2):241-69.
Ascherio et al., Vitamin D and multiple sclerosis. Lancet Neurol. Jun. 2010;9(6):599-612. doi: 10.1016/S1474-4422(10)70086-7.
Asseman et al., An essential role for interleukin 10 in the function of regulatory T cells that inhibit intestinal inflammation. J Exp Med. Oct. 4, 1999;190(7):995-1004.
Atarashi et al., ATP drives lamina propria T(H)17 cell differentiation. Nature. Oct. 9, 2008;455(7214):808-12. doi: 10.1038/nature07240. Epub Aug. 20, 2008.
Awasthi et al., Interplay between effector Th17 and regulatory T cells. J Clin Immunol. Nov. 2008;28(6):660-70. doi: 10.1007/s10875-008-9239-7. Epub Sep. 23, 2008.
Azzawi et al., Identification of activated T lymphocytes and eosinophils in bronchial biopsies in stable atopic asthma. Am Rev Respir Dis. Dec. 1990;142(6 Pt 1):1407-13.
Bach, The effect of infections on susceptibility to autoimmune and allergic diseases. N Engl J Med. Sep. 19, 2002;347(12):911-20.
Baecher-Allan et al., CD2 costimulation reveals defective activity by human CD4+CD25(hi) regulatory cells in patients with multiple sclerosis. J Immunol. Mar. 15, 2011;186(6):3317-26. doi: 10.4049/jimmunol.1002502. Epub Feb. 7, 2011.
Banerjee et al., Expansion of FOXP3high regulatory T cells by human dendritic cells (DCs) in vitro and after injection of cytokine-matured DCs in myeloma patients. Blood. Oct. 15, 2006;108(8):2655-61. Epub Jun. 8, 2006.
Bar-On et al., Defining in vivo dendritic cell functions using CD11c-DTR transgenic mice. Methods Mol Biol. 2010;595:429-42. doi: 10.1007/978-1-60761-421-0_28.

(56) References Cited

OTHER PUBLICATIONS

Baranzjni et al., Genome, epigenome and RNA sequences of monozygotic twins discordant for multiple sclerosis. Nature. Apr. 29, 2010;464(7293):1351-6. doi: 10.1038/nature08990.

Barnes et al., How do Corticosteroids Work in Asthma? Ann. Intern. Med. 2003;139:359-70.

Barnes et al., Regulatory T cells reinforce intestinal homeostasis. Immunity. Sep. 18, 2009;31(3):401-11. doi: 10.1016/j.immuni.2009.08.011.

Barrat et al., In vitro generation of interleukin 10-producing regulatory CD4(+) T cells is induced by immunosuppressive drugs and inhibited by T helper type 1 (Th1)- and Th2-inducing cytokines. J Exp Med. Mar. 4, 2002;195(5):603-16.

Barutca et al., Prevention of interleukin-2-induced severe bronchospasm with salbutamol. J Aerosol Med. 2003 Summer;16(2):183-4.

Basu et al., Synthesis and characterization of a peptide nucleic acid conjugated to a D-peptide analog of insulin-like growth factor 1 for increased cellular uptake. Bioconjug Chem. Jul.-Aug. 1997;8(4):481-8.

Batta et al., Conformational stabilization of the altruronic acid residue in the O-specific polysaccharide of Shigella sonnei/Plesiomonas shigelloides. Carbohydr Res. Dec. 1997;305(1):93-9.

Baumann et al., Structural elucidation of two capsular polysaccharides from one strain of Bacteroides fragilis using high-resolution NMR spectroscopy. Biochemistry. Apr. 28, 1992;31(16):4081-9.

Bayley et al. Analysis of cepA and other Bacteroides fragilis genes reveals a unique promoter structure. (2000) FEMS Microbiol Lett 193:149-54.

Bazan et al., Unraveling the structure of IL-2. Science. Jul. 17, 1992;257(5068):410-3.

Becker et al., Clustering of non-major histocompatibility complex susceptibility candidate loci in human autoimmune diseases. Proc Natl Acad Sci U S A. Aug. 18, 1998;95(17):9979-84.

Becker et al., TGF-beta suppresses tumor progression in colon cancer by inhibition of IL-6 trans-signaling. Immunity. Oct. 2004;21(4):491-501.

Belkaid et al., Regulatory T cells in the control of host-microorganism interactions (*). Annu Rev Immunol. 2009;27:551-89. doi: 10.1146/annurev.immunol.021908.132723.

Bell, Function of CD4 T cell subsets in vivo: expression of CD45R isoforms. Semin Immunol. Feb. 1992;4(1):43-50.

Berer et al., Commensal gut flora and brain autoimmunity: a love or hate affair? Acta Neuropathol. May 2012;123(5):639-51. doi: 10.1007/s00401-012-0949-9. Epub Feb. 10, 2012.

Berer et al., Commensal microbiota and myelin autoantigen cooperate to trigger autoimmune demyelination. Nature. Oct. 26, 2011;479(7374):538-41. doi: 10.1038/nature10554.

Berggren et al., Decreasing serum concentrations of all-trans, 13-cis retinoic acids and retinol during fasting and caloric restriction. J Intern Med. Mar. 2003;253(3):375-80.

Bernatowska-Matuszktewicz et al., IgG subclasses and antibody response to pneumococcal capsular polysaccharides in children with severe sinopulmonary infections and sathma. Immunol Invest. 1991;20(2):173-185.

Bettelli et al., Myelin oligodendrocyte glycoprotein-specific T cell receptor transgenic mice develop spontaneous autoimmune optic neuritis. J Exp Med. May 5, 2003;197(9):1073-81.

Bettelli et al., Reciprocal developmental pathways for the generation of pathogenic effector TH17 and regulatory T cells. Nature. May 11, 2006;441(7090):235-8. Epub Apr. 30, 2006.

Bhaduri et al., Simple and rapid method for disruption of bacteria for protein studies. Appl Environ Microbiol. Oct. 1983;46(4):941-3.

Bhat et al., Innate and adaptive autoimmunity directed to the central nervous system. Neuron. Oct. 15, 2009;64(1):123-32. doi: 10.1016/j.neuron.2009.09.015.

Bilo et al., Diagnosis of Hymenoptera venom allergy; Allergy 2005; 60:1339-1349.

Blander et al., Toll-dependent selection of microbial antigens for presentation by dendritic cells. Nature. Apr. 6, 2006;440(7085):808-12. Epub Feb. 19, 2006.

Blomfield et al. Lrp stimulates phase variation of type 1 fimbriation in E. coli K12. J. Bacteriology 175, 27-36, 1993.

Blumberg et al., Microbiota, disease, and back to health: a metastable journey. Sci Transl Med. Jun. 6, 2012;4(137):137rv7. doi: 10.1126/scitranslmed.3004184.

Boes et al., Accelerated development of IgG autoantibodies and autoimmune disease in the absence of secreted IgM. Proc Natl Acad Sci U S A. Feb. 1, 2000;97(3):1184-9.

Boguniewicz, M.; The autoimmune nature of chronic urticaria; Allergy Asthma Proc 2008; 29:433-438.

Bollrath et al., gp130-mediated Stat3 activation in enterocytes regulates cell survival and cell-cycle progression during colitis-associated tumorigenesis. Cancer Cell. Feb. 3, 2009;15(2):91-102. doi: 10.1016/j.ccr.2009.01.002.

Borsellino et al., Expression of ectonucleotidase CD39 by Foxp3+ Treg cells: hydrolysis of extracellular ATP and immune suppression. Blood. Aug. 15, 2007;110(4):1225-32. Epub Apr. 20, 2007.

Bouma et al., The immunological and genetic basis of inflammatory bowel disease. Nat Rev Immunol. Jul. 2003;3(7):521-33.

Bouskra et al., Lymphoid tissue genesis induced by commensals through NOD1 regulates intestinal homeostasis. Nature. Nov. 27, 2008;456(7221):507-10. doi: 10.1038/nature07450. Epub Nov. 5, 2008.

Braun et al., Body traffic: ecology, genetics, and immunity in inflammatory bowel disease. Annu Rev Pathol. 2007;2:401-29.

Bregenholt, Cells and Cytokines in the Pathogenesis of Inflammatory Bowel Disease: New Insights from Mouse T Cell Transfer Models. Exp Clin Immunogenet. Jun. 2000;17(3):115-129.

Brichford, Can You Prevent Multiple Sclerosis? Understanding factors that increase your risk of multiple sclerosis and what—if anything—you can do about them. EverydayHealth.com. Dec. 2008; 2 pages.

Brubaker et al., Mitogenic activity of purified capsular polysaccharide A from Bacteroides fragilis: differential stimulatory effect on mouse and rat lymphocytes in vitro. J Immunol. Feb. 15, 1999;162(4):2235-42.

Bruce et al., Converging pathways lead to overproduction of IL-17 in the absence of vitamin D signaling. Int Immunol. Aug. 2011;23(8):519-28. doi: 10.1093/intimm/dxr045. Epub Jun. 22, 2011.

Brunkow et al., Disruption of a new forkhead/winged-helix protein, scurfin, results in the fatal lymphoproliferative disorder of the scurfy mouse. Nat Genet. Jan. 2001;27(1):68-73.

Budinger et al., Immunologic mechanisms in hypersensitivity reactions to metal ions: an overview. Allergy. Feb. 2000;55(2):108-15. Review.

Burgers et al., The challenges of HIV vaccine development and testing. Best Pract Res Clin Obstet Gynaecol. Apr. 2005;19(2):277-91.

Cabrera et al., Influence of serum and soluble CD25 (sCD25) on regulatory and effector T-cell function in hepatocellular carcinoma. Scand J Immunol. Oct. 2010;72(4):293-301. doi: 10.1111/j.1365-3083.2010.02427.x.

Cahill et al., Inflammatory bowel disease: an immunity-mediated condition triggered by bacterial infection with Helicobacter hepaticus. Infect Immun. Aug. 1997;65(8):3126-31.

Campbell et al., The vitamin D receptor as a therapeutic target. Expert Opin Ther Targets. Oct. 2006;10(5):735-48.

Cantorna et al., 1,25-Dihydroxycholecalciferol prevents and ameliorates symptoms of experimental murine inflammatory bowel disease. J Nutr. Nov. 2000; 130(11):2648-52.

Cantorna et al., Vitamin D status, 1,25-dihydroxyvitamin D3, and the immune system. Am J Clin Nutr. Dec. 2004;80(6 Suppl):1717S-20S.

Cantorna et al., 1,25-Dihydroxyvitamin D3 reversibly blocks the progression of relapsing encephalomyelitis, a model of multiple sclerosis. Proc Natl Acad Sci U S A. Jul. 23, 1996;93(15):7861-4.

Cash et al., Symbiotic bacteria direct expression of an intestinal bactericidal lectin. Science. Aug. 25, 2006;313(5790):1126-30.

(56) References Cited

OTHER PUBLICATIONS

Chambers et al., The impact of vitamin D on regulatory T cells. Curr Allergy Asthma Rep. Feb. 2011;11(1):29-36. doi: 10.1007/s11882-010-0161-8.
Chang et al., 1,25-Dihydroxyvitamin D3 inhibits the differentiation and migration of T(H)17 cells to protect against experimental autoimmune encephalomyelitis. PLoS One. Sep. 23, 2010;5(9):e12925. doi: 10.1371/journal.pone.0012925.
Chatila et al., Role of regulatory T cells in human diseases. J Allergy Clin Immunol. Nov. 2005;116(5):949-59; quiz 960.
Chen et al., Pertussis toxin by inducing IL-6 promotes the generation of IL-17-producing CD4 cells. J Immunol. May 15, 2007;178(10):6123-9.
Chen et al., Delivery of foreign antigens by engineered outer membrane vesicle vaccines. Proc Natl Acad Sci U S A. Feb. 16, 2010;107(7):3099-104. doi: 10.1073/pnas.0805532107. Epub Jan. 27, 2010.
Chen et al., DNA inversion on conjugative plasmid pVT745. J Bacteriol. Nov. 2002;184(21):5926-34.
Cho et al., Recent insights into the genetics of inflammatory bowel disease. Gastroenterology. May 2011;140(6):1704-12. doi: 10.1053/j.gastro.2011.02.046.
Chow et al., Getting the bugs out of the immune system: do bacterial microbiota "fix" intestinal T cell responses? Cell Host Microbe. Jan. 22, 2009;5(1):8-12. doi: 10.1016/j.chom.2008.12.006.
Clemente et al., Infliximab modifies mesenteric adipose tissue alterations and intestinal inflammation in rats with TNBS-induced colitis. Scand J Gastroenterol. Sep. 2012;47(8-9):943-50. doi: 10.3109/00365521.2012.688213. Epub May 28, 2012.
Cobb et al., Zwitterionic capsular polysaccharides: the new MHCII-dependent antigens. Cell Microbiol. Oct. 2005;7(10):1398-403. Review.
Collison et al., The inhibitory cytokine IL-35 contributes to regulatory T-cell function. Nature. Nov. 22, 2007;450(7169):566-9.
Comstock et al., Bacterial glycans: key mediators of diverse host immune responses. Cell. Sep. 8, 2006;126(5):847-50.
Comstock et al., Interstrain variation of the polysaccharide B biosynthesis locus of Bacteroides fragilis: characterization of the region from strain 638R. J Bacteriol. Oct. 1999;181(19):6192-6.
Comstock et al. Analysis of a capsular polysaccharide biosynthesis locus of Bacteroides fragilis. (1999) Infect Immun 67:3525-32.
Conesa et al., Interleukin-2 induces peroxide production by primed normodense eosinophils of patients with asthma. Allergy Asthma Proc. Jan.-Feb. 2003;24(1):27-33.
Coombes et al., A functionally specialized population of mucosal CD103+ DCs induces Foxp3+ regulatory T cells via a TGF-beta and retinoic acid-dependent mechanism. J Exp Med. Aug. 6, 2007;204(8):1757-64. Epub Jul. 9, 2007.
Coombes et al., Control of intestinal homeostasis by regulatory T cells and dendritic cells. Semin Immunol. Apr. 2007;19(2):116-26. Epub Feb. 21, 2007.
Coombes et al., Regulatory T cells and intestinal homeostasis. Immunol Rev. Apr. 2005;204:184-94.
Correale et al., Vitamin D-mediated immune regulation in multiple sclerosis. J Neurol Sci. Dec. 15, 2011;311(1-2):23-31. doi: 10.1016/j.jns.2011.06.027. Epub Jul. 2, 2011.
Couper et al., IL-10: the master regulator of immunity to infection. J Immunol. May 1, 2008;180(9):5771-7.
Coussens et al., Inflammation and cancer. Nature. Dec. 19-26, 2002;420(6917):860-7.
Coyne et al., Bacteroides fragilis NCTC9343 produces at least three distinct capsular polysaccharides: cloning, characterization, and reassignment of polysaccharide B and C biosynthesis loci. Infect Immun. Nov. 2000;68(11):6176-81.
Coyne et al. Polysaccharide biosynthesis locus required for virulence of Bacteroides fragilis. (2001) Infect Immun 69:4342-50.
Coyne et al., Mpi recombinase globally modulates the surface archtiecture of a human commensal bacterium. Proc Natl Acad Sci U S A. Sep. 2, 2003;100(18):10446-51. Epub Aug. 12, 2003.
Crabb et al., T cell regulation of Bacteroides fragilis-induced intraabdominal abscesses. Rev Infect Dis. Jan.-Feb. 1990;12 Suppl 2:S178-84. Review.
Craig, Autologous hematopoietic stem cell transplantation for Crohn's disease. Autoimmun Rev. Aug. 2002;1(4):244-9. Review.
Dadley-Moore, The sweet side of maturation. Nature Rev Immunol. Sep. 2005;5:674.
Dahiyat et al., De novo protein design: fully automated sequence selection .Science (1997) 278:82-87.
Daniel et al., Immune modulatory treatment of trinitrobenzene sulfonic acid colitis with calcitriol is associated with a change of a T helper (Th) 1/Th17 to a Th2 and regulatory T cell profile. J Pharmacol Exp Ther. Jan. 2008;324(1):23-33. Epub Oct. 2, 2007.
Deiß, Treating multiple sclerosis with monoclonal antibodies: a 2013 update. Expert Rev Neurother. Mar. 2013;13(3):313-35. doi: 10.1586/ern.13.17.
Denning et al., Lamina propria macrophages and dendritic cells differentially induce regulatory and interleukin 17-producing T cell responses. Nat Immunol. Oct. 2007;8(10):1086-94. Epub Sep. 16, 2007.
Deslongchamps et al., Ozonolysis of Acetals. (1) Ester Synthesis, (2) THP Ether Cleavage, (3) Selective Oxidation of β-Glycoside, (4) Oxidative Removal of Benzylidene and Ethylidene Protecting Groups. Canadian J of Chem. 1971;49:2465-2467.
Deslongchamps et al., The Importance of Conformation in the Ozonolysis of Acetals. Canadian J Chem. 1972;50:3402-3404.
Deslongchamps et al., The Oxidation of Acetals by Ozone. Canadian J Chem. 1974;52:3651-3664.
Dethlefsen et al., An ecological and evolutionary perspective on human-microbe mutualism and disease. Nature. Oct. 18, 2007;449(7164):811-8.
Dias et al., Antisense oligonucleotides: Basic concepts and mechanisms. Mol. Cancer Therap., 2002, vol. 1: 347-355.
Difabio et al., Structure of the Capsular Polysaccharide Antigen of Type IV Group B Streptococcus; Can. J. Chem. 67:877 (1989).
Doig et al., The efficacy of the heat killing of Mycobacterium tuberculosis. J Clin Pathol. Oct. 2002;55(10):778-9.
Dong, Diversification of T-helper-cell lineages: finding the family root of IL-17-producing cells. Nat Rev Immunol. Apr. 2006;6(4):329-33.
Dooms et al., Revisiting the role of IL-2 in autoimmunity. Eur J Immunol. Jun. 2010;40(6):1538-40. doi: 10.1002/eji.201040617.
Duerr et al., A genome-wide association study identifies IL23R as an inflammatory bowel disease gene. Science. Dec. 1, 2006;314(5804):1461-3. Epub Oct. 26, 2006.
Eisenstein et al. Integration host factor is required for the DNA inversion that controls phase variation in E. coli. Proc Natl. Acad. Sci. 84, 6506-6510, 1987. cited by other .
Elson, Commensal bacteria as targets in Crohn's disease. Gastroenterology. Jul. 2000;119(1):254-7.
Elson et al., Monoclonal anti-interleukin 23 reverses active colitis in a T cell-mediated model in mice. Gastroenterology. Jun. 2007;132(7):2359-70. Epub Apr. 13, 2007.
Falk et al., Creating and maintaining the gastrointestinal ecosystem: what we know and need to know from gnotobiology. Microbiol Mol Biol Rev. Dec. 1998;62(4):1157-70.
Feuerer et al., Foxp3+ regulatory T cells: differentiation, specification, subphenotypes. Nat Immunol. Jul. 2009;10(7):689-95. doi: 10.1038/ni.1760.
Finberg et al., Decay-accelerating factor expression on either effector or target cells inhibits cytotoxicity by human natural killer cells. J Immunol. Sep. 15, 1992;149(6):2055-60.
Fink et al., Human antigen-presenting cells respond differently to gut-derived probiotic bacteria but mediate similar strain-dependent NK and T cell activation. FEMS Immunol Med Microbiol. Dec. 2007;51(3):535-46. Epub Sep. 27, 2007.
Fontenot et al., Regulatory T cell lineage specification by the forkhead transcription factor foxp3. Immunity. Mar. 2005;22(3):329-41.
Fontenot et al., Foxp3 programs the development and function of CD4+CD25+ regulatory T cells. Nat Immunol. Apr. 2003;4(4):330-6. Epub Mar. 3, 2003.

(56) References Cited

OTHER PUBLICATIONS

Fournier et al., Isolation of type 5 capsular polysaccharide from *Staphylococcus aureus*. Ann Inst Pasteur Microbiol. Sep.-Oct. 1987;138(5):561-7.

Frank et al., Molecular-phylogenetic characterization of microbial community imbalances in human inflammatory bowel diseases. Proc Natl Acad Sci U S A. Aug. 21, 2007;104(34):13780-5. Epub Aug. 15, 2007.

Fridkis-Hareli et al., Binding motifs of copolymer 1 to multiple sclerosis- and rheumatoid arthritis-associated HLA-DR molecules. J Immunol. Apr. 15, 1999;162(8):4697-704.

Fridkis-Hareli et al., Binding of random copolymers of three amino acids to class II MHC molecules. Int Immunol. May 1999;11(5):635-41.

Fridkis-Hareli et al., Direct binding of myelin basic protein and synthetic copolymer 1 to class II major histocompatibility complex molecules on living antigen-presenting cells—specificity and promiscuity. Proc Natl Acad Sci U S A. May 24, 1994;91(11):4872-6.

Fridkis-Hareli et al., Synthetic copolymer 1 and myelin basic protein do not require processing prior to binding to class II major histocompatibility complex molecules on living antigen-presenting cells. Cell Immunol. Jul. 1995;163(2):229-36.

Froicu et al., A crucial role for the vitamin D receptor in experimental inflammatory bowel diseases. Mol Endocrinol. Dec. 2003;17(12):2386-92. Epub Sep. 18, 2003.

Froicu et al., Vitamin D receptor is required to control gastrointestinal immunity in IL-10 knockout mice. Immunology. Mar. 2006;117(3):310-8.

Fukuoka et al., Physico-chemical analysis of lipid A fractions of lipopolysaccharide from Erwinia carotovora in relation to bioactivity. Biochimica et Biophysica Acta. 2001;1510(1):185-97.

Gaboriau-Routhiau et al., The key role of segmented filamentous bacteria in the coordinated maturation of gut helper T cell responses. Immunity. Oct. 16, 2009;31(4):677-89. doi: 10.1016/j.immuni.2009.08.020.

Gally et al. Environmental regulation of the fim switch controlling type 1 fimbrial phase variation in *Escherichia coli* K-12: effects of temperature and media. (1993) J Bacteriol 175:6186-93.

Garrett et al., Colitis-associated colorectal cancer driven by T-bet deficiency in dendritic cells. Cancer Cell. Sep. 8, 2009;16(3):208-19. doi: 10.1016/j.ccr.2009.07.015.

Garrett et al., Enterobacteriaceae act in concert with the gut microbiota to induce spontaneous and maternally transmitted colitis. Cell Host Microbe. Sep. 16, 2010;8(3):292-300. doi: 10.1016/j.chom.2010.08.004.

Gelu-Simeon, et al., Evaluation and predictive factors of thyroid disorder due to interferon alpha in the treatment of hepatitis C. World J Gastroenterol 2009; 15(3):328-333.

Gerard et al., Interleukin 10 reduces the release of tumor necrosis factor and prevents lethality in experimental endotoxemia. J Exp Med. Feb. 1, 1993;177(2):547-50.

Gibson et al., Cellular mechanism of intraabdominal abscess formation by Bacteroides fragilis. J Immunol. May 15, 1998;160(10):5000-6.

Gibson et al., Chapter 5: trans-Galactooligosaccharides as Prebiotics. Handbook of Functional Dairy Products. Edited by Colette Shortt and John O'Brien. Published by CRC Press. 2004. pp. 91-108.

Gibson et al., The capsular polysaccharide complex of Bacteroides fragilis induces cytokine production from human and murine phagocytic cells. Infect Immun. Mar. 1996;64(3):1065-9.

Gill et al., Metagenomic analysis of the human distal gut microbiome. Science. Jun. 2, 2006;312(5778):1355-9.

Glazebrook et al., A novel exopolysaccharide can function in place of the calcofluor-binding exopolysaccharide in nodulation of alfalfa by Rhizobium meliloti. Cell. Feb. 24, 1989;56(4):661-72.

Golgher et al., Galactofuranose-containing glycoconjugates of epimastigote and trypomastigote forms of Trypanosoma cruzi. Mol Biochem Parasitol. Aug. 1993;60(2):249-64.

Gondek et al., Cutting edge: contact-mediated suppression by CD4+CD25+ regulatory cells involves a granzyme B-dependent, perforin-independent mechanism. J Immunol. Feb. 15, 2005;174(4):1783-6.

Gonzalez-Hernandez et al., Peripheral blood CD161+ T cells from asthmatic patients are activated during asthma attack and predominantly produce IFN-gamma. Scand J Immunol. Apr. 2007;65(4):368-75.

Goverman Autoimmune T cell responses in the central nervous system. Nat Rev Immunol. Jun. 2009;9(6):393-407. doi: 10.1038/nri2550.

Goverman et al., Transgenic mice that express a myelin basic protein-specific T cell receptor develop spontaneous autoimmunity. Cell. Feb. 26, 1993;72(4):551-60.

Grabow, Bacteriophages: Update on application as models for viruses in water. Water SA 2001;27(2):251-268.

Greenberger, P.A.; Drug allergy. J Allergy Clin Immunol 2006; 117(2):S464-S470.

Groux et al., A CD4+ T-cell subset inhibits antigen-specific T-cell responses and prevents colitis. Nature. Oct. 16, 1997;389(6652):737-42.

Groux et al., Type I T-regulatory cells: their role in the control of immune responses. Transplantation. May 15, 2003;75(9 Suppl):8S-12S.

Grivennikov et al., IL-6 and Stat3 are required for survival of intestinal epithelial cells and development of colitis-associated cancer. Cancer Cell. Feb. 3, 2009;15(2):103-13. doi: 10.1016/j.ccr.2009.01.001.

Hafler et al., Anti-CD4 and anti-CD2 monoclonal antibody infusions in subjects with multiple sclerosis. Immunosuppressive effects and human anti-mouse responses. J Immunol. Jul. 1, 1988;141(1):131-8.

Hall et al., Commensal DNA limits regulatory T cell conversion and is a natural adjuvant of intestinal immune responses. Immunity. Oct. 17, 2008;29(4):637-49. doi: 10.1016/j.immuni.2008.08.009. Epub Oct. 2, 2008.

Hamelmann et al., Noninvasive measurement of airway responsiveness in allergic mice using barometric plethysmography. Am J Respir Crit Care Med. Sep. 1997;156(3 Pt 1):766-75.

Hampe et al., A genome-wide association scan of nonsynonymous SNPs identifies a susceptibility variant for Crohn disease in ATG16L1. Nat Genet. Feb. 2007;39(2):207-11. Epub Dec. 31, 2006.

Hampe et al., Association between insertion mutation in NOD2 gene and Crohn's disease in German and British populations. Lancet. Jun. 16, 2001;357(9272):1925-8.

Haregewoin et al., Human gamma delta+ T cells respond to mycobacterial heat-shock protein.Nature. Jul. 27, 1989;340(6231):309-12.

Harth et al. Treatment of mycobacterium tuberculosis with antisense oligonucleotides to glutamine synthetase mRNA inhibits glutamine synthetase activity, formation of poly-L-glutamate/glutamine cell wall structure, and bacterial replication. Proc Natl. Acad. Sci. 97:418-423, 2000.

He et al., Intestinal bacteria trigger T cell-independent immunoglobulin A(2) class switching by inducing epithelial-cell secretion of the cytokine APRIL. Immunity. Jun. 2007;26(6):812-26.

Hertl et al., T cell control in autoimmune bullous skin disorders. J Clin Invest. May 2006;116(5):1159-66. Review.

Hewison et al., Differential regulation of vitamin D receptor and its ligand in human monocyte-derived dendritic cells. J Immunol. Jun. 1, 2003;170(11):5382-90.

Hirata et al., Cytokine synthesis of human monocytes stimulated by triple or single helical conformer of an antitumour (1—>3)-beta-D-glucan preparation, sonifilan. Zentralbl Bakteriol. Nov. 1998;288(3):403-13.

Hodge et al., Allium sativum (garlic) suppresses leukocyte inflammatory cytokine production in vitro: potential therapeutic use in the treatment of inflammatory bowel disease. Cytometry. Aug. 1, 2002;48(4):209-15.

Hofstetter et al., Th17 Cells in MS and Experimental Autoimmune Encephalomyelitis. Int MS J. Apr. 2009;16(1):12-8.

Hooper, Do symbiotic bacteria subvert host immunity? Nat Rev Microbiol. May 2009;7(5):367-74. doi: 10.1038/nrmicro2114.

(56) References Cited

OTHER PUBLICATIONS

Hooper et al., Commensal host-bacterial relationships in the gut. Science. May 11, 2001;292(5519):1115-8.
Hori et al., Control of regulatory T cell development by the transcription factor Foxp3. Science. Feb. 14, 2003;299(5609):1057-61. Epub Jan. 9, 2003.
Horstman et al., Enterotoxigenic *Escherichia coli* secretes active heat-labile enterotoxin via outer membrane vesicles. J Biol Chem. Apr. 28, 2000;275(17):12489-96.
Hu et al., Inflammation-induced tumorigenesis in the colon is regulated by caspase-1 and NLRC4. Proc Natl Acad Sci U S A. Dec. 14, 2010;107(50):21635-40. doi: 10.1073/pnas.1016814108. Epub Nov. 30, 2010.
Hue et al., Interleukin-23 drives innate and T cell-mediated intestinal inflammation. J Exp Med. Oct. 30, 2006;203(11):2473-83. Epub Oct. 9, 2006.
Huibregtse et al.., Immunopathogenesis of IBD: insufficient suppressor function in the gut? Gut. Apr. 2007;56(4):584-92. Epub Oct. 17, 2006.
Hutloff et al., ICOS is an inducible T-cell co-stimulator structurally and functionally related to CD28. Nature. Jan. 21, 1999;397(6716):263-6.
Isaksson et al., Conditional DC depletion does not affect priming of encephalitogenic Th cells in EAE. Eur J Immunol. Oct. 2012;42(10):2555-63. doi: 10.1002/eji.201142239. Epub Aug. 8, 2012.
Ishikawa et al., Effect of intestinal microbiota on the induction of regulatory CD25+ CD4+ T cells. Clin Exp Immunol. Jul. 2008;153(1):127-35. doi: 10.1111/j.1365-2249.2008.03668.x. Epub May 5, 2008.
Itokazu et al., Abscess formation as a complication caused by postoperative osteomyelitis of the femur. Arch Orthop Trauma Surg. 1998;118(1-2):99-102. Review.
Itzkowitz et al., Diagnosis and management of dysplasia in patients with inflammatory bowel diseases. Gastroenterology. May 2004;126(6):1634-48.
Ivanov et al., Transcriptional regulation of Th17 cell differentiation. Semin Immunol. Dec. 2007;19(6):409-17. Epub Nov. 28, 2007.
Ivanov et al., The orphan nuclear receptor RORgammat directs the differentiation program of proinflammatory IL-17+ T helper cells. Cell. Sep. 22, 2006;126(6):1121-33.
Ivanov et al., Induction of intestinal Th17 cells by segmented filamentous bacteria. Cell. Oct. 30, 2009;139(3):485-98. doi: 10.1016/j.cell.2009.09.033.
Ivanov et al., Specific microbiota direct the differentiation of IL-17-producing T-helper cells in the mucosa of the small intestine. Cell Host Microbe. Oct. 16, 2008;4(4):337-49. doi: 10.1016/j.chom.2008.09.009.
Izcue et al., Regulatory T cells suppress systemic and mucosal immune activation to control intestinal inflammation. Immunol Rev. Aug. 2006;212:256-71.
Jawad et al., Inflammatory bowel disease and colon cancer. Recent Results Cancer Res. 2011;185:99-115. doi: 10.1007/978-3-642-03503-6_6.
Jeffery et al., 1,25-Dihydroxyvitamin D3 and IL-2 combine to inhibit T cell production of inflammatory cytokines and promote development of regulatory T cells expressing CTLA-4 and FoxP3. J Immunol. Nov. 1, 2009;183(9):5458-67. doi: 10.4049/jimmunol.0803217.
Jennings et al., Immunochemistry of groups A, B, and C meningococcal polysaccharide-tetanus toxoid conjugates. J Immunol. Sep. 1981;127(3):1011-8.
Jennings et al., Induction of meningococcal group B polysaccharide-specific IgG antibodies in mice by using an N-propionylated B polysaccharide-tetanus toxoid conjugate vaccine. J Immunol. Sep. 1, 1986;137(5):1708-13.
Jennings et al., Structure of the Complex Polysaccharide C-Substance from *Streptococcus pneumoniae* Type 1; Biochem. 19:4712-4719 (1980).
Jia et al., Gut microbiota: a potential new territory for drug targeting. Nat Rev Drug Discov. Feb. 2008;7(2):123-9. doi: 10.1038/nrd2505.
Johnson et al., Bacterial capsular polysaccharide prevents the onset of asthma through T-cell activation. Glycobiology. Apr. 2015;25(4):368-75. doi: 10.1093/glycob/cwu117. Epub Oct. 27, 2014.
Jonuleit et al., Identification and functional characterization of human CD4(+)CD25(+) T cells with regulatory properties isolated from peripheral blood. J Exp Med. Jun. 4, 2001;193(11):1285-94.
Jonuleit et al., The regulatory T cell family: distinct subsets and their interrelations. J Immunol. Dec. 15, 2003;171(12):6323-7.
Joshi et al., 1,25-dihydroxyvitamin D(3) ameliorates Th17 autoimmunity via transcriptional modulation of interleukin-17A. Mol Cell Biol. Sep. 2011;31(17):3653-69. doi: 10.1128/MCB.05020-11. Epub Jul. 11, 2011.
Jotwani et al., Pathogenicity of Bacteroides fragilis group in rat intra-abdominal abscesses. Microbiol Immunol. 1992;36(10):1041-9.
Jyonouchi, H.; Non-IgE Mediated Food Allergy; Inflammation & Allergy—Drug Targets 2008;7(3):1-8.
Kakalacheva et al., Viral triggers of multiple sclerosis. Biochim Biophys Acta. Feb. 2011;1812(2):132-40. doi: 10.1016/j.bbadis.2010.06.012. Epub Jun. 25, 2010.
Kakalacheva et al., Environmental triggers of multiple sclerosis. FEBS Lett. Dec. 1, 2011;585(23):3724-9. doi: 10.1016/j.febslet.2011.04.006. Epub Apr. 7, 2011.
Kalka-Moll et al., Bacteriodes Fragilis NCTC 9343 Capsular Polysaccharide PS A and the Effect of Chain Length of T cell Proliferation. Abstracts of the 98$^{th}$ Gen Mtg of the American Soc for Microbiol. 1998;98:123. Abstract B-405.
Kalka-Moll et al., Immunochemical and biological characterization of three capsular polysaccharides from a single Bacteroides fragilis strain. Infect Immun. Apr. 2001;69(4):2339-44.
Kalka-Moll et al., Effect of molecular size on the ability of zwitterionic polysaccharides to stimulate cellular immunity. J Immunol. Jan. 15, 2000;164(2):719-24.
Kalka-Moll, et al., Zwitterionic Polysaccharides Stimulate T Cells by MHC Class II-Dependent Interactions; J. Immunol.; 2002;169:6149-6153.
Kasper et al., Capsular polysaccharides and lipopolysaccharides from two Bacteroides fragilis reference strains: chemical and immunochemical characterization. J Bacteriol. Feb. 1983;153(2):991-7.
Kasper et al., Protective efficacy of immunization with capsular antigen against experimental infection with Bacteroides fragilis. J Infect Dis. Nov. 1979;140(5):724-31.
Kasper et al., Surface antigens as virulence factors in infection with Bacteroides fragilis. Rev Infect Dis. Mar.-Apr. 1979;1(2):278-90.
Kasper et al., The polysaccharide capsule of *Bacteroides fragilis* subspecies *fragilis*: immunochemical and morphologic definition. J Infect Dis. Jan. 1976;133(1):79-87.
Kato et al., Interleukin 10 reduces mortality from severe peritonitis in mice. Antimicrob Agents Chemother. Jun. 1995;39(6):1336-40.
Kenne et al., Structural studies of the O-specific side-chains of the Shigella sonnei phase I lipopolysaccharide. Carbohydrate Res. 1980;78:119-126.
Kennedy et al., Prevention of experimental postoperative peritoneal adhesions by N,O-carboxymethyl chitosan. Surgery. Nov. 1996;120(5):866-70.
Kernodle et al. Expression of an antisense hla fragment in *Staphylococcus aureus* reduces alpha-toxin production in vitro and attenuates lethal activity in a murine model. Infection and Immunity 179-184. 1997.
Kesty et al., Incorporation of heterologous outer membrane and periplasmic proteins into *Escherichia coli* outer membrane vesicles. J Biol Chem. Jan. 16, 2004;279(3):2069-76. Epub Oct. 24, 2003.
Kidd, Th1/Th2 balance: the hypothesis, its limitations, and implications for health and disease. Altern Med Rev. Aug. 2003;8(3):223-46.
Kim et al., Regulatory T cells prevent catastrophic autoimmunity throughout the lifespan of mice. Nat Immunol. Feb. 2007;8(2):191-7. Epub Nov. 30, 2006.

(56) References Cited

OTHER PUBLICATIONS

Kinoshita et al., Retinoic acid reduces autoimmune renal injury and increases survival in NZB/W F1 mice. J Immunol. Jun. 1, 2003;170(11):5793-8.
Kirjavainen et al., Healthy gut microflora and allergy: factors influencing development of the microbiota. Ann Med. Aug. 1999;31(4):288-92.
Knetsch et al., Polymers with tunable toxicity: a reference scale for cytotoxicity testing of biomaterial surfaces. J Biomed Mater Res A. Sep. 15, 2007;82(4):947-57.
Knirel et al., Somatic antigens of Pseudomonas aeruginosa. The structure of O-specific polysaccharide chains of lipopolysaccharides of P. aeruginosa O3 (Lanyi), O25 (Wokatsch) and Fisher immunotypes 3 and 7. Eur J Biochem. Sep. 15, 1987;167(3):549-61.
Knirel et al., The structure of O-specific polysaccharides and serological classification of Pseudomonas aeruginosa (a review). Acta Microbiol Hung. 1988;35(1):3-24. Review.
Koch et al., The transcription factor T-bet controls regulatory T cell homeostasis and function during type 1 inflammation. Nat Immunol. Jun. 2009;10(6):595-602. doi: 10.1038/ni.1731. Epub May 3, 2009.
Kong et al., Novel role of the vitamin D receptor in maintaining the integrity of the intestinal mucosal barrier. Am J Physiol Gastrointest Liver Physiol. Jan. 2008;294(1):G208-16. Epub Oct. 25, 2007.
Kormelink et al.; Atopic and non-atopic allergic disorders: current insights into the possible involvement of free immunoglobulin light chains; Clinical and Experimental Allergy 2008;39:33-42.
Krause et al., An Inhibitor of Cell Proliferation Associated with Adhesion Formation Is Suppressed by N,O-Carboxymethyl Chitosan. J Invest Surg. 1988;11:105-113.
Krinos et al., Extensive surface diversity of a commensal microorganism by multiple DNA inversions. (2001) Nature 414:555-8.
Krutzik et al., IL-15 links TLR2/1-induced macrophage differentiation to the vitamin D-dependent antimicrobial pathway. J Immunol. Nov. 15, 2008;181(10):7115-20.
Kuehn et al., Bacterial outer membrane vesicles and the host-pathogen interaction. Genes Dev. Nov. 15, 2005;19(22):2645-55.
Kuhn et al., Interleukin-10-deficient mice develop chronic enterocolitis. Cell. Oct. 22, 1993;75(2):263-74.
Kulberg et al., Bacteria-triggered CD4(+) T regulatory cells suppress Helicobacter hepaticus-induced colitis. J Exp Med. Aug. 19, 2002;196(4):505-15.
Kulberg et al., IL-23 plays a key role in Helicobacter hepaticus-induced T cell-dependent colitis. J Exp Med. Oct. 30, 2006;203(11):2485-94. Epub Oct. 9, 2006.
Kulberg et al., Induction of colitis by a CD4+ T cell clone specific for a bacterial epitope. Proc Natl Acad Sci U S A. Dec. 23, 2003;100(26):15830-5. Epub Dec. 12, 2003.
Kulberg et al., Helicobacter hepaticus triggers colitis in specific-pathogen-free interleukin-10 (IL-10)-deficient mice through an IL-12- and gamma interferon-dependent mechanism. Infect Immun. Nov. 1998;66(11):5157-66.
Kulicke et al., Correlation between immunological activity, molar mass, and molecular structure of different (1—>3)-beta-D-glucans. Carbohydr Res. Jan. 2, 1997;297(2):135-43.
Kuper et al., Infections as a major preventable cause of human cancer. J Intern Med. Sep. 2000;248(3):171-83.
Kurup et al., Antibody response to low-molecular-weight antigens of Aspergillus fumigatus in allergic bronchopulmonary aspergillosis. J Clin Microbiol. Jun. 1989;27(6):1312-6.
Lagishetty et al., Vitamin D deficiency in mice impairs colonic antibacterial activity and predisposes to colitis. Endocrinology. Jun. 2010;151(6):2423-32. doi: 10.1210/en.2010-0089. Epub Apr. 14, 2010.
Lee et al., Bacterial colonization factors control specificity and stability of the gut microbiota. Nature. Sep. 19, 2013;501(7467):426-9. doi: 10.1038/nature12447. Epub Aug. 18, 2013.
Lee et al., Proinflammatory T-cell responses to gut microbiota promote experimental autoimmune encephalomyelitis. Proc Natl Acad Sci U S A. Mar. 15, 2011;108 Suppl 1:4615-22. doi: 10.1073/pnas.1000082107. Epub Jul. 26, 2010.

Lee et al., Has the microbiota played a critical role in the evolution of the adaptive immune system? Science. Dec. 24, 2010;330(6012):1768-73. doi: 10.1126/science.1195568.
Lee et al., Effects of IN Vitro and In Vivo and Growth Conditions on Expression of Type 8 Capsular Polysaccharide by Staphylococcus aureus, Infection and Immunity, 61:1853-1858, 1993.
Ley et al., Ecological and evolutionary forces shaping microbial diversity in the human intestine. Cell. Feb. 24, 2006;124(4):837-48.
Ley et al., Evolution of mammals and their gut microbes. Science. Jun. 20, 2008;320(5883):1647-51. doi: 10.1126/science.1155725. Epub May 22, 2008.
Lin et al., Regulatory T cell development in the absence of functional Foxp3. Nat Immunol. Apr. 2007;8(4):359-68. Epub Feb. 2, 2007.
Lindberg et al., Structural Studies of the Capsular Polysaccharide from Streptococcus pneumoniae Type 1; Carbohydrate Res 78:111-117 (1980).
Lindberg et al., Virulence factors in infections with bacteroides fragilis: isolation and characterization of capsular polysaccharide and lipopolysaccharide. Scand J Infect Dis Suppl. 1982;35:45-52.
Liu et al., Altered endocrine and autocrine metabolism of vitamin D in a mouse model of gastrointestinal inflammation. Endocrinology. Oct. 2008;149(10):4799-808. doi: 10.1210/en.2008-0060. Epub Jun. 5, 2008.
Liu et al., Toll-like receptor 2 signaling modulates the functions of CD4+ CD25+ regulatory T cells. Proc Natl Acad Sci U S A. May 2, 2006;103(18):7048-53. Epub Apr. 21, 2006.
Liu et al., Regulation of surface architecture by symbiotic bacteria mediates host colonization. Proc Natl Acad Sci U S A. Mar. 11, 2008;105(10):3951-6. doi: 10.1073/pnas.0709266105. Epub Mar. 4, 2008.
Liu et al., Toll-like receptor triggering of a vitamin D-mediated human antimicrobial response. Science. Mar. 24, 2006;311(5768):1770-3. Epub Feb. 23, 2006.
Lysnyansky et al. Juxtaposition of an active promoter to vsp genes via site-specific DNA inversions generates antigenic variation in Mycoplasma bovis. (2001) J Bacteriol 183:5698-5708.
Maconi et al., Contrast radiology, computed tomography, and ultrasonography in detecting internal fistulas and intra-abdominal abscesses in Chrohn's disease: a prospective comparative study. Amer J Gast. 2003;98(7):1545-1555.
Macpherson et al., Interactions between commensal intestinal bacteria and the immune system. Nat Rev Immunol. Jun. 2004;4(6):478-85.
Macpherson et al., IgA responses in the intestinal mucosa against pathogenic and non-pathogenic microorganisms. Microbes Infect. Oct. 2001;3(12):1021-35.
Macpherson et al., Mucosal antibodies in inflammatory bowel disease are directed against intestinal bacteria. Gut. Mar. 1996;38(3):365-75.
Macpherson et al., Induction of protective IgA by intestinal dendritic cells carrying commensal bacteria. Science. Mar. 12, 2004;303(5664):1662-5.
Maier et al., Experimental Shigella infections in laboratory animals. I. Antagonism by human normal flora components in gnotobiotic mice. Infect Immun. Aug. 1972;6(2):168-73.
Makela et al., IL-10 is necessary for the expression of airway hyperresponsiveness but not pulmonary inflammation after allergic sensitization. Proc Natl Acad Sci U S A. May 23, 2000;97(11):6007-12.
Maloy et al., CD4+CD25+ T(R) cells suppress innate immune pathology through cytokine-dependent mechanisms. J Exp Med. Jan. 6, 2003;197(1):111-9.
Mamessier et al., Cytokines in atopic diseases: revisiting the Th2 dogma. Eur J Dermatol. Mar.-Apr. 2006;16(2):103-13. Review.
Mancuso et al., Bacteroides fragilis-derived lipopolysaccharide produces cell activation and lethal toxicity via toll-like receptor 4. Infect Immun. Sep. 2005;73(9):5620-7.
Mantovani et al., Cancer-related inflammation. Nature. Jul. 24, 2008;454(7203):436-44. doi: 10.1038/nature07205.
Maynard et al., Diversity in the contribution of interleukin-10 to T-cell-mediated immune regulation. Immunol Rev. Dec. 2008;226:219-33. doi: 10.1111/j.1600-065X.2008.00711.x.

(56) References Cited

OTHER PUBLICATIONS

Maynard et al., Contrasting roles for all-trans retinoic acid in TGF-beta-mediated induction of Foxp3 and I110 genes in developing regulatory T cells. J Exp Med. Feb. 16, 2009;206(2):343-57. doi: 10.1084/jem.20080950. Epub Feb. 9, 2009.
Maynard et al., Regulatory T cells expressing interleukin 10 develop from Foxp3+ and Foxp3-precursor cells in the absence of interleukin 10. Nat Immunol. Sep. 2007;8(9):931-41. Epub Aug. 12, 2007.
Mayne et al., 1,25-Dihydroxyvitamin D3 acts directly on the T lymphocyte vitamin D receptor to inhibit experimental autoimmune encephalomyelitis. Eur J Immunol. Mar. 2011;41(3):822-32. doi: 10.1002/eji.201040632. Epub Feb. 1, 2011.
Mazmanian et al., An immunomodulatory molecule of symbiotic bacteria directs maturation of the host immune system. Cell. Jul. 15, 2005;122(1):107-18.
Mazmanian et al., Bacterial immunomodulatory regulation during mammalian health and disease. Harvard Medical School and Brigham and Women's Hospital. Presentation. Oct. 11, 2005. 51 pages.
Mazmanian et al., Host-bacterial symbiosis prevents intestinal inflammatory disease. California Institute of Technology. Presentation. Amgen. Jul. 2008. 47 pages.
Mazmanian et al., The evolution of symbiosis: from bacteria to commensal to beneficial microbe. Harvard Medical School and California Institute of Technology. Presentation. Oct. 4, 2006. 24 pages.
Mazmanian et al., The love-hate relationship between bacterial polysaccharides and the host immune system. Nature Reviews Immunology. 2006;6: 849-858.
Mazmanian et al., Capsular polysaccharides of symbiotic bacteria modulate immune responses during experimental colitis. J Pediatr Gastroenterol Nutr. Apr. 2008;46 Suppl 1:E11-2. doi: 10.1097/01.mpg.0000313824.70971.a7.
Mazmanian et al., A microbial symbiosis factor prevents intestinal inflammatory disease. Nature. May 29, 2008;453(7195):620-5. doi: 10.1038/nature07008.
Mcclain et al. Inversion-independent phase variation of type 1 fimbriae in *Escherichia coli*. (1993) J Bacteriol 175(14):4335-44.
Mcmurchy et al., Suppression assays with human T regulatory cells: a technical guide. Eur J Immunol. Jan. 2012;42(1):27-34. doi: 10.1002/eji.201141651. Epub Dec. 1, 20112.
Meisel-Mikolajczyk et al., Human T cell adhesion to endothelium stimulated by membrane components extracted from strains of Bacteroides vulgatus (member of B. fragilis group). Arch Immunol Ther Exp (Warsz). 1993;41(2):129-31.
Mertens et al., *Streptococcus pneumoniae* serotype 1 capsular polysaccharide induces CD8 CD28 regulatory T lymphocytes by TCR crosslinking. PLoS Pathog. Sep. 2009;5(9):e1000596. doi: 10.1371/journal.ppat.l000596. Epub Sep. 25, 2009.
Miller et al., Severe asthma and the omalizumab option. Clinical and Molecular Allergy 2008, 6:4.
Min et al., Gut flora antigens are not important in the maintenance of regulatory T cell heterogeneity and homeostasis. Eur J Immunol. Jul. 2007;37(7):1916-23.
Mojtabavi et al., Long-lived Th2 memory in experimental allergic asthma. J Immunol. Nov. 1, 2002;169(9):4788-96.
Montz et al., Interleukin 10: ability to minimize postoperative intraperitoneal adhesion formation in a murine model. Fertil Steril. Jun. 1994;61(6):1136-40.
Moore, The List Goes On, New Additions to the Autoimmune Disease Roster. http://autoimmunedisease.suite101.com/blog.cfm/the_list_goes_on. pp. 1-3.
Moorman et al., National Surveillance of Asthma: United States, 2001-2010. National Center for Health Statistics. Vital Health Stat. 2012;3(35) 67 pages.
Mor et al., Identification of aldolase as a target antigen in Alzheimer's disease. J Immunol. Sep. 1, 2005;175(5):3439-45.
Mora et al., Generation of gut-homing IgA-secreting B cells by intestinal dendritic cells. Science. Nov. 17, 2006;314(5802):1157-60.
Mora et al., Selective imprinting of gut-homing T cells by Peyer's patch dendritic cells. Nature. Jul. 3, 2003;424(6944):88-93.
Morales-Tirado et al., 1α,25-dihydroxyvitamin D3 (vitamin D3) catalyzes suppressive activity on human natural regulatory T cells, uniquely modulates cell cycle progression, and augments FOXP3. Clin Immunol. Feb. 2011;138(2):212-21. doi: 10.1016/j.clim.2010.11.003. Epub Dec. 16, 2010.
Motta et al., T cells in asthma: Lessons from mouse models. Drug Discovery Today; Disease Models. 2006;3(3):199-204.
Mulholland et al., Strategies for the control of pneumococcal diseases. Vaccine. Jul. 30, 1999; 17 Suppl 1:S79-84. Review.
Nakayama-Imaohji et al., Identification of the site-specific DNA invertase responsible for the phase variation of SusC/SusD family outer membrane proteins in Bacteroides fragilis. J Bacteriol. Oct. 2009;191(19):6003-11. doi: 10.1128/JB.00687-09. Epub Jul. 31, 2009.
Natori et al., Agelasphins, novel antitumor and immunostimulatory cerebrosides from the marine sponge Agelas mauritianus. Tetrahedron. 1994;50(9):2771-2784.
Neurath et al., TNBS-colitis. Int Rev Immunol. 2000;19(1):51-62.
Nielsen et al., Applications of peptide nucleic acids. Curr Opin Biotechnol. Feb. 1999;10(1):71-5. Review.
Niess et al., Commensal gut flora drives the expansion of proinflammatory CD4 T cells in the colonic lamina propria under normal and inflammatory conditions. J Immunol. Jan. 1, 2008;180(1):559-68.
NORMAN; "Thyroiditis—Inflammation of the thyroid gland"; Endocrineweb 2009; www.endocrineweb.com/throiditis.html, 1-4. Downloaded Jul. 28, 2009.
Noverr et al., Does the microbiota regulate immune responses outside the gut? Trends Microbiol. Dec. 2004;12(12):562-8.
Nylander et al., Multiple sclerosis. J Clin Invest. Apr. 2012;122(4):1180-8. doi: 10.1172/JCI58649. Epub Apr. 2, 2012.
O'Connor et al., Translational mini-review series on Th17 cells: CD4 T helper cells: functional plasticity and differential sensitivity to regulatory T cell-mediated regulation. Clin Exp Immunol. Feb. 2010;159(2):137-47. doi: 10.1111/j.1365-2249.2009.04040.x. Epub Nov. 11, 2009.
O'Garra et al., IL-10-producing and naturally occurring CD4+ Tregs: limiting collateral damage. J Clin Invest. Nov. 2004;114(10):1372-8.
O'Hara et al., The gut flora as a forgotten organ. EMBO Rep. Jul. 2006;7(7):688-93.
Ochoa-Reparaz et al., Central nervous system demyelinating disease protection by the human commensal Bacteroides fragilis depends on polysaccharide A expression. J Immunol. Oct. 1, 2010;185(7):4101-8. doi: 10.4049/jimmunol.1001443. Epub Sep. 3, 2010.
Ochoa-Reparaz, J. et al., The role of subcellular fractions of commensal Bacteroides fragilis in the control of experimental autoimmune encephalomyelitis. Multiple Sclerosis. 2009;15:S61. Poster P236.
Ochoa-Reparaz et al., Role of gut commensal microflora in the development of experimental autoimmune encephalomyelitis. J Immunol. Nov. 15, 2009;183(10):6041-50. doi: 10.4049/jimmunol.0900747. Epub Oct. 19, 2009.
Ochoa-Reparaz et al., A polysaccharide from the human commensal Bacteroides fragilis protects against CNS demyelinating disease. Mucosal Immunol. Sep. 2010;3(5):487-95. doi: 10.1038/mi.2010.29. Epub Jun. 9, 2010.
Oda et al., A comprehensive map of the toll-like receptor signaling network. Mol Syst Biol. 2006;2:2006.0015. Epub Apr. 18, 2006.
Oh et al., CD4 T-helper cells engineered to produce IL-10 prevent allergen-induced airway hyperreactivity and inflammation. J Allergy Clin Immunol. Sep. 2002;110(3):460-8.
Ohno et al., Comparison of the immunopharmacological activities of triple and single-helical schizophyllan in mice. Biol Pharm Bull. Sep. 1995;18(9):1242-7.
Ohno et al., Enhancement of LPS triggered TNF-alpha (tumor necrosis factor-alpha) production by (1→3)-beta-D-glucans in mice. Biol Pharm Bull. Jan. 1995;18(1):126-33.

(56) References Cited

OTHER PUBLICATIONS

Onderdonk et al., The capsular polysaccharide of Bacteroides fragilis as a virulence factor: comparison of the pathogenic potential of encapsulated and unencapsulated strains. J Infect Dis. Jul. 1977;136(1):82-9.
Onderdonk et al., Evidence for T Cell-dependent Immunity to Bacteroides fragilis in an Intraabdominal Abscess Model; J. Clin Invest. 69:9-16 (1982).
Ostman et al., Impaired regulatory T cell function in germ-free mice. Eur J Immunol. Sep. 2006;36(9):2336-46.
Ozenci et al., Multiple sclerosis: levels of interleukin-10-secreting blood mononuclear cells are low in untreated patients but augmented during interferon-beta-1b treatment. Scand J Immunol. May 1999;49(5):554-61.
Palmer et al., Lineage-specific effects of 1,25-dihydroxyvitamin D(3) on the development of effector CD4 T cells. J Biol Chem. Jan. 14, 2011;286(2):997-1004. doi: 10.1074/jbc.M110.163790. Epub Nov. 3, 2010.
Palmer et al., Development of the human infant intestinal microbiota. PLoS Biol. Jul. 2007;5(7):e177. Epub Jun. 26, 2007.
Pamer, Immune responses to commensal and environmental microbes. Nat Immunol. Nov. 2007;8(11):1173-8.
Pantosti et al., Bacteroides fragilis strains express multiple capsular polysaccharides. J Clin Microbiol. Jul. 1993;31(7):1850-5.
Pantosti et al., Immunochemical characterization of two surface polysaccharides of Bacteroides fragilis. Infect Immun. Jun. 1991;59(6):2075-82.
Paoletti et al., Neonatal Mouse Protection against Infection with Multiple Group B *Streptococcal* (GBS) Serotypes by Maternal Immunization with a Tetravalent GBS Polysaccharide-Tetanus Toxoid Conjugate Vaccine, Infection and Immunity, 62:3236-3243, 1994.
Paoletti et al., Effects of chain length on the immunogenicity in rabbits of group B *Streptococcus* type III oligosaccharide-tetanus toxoid conjugates. J Clin Invest. Jan. 1992;89(1):203-9.
Park et al., Interleukin-2 and soluble interleukin-2 receptor in bronchoalveolar lavage fluid from patients with bronchial asthma. Chest. Aug. 1994;106(2):400-6.
Pato et al., Purification of capsular polysaccharide from Neisseria meningitidis serogroup C by liquid chromatography. J Chromatogr B Analyt Technol Biomed Life Sci. Mar. 7, 2006;832(2):262-7. Epub Feb. 15, 2006.
Patrick et al., Separation of capsulate and non-capsulate Bacteroides fragilis on a discontinuous density gradient. J Med Microbiol. May 1983;16(2):239-41.
Patrick et al., A comparison of the haemagglutinating and enzymic activities of Bacteroides fragilis whole cells and outer membrane vesicles. Microb Pathog. Apr. 1996;20(4):191-202.
Patrick et al., Mutational analysis of genes implicated in LPS and capsular polysaccharide biosynthesis in the opportunistic pathogen Bacteroides fragilis. Microbiology. Apr. 2009;155(Pt 4):1039-49. doi: 10.1099/mic.0.025361-0.
Pavliak et al., Structural elucidation of the capsular polysaccharide of Bacteroides fragilis strain 23745M1. Carbohydr Res. Oct. 2, 1995;275(2):333-41.
Pedersen et al., 1,25-dihydroxyvitamin D3 reverses experimental autoimmune encephalomyelitis by inhibiting chemokine synthesis and monocyte trafficking. J Neurosci Res. Aug. 15, 2007;85(11):2480-90.
Perumal et al., Protective effect of interleukin-2 on experimental intra-abdominal abscess development due to Bacteriodes Fragilis. Clinical Research. 1990;38(2):550A.
Pierrot-Deseilligny et al., Is hypovitaminosis D one of the environmental risk factors for multiple sclerosis? Brain. Jul. 2010;133(Pt 7):1869-88. doi: 10.1093/brain/awq147.
Poonawalla et al.; Urticaria a Review; Am J Clin Dermotol 2009; 10(1):9-21.
Popivanova et al., Blocking TNF-alpha in mice reduces colorectal carcinogenesis associated with chronic colitis. J Clin Invest. Feb. 2008;118(2):560-70. doi: 10.1172/JCI32453.
Popovic et al., Inhibition of autoimmune encephalomyelitis by a tetracycline. Ann Neurol. Feb. 2002;51(2):215-23.
Power et al., The human microbiome in multiple sclerosis: pathogenic or protective constituents? Can J Neurol Sci. Sep. 2010;37 Suppl 2:S24-33.
Powrie et al., Immunology. Regulating the regulators. Science. Feb. 14, 2003;299(5609):1030-1.
Poxton et al., Mucosa-associated bacterial flora of the human colon. J Med Microbiol. Jan. 1997;46(1):85-91.
Prieto et al., A New Ganglioside in Human Meconium Detected by Antiserum against the Human Milk Sialyloligosaccharide, LS-Tetrasacharide b.sup.1, Archives of Biochemistry and Biophysics, 241:281-289, 1985.
Rabe et al., Pharmacological treatment of asthma today. Eur Respir J Suppl. 2001;34:34s-40s.
Raetz et al., Lipopolysaccharide endotoxins. Annu Rev Biochem. 2002;71:635-700. Epub Nov. 9, 2001.
Raghuwanshi et al., Vitamin D and multiple sclerosis. J Cell Biochem. Oct. 1, 2008;105(2):338-43. doi: 10.1002/jcb.21858.
Rakoff-Nahoum et al., Recognition of commensal microflora by toll-like receptors is required for intestinal homeostasis. Cell. Jul. 23, 2004;118(2):229-41.
Raman et al., Vitamin D and gastrointestinal diseases: inflammatory bowel disease and colorectal cancer. Therap Adv Gastroenterol. Jan. 2011;4(1):49-62. doi: 10.1177/1756283X10377820.
Ranua et al., Serum IgA, IgG, and IgM concentrations in patients with epilepsy and matched controls: a cohort-based cross-sectional study. Epilepsy Behav. Mar. 2005;6(2):191-5.
Reed et al., A simple method of estimating fifty percent endpoints. Am J Hyg. 1938;27:493-497.
Rescigno et al., Dendritic cells express tight junction proteins and penetrate gut epithelial monolayers to sample bacteria. Nat Immunol. Apr. 2001;2(4):361-7.
Riesenfeld et al., Biosynthesis of heparin. Assay and properties of the microsomal N-acetyl-D-glucosaminyl N-deacetylase.J Biol Chem. Feb. 10, 1980;255(3):922-8.
Roncarolo et al., Type I T regulatory cells. Immunol Rev. Aug. 2001;182:68-79. Review.
Rose et al., Multifunctional role of dextran sulfate sodium for in vivo modeling of intestinal diseases. BMC Immunol. Aug. 1, 2012;13:41. doi: 10.1186/1471-2172-13-41.
Round et al., Coordination of tolerogenic immune responses by the commensal microbiota. J Autoimmun. May 2010;34(3):J220-5. doi: 10.1016/j.jaut.2009.11.007. Epub Dec. 6, 2009.
Round et al., The Toll-like receptor 2 pathway establishes colonization by a commensal of the human microbiota. Science. May 20, 2011;332(6032):974-7. doi: 10.1126/science.1206095. Epub Apr. 21, 2011.
Round et al., The gut microbiota shapes intestinal immune responses during health and disease. Nat Rev Immunol. May 2009;9(5):313-23. doi: 10.1038/nri2515.
Round et al., Inducible Foxp3+ regulatory T-cell development by a commensal bacterium of the intestinal microbiota. Proc Natl Acad Sci U S A. Jul. 6, 2010;107(27):12204-9. doi: 10.1073/pnas.0909122107. Epub Jun. 21, 2010.
Rubtsov et al., Regulatory T cell-derived interleukin-10 limits inflammation at environmental interfaces. Immunity. Apr. 2008;28(4):546-58. doi: 10.1016/j.immuni.2008.02.017.
Runia et al., Lower serum vitamin D levels are associated with a higher relapse risk in multiple sclerosis. Neurology. Jul. 17, 2012;79(3):261-6. doi: 10.1212/WNL.0b013e31825fdec7. Epub Jun. 13, 2012.
Ruiz-Perez et al., Modulation of surgical fibrosis by microbial zwitterionic polysaccharides. Proc Natl Acad Sci U S A. Nov. 15, 2005;102(46):16753-8. Epub Nov. 7, 2005.
Russell, Lethal effects of heat on bacterial physiology and structure. Sci Prog. 2003;86(Pt 1-2):115-37.
Rutgeerts et al., Infliximab for induction and maintenance therapy for ulcerative colitis. N Engl J Med. Dec. 8, 2005;353(23):2462-76.
Rypens et al., Percutaneous drainage of abdominal abscesses in pediatric Crohn's disease. AJR Am J Roentgenol. Feb. 2007;188(2):579-85.

(56) References Cited

OTHER PUBLICATIONS

Sakaguchi et al., Regulatory T cells and immune tolerance. Cell. May 30, 2008;133(5):775-87. doi: 10.1016/j.cell.2008.05.009.

Sakaguchi et al., Foxp3+ CD25+ CD4+ natural regulatory T cells in dominant self-tolerance and autoimmune disease. Immunol Rev. Aug. 2006;212:8-27.

Salyers et al., Conjugative transposons: an unusual and diverse set of integrated gene transfer elements. Microbiol Rev. Dec. 1995;59(4):579-90. Review.

Sartor, Mechanisms of disease: pathogenesis of Crohn's disease and ulcerative colitis. Nat Clin Pract Gastroenterol Hepatol. Jul. 2006;3(7):390-407.

Sawada et al., Leukocytapheresis in ulcerative colitis: results of a multicenter double-blind prospective case-control study with sham apheresis as placebo treatment. Am J Gastroenterol. Jun. 2005;100(6):1362-9.

Scheiffele et al., Induction of TNBS colitis in mice. Curr Protoc Immunol. Aug. 2002;Chapter 15:Unit 15.19. doi: 10.1002/0471142735.im1519s49.

Scheinin et al., Validation of the interleukin-10 knockout mouse model of colitis: antitumour necrosis factor-antibodies suppress the progression of colitis. Clin Exp Immunol. Jul. 2003;133(1):38-43.

Schembri Ma et al. Orientation-dependent enhancement by H-NS of the activity of the type 1 fimbrial phase switch promoter in *Escherichia coli*. (1998) Mol Gen Genet 259:336-44.

Schlegel et al., A synthetic random basic copolymer with promiscuous binding to class II major histocompatibility complex molecules inhibits T-cell proliferative responses to major and minor histocompatibility antigens in vitro and confers the capacity to prevent murine graft-versus-host disease in vivo. Proc Natl Acad Sci U S A. May 14, 1996;93(10):5061-6. Erratum in: Proc Natl Acad Sci U S A Aug. 6, 1996;93(16):8796.

Schneider et al., De novo design of molecular architectures by evolutionary assembly of drug-derived building blocks. J Comput Aided Mol Des. Jul. 2000;14(5):487-94.

Segal et al., Severe insulin resistance secondary to insulin antibodies: successful treatment with the immunosuppressant MMF. Pediatr Diabetes. Jun. 2008;9(3 Pt 1):250-4.

Sellin et al., Conformational analysis of a toxic peptide from Trimeresurus wagleri which blocks the nicotinic acetylcholine receptor. Biophys J. Jan. 1996;70(1):3-13.

Sellon et al., Resident enteric bacteria are necessary for development of spontaneous colitis and immune system activation in interleukin-10-deficient mice. Infect Immun. Nov. 1998;66(11):5224-31.

Shaklee et al., Hydrazinolysis of heparin and other glycosaminoglycans. Biochem. J. (1984); 217: 187-197.

Shapiro et al., Cellular control of abscess formation: role of T cells in the regulation of abscesses formed in response to Bacteroides fragilis. J Immunol. Jul. 1, 1986;137(1):341-6.

Shapiro et al., Cellular immunity to Bacteroides fragilis capsular polysaccharide. J Exp Med. Apr. 1, 1982;155(4):1188-97.

Sharpe et al., The B7-CD28 superfamily. Nat Rev Immunol. Feb. 2002;2(2):116-26. Review.

Shevach, CD4+ CD25+ suppressor T cells: more questions than answers. Nat Rev Immunol. Jun. 2002;2(6):389-400. Review.

Sigmundsdottir et al., DCs metabolize sunlight-induced vitamin D3 to 'program' T cell attraction to the epidermal chemokine CCL27. Nat Immunol. Mar. 2007;8(3):285-93. Epub Jan. 28, 2007.

Silvestro et al., Effects of subinhibitory concentrations of clindamycin on the morphological, biochemical and genetic characteristics of Bacteroides fragilis. FEMS Microbiol Lett. Apr. 2006;257(2):189-94.

Simmons et al., Synthesis and membrane permeability of PNA-peptide conjugates. Bioorg Med Chem Lett. 1997;7(23):3001-6.

Slack et al., Innate and adaptive immunity cooperate flexibly to maintain host-microbiota mutualism. Science. Jul. 31, 2009;325(5940):617-20. doi: 10.1126/science.1172747.

Smith et al. Functional analysis of the FimE integrase of *Escherichia coli* K-12: isolation of mutant derivatives with altered DNA inversion preferences. (1999) Mol Microbiol 34:965-79.

Smith et al., Use of axenic animals in studying the adaptation of mammals to their commensal intestinal microbiota. Semin Immunol. Apr. 2007;19(2):59-69. Epub Nov. 21, 2006.

Smits et al., Selective probiotic bacteria induce IL-10-producing regulatory T cells in vitro by modulating dendritic cell function through dendritic cell-specific intercellular adhesion molecule 3-grabbing nonintegrin. J Allergy Clin Immunol. Jun. 2005;115(6):1260-7.

Solomon et al., Multiple sclerosis and vitamin D: a review and recommendations. Curr Neurol Neurosci Rep. Sep. 2010;10(5):389-96. doi: 10.1007/s11910-010-0131-5.

Spach et al., Vitamin D3 confers protection from autoimmune encephalomyelitis only in female mice. J Immunol. Sep. 15, 2005;175(6):4119-26.

Spach et al., Gene expression analysis suggests that 1,25-dihydroxyvitamin D3 reverses experimental autoimmune encephalomyelitis by stimulating inflammatory cell apoptosis. Physiol Genomics. Jul. 8, 2004;18(2):141-51.

Sprinz et al., The response of the germfree guinea pig to oral bacterial challenge with *Escherichia coli* and Shigella flexneri. Am J Pathol. Dec. 1961;39:681-95.

Stein et al., Thymus-independent and thymus-dependent responses to polysaccharide antigens. J Infect Dis. Jun. 1992;165 Suppl 1:S49-52. Review.

Stewart et al., Interferon-β and serum 25-hydroxyvitamin D interact to modulate relapse risk in MS. Neurology. Jul. 17, 2012;79(3):254-60. doi: 10.1212/WNL.0b013e31825fded9. Epub Jun. 13, 2012.

Stingele et al., Zwitterionic polysaccharides stimulate T cells with no preferential V beta usage and promote anergy, resulting in protection against experimental abscess formation. J Immunol. Feb. 1, 2004;172(3):1483-90.

Stockinger et al., Differentiation and function of Th17 T cells. Curr Opin Immunol. Jun. 2007;19(3):281-6. Epub Apr. 12, 2007.

Strachan, Hay fever, hygiene, and household size. BMJ. Nov. 18, 1989;299(6710):1259-60.

Strauch et al., Influence of intestinal bacteria on induction of regulatory T cells: lessons from a transfer model of colitis. Gut. Nov. 2005;54(11):1546-52. Epub Jun. 29, 2005.

Strober, The multifaceted influence of the mucosal microflora on mucosal dendritic cell responses. Immunity. Sep. 18, 2009;31(3):377-88. doi: 10.1016/j.immuni.2009.09.001.

Stromnes et al., Active induction of experimental allergic encephalomyelitis. Nat Protoc. 2006;1(4):1810-9.

Stromnes et al., Passive induction of experimental allergic encephalomyelitis. Nat Protoc. 2006;1(4):1952-60.

Stumhofer et al., Interleukins 27 and 6 induce STAT3-mediated T cell production of interleukin 10. Nat Immunol. Dec. 2007;8(12):1363-71. Epub Nov. 11, 2007.

Suri-Payer et al., CD4+CD25+ T cells inhibit both the induction and effector function of autoreactive T cells and represent a unique lineage of immunoregulatory cells. J Immunol. Feb. 1, 1998;160(3):1212-8.

Sutmuller et al., Toll-like receptor 2 controls expansion and function of regulatory T cells. J Clin Invest. Feb. 2006;116(2):485-94. Epub Jan. 19, 2006.

Szu et al., Relation between structure and immunologic properties of the Vi capsular polysaccharide. Infect Immun. Dec. 1991;59(12):4555-61.

Tanaka et al., Human monocyte-derived dendritic cells induce naive T cell differentiation into T helper cell type 2 (Th2) or Th1/Th2 effectors. Role of stimulator/responder ratio. J Exp Med. Aug. 7, 2000;192(3):405-12.

Tang et al., Th type 1-stimulating activity of lung macrophages inhibits Th2-mediated allergic airway inflammation by an IFN-gamma-dependent mechanism. J Immunol. Feb. 1, 2001;166(3):1471-81.

Taurog et al., The germfree state prevents development of gut and joint inflammatory disease in HLA-B27 transgenic rats. J Exp Med. Dec. 1, 1994;180(6):2359-64.

(56) References Cited

OTHER PUBLICATIONS

Taylor et al., Stoichiometric depolymerization of polyuronides and glycosaminoglycuronans to monosaccharides following reduction of their carbodiimide-activated carboxyl groups. Biochemistry. Apr. 11, 1972;11(8):1383-8.

Teitelbaum et al., Immunomodulation of experimental autoimmune encephalomyelitis by oral administration of copolymer 1. Proc Natl Acad Sci U S A. Mar. 30, 1999;96(7):3842-7.

Teitelbaum et al., Specific inhibition of the T-cell response to myelin basic protein by the synthetic copolymer Cop 1. Proc Natl Acad Sci U S A. Dec. 1988;85(24):9724-8.

Teitelbaum et al., Synthetic copolymer 1 inhibits human T-cell lines specific for myelin basic protein. Proc Natl Acad Sci U S A. Jan. 1, 1992;89(1):137-41.

Teitelbaum et al., Unprimed spleen cell populations recognize macrophage-bound antigen with opposite net electric charge. Proc Natl Acad Sci U S A. Apr. 1977;74(4):1693-6.

Thomas et al., Randomized controlled trial of short bursts of a potent topical corticosteroid versus prolonged use of a mild preparation for children with mild or moderate atopic eczema. BMJ. 2002;324:1-7.

Tong et al., Mouse models of colorectal cancer. Chin J Cancer. Jul. 2011;30(7):450-62. doi: 10.5732/cjc.011.10041.

Tournoy et al., Endogenous interleukin-10 suppresses allergen-induced airway inflammation and nonspecific airway responsiveness. Clin Exp Allergy. Jun. 2000;30(6):775-83.

Toussirot et al., Bacterial extract (OM-89) specific and non specific immunomodulation in rheumatoid arthritis patients. Autoimmunity. Jun. 2006;39(4):299-306.

Triantafillidis et al., Colorectal cancer and inflammatory bowel disease: epidemiology, risk factors, mechanisms of carcinogenesis and prevention strategies. Anticancer Res. Jul. 2009;29(7):2727-37.

Troy et al., Beneficial effects of Bacteroides fragilis polysaccharides on the immune system. Front Biosci (Landmark Ed). Jan. 1, 2010;15:25-34.

Troy et al., Orientations of the Bacteroides fragilis capsular polysaccharide biosynthesis locus promoters during symbiosis and infection. J Bacteriol. Nov. 2010;192(21):5832-6. doi: 10.1128/JB.00555-10. Epub Aug. 20, 2010.

Turnbaugh et al., The human microbiome project. Nature. Oct. 18, 2007;449(7164):804-10.

Turnbaugh et al., An obesity-associated gut microbiome with increased capacity for energy harvest. Nature. Dec. 21, 2006;444(7122):1027-31.

Tzeng et al., Translocation and surface expression of lipidated serogroup B capsular Polysaccharide in Neisseria meningitidis. Infect Immun. Mar. 2005;73(3):1491-505.

Tzianabos, Polysaccharide Immunomodulators as Therapeutic Agents: Structural Aspects and Biologic Function, Clin. Microbiol. Rev. 13(4):523-533 (2000).

Tzianabos, et al., Polysaccharide-mediated protection against abscess formation in experimental intra-abdominal sepsis. J Clin. Invest. (1995) 96:2727-31.

Tzianabos, et al., Structural characteristics of polysaccharides that induce protection against intra-abdominal abscess formation. Infect Immun (1994) 62:4881-86.

Tzianabos et al., Bacterial structure and functional relation to abscess formation. Infect Agents Dis. Oct. 1994;3(5):256-65. Review.

Tzianabos et al., Characteristics of bacterial polysaccharides that activate T cells. The International Carbohydrate Symposium XVII. Jul. 21, 1994.

Tzianabos et al., Effect of surgical adhesion reduction devices on the propagation of experimental intra-abdominal infection. Arch Surg. Nov. 1999;134(11):1254-9.

Tzianabos et al., IL-2 mediates protection against abscess formation in an experimental model of sepsis. J Immunol. Jul. 15, 1999;163(2):893-7.

Tzianabos et al., Protection against experimental intraabdominal sepsis by two polysaccharide immunomodulators. J Infect Dis. Jul. 1998;178(1):200-6.

Tzianabos et al., Structural basis for polysaccharide-mediated protection against intraabdominal abscess formation. $94^{th}$ ASM General Meeting. May 23-27, 1994. Las Vegas, Nevada. Abstract B-206:65.

Tzianabos, et al., Structural rationale for the modulation of abscess formation by *Staphylococcus aureus* capsular polysaccharides. Proc Natl Acad Sci U S A. Jul. 31, 2001;98(16):9365-70. Epub Jul. 24, 2001.

Tzianabos et al., Structure and function of Bacteroides fragilis capsular polysaccharides: relationship to induction and prevention of abscesses. Clin Infect Dis. Jun. 1995;20 Suppl 2:S132-40. Review.

Tzianabos et al., Structure-function relationships for polysaccharide-induced intra-abdominal abscesses. Infect Immun. Aug. 1994;62(8):3590-3.

Tzianabos et al., T Cell Activation by Zwitterionic polysaccharides and peptide mimetics prevents antrabdominal abscess formation. Abstracts of the $99^{th}$ General Meeting of the American Society for Microbiology. Chicago, US: May 30-Jun. 3, 1999. Jun. 28, 1999;99:37-38.

Tzianabos et al., The capsular polysaccharide of Bacteroides fragilis comprises two ionically linked polysaccharides. J Biol Chem. Sep. 5, 1992;267(25):18230-5.

Tzianabos et al., T cells activated by zwitterionic molecules prevent abscesses induced by pathogenic bacteria. J Biol Chem. Mar. 10, 2000;275(10):6733-40.

Tzianabos et al., Structural features of polysaccharides that induce intra-abdominal abscesses. Science. Oct. 15, 1993;262(5132):416-9.

Uronis et al., Modulation of the intestinal microbiota alters colitis-associated colorectal cancer susceptibility. PLoS One. Jun. 24, 2009;4(6):e6026. doi: 10.1371/journal.pone.0006026.

Van Maren, Toll-like receptor signalling on Tregs: to suppress or not to suppress? Immunology. Aug. 2008;124(4):445-52. doi: 10.1111/j.1365-2567.2008.02871.x. Epub Jun. 28, 2008.

Van Scott et al., IL-10 reduces Th2 cytokine production and eosinophilia but augments airway reactivity in allergic mice. Am J Physiol Lung Cell Mol Physiol. Apr. 2000;278(4):L667-74.

Vann et al., The structure of the capsular polysaccharide (K5 antigen) of urinary-tract-infective *Escherichia coli* 010:K5:H4. A polymer similar to desulfo-heparin. Eur J Biochem. May 15, 1981;116(2):359-64.

Veldhoen et al., TGFbeta in the context of an inflammatory cytokine milieu supports de novo differentiation of IL-17-producing T cells. Immunity. Feb. 2006;24(2):179-89.

Velez et al., Type I *Streptococcus pneumoniae* carbohydrate utilizes a nitric oxide and MGC II-dependent pathway for antigen presentation. Immunol. 2008;127:73-82. doi: 10.1111/j.1365-2567.2008.02924.x.

Verdu et al., Oral administration of antigens from intestinal flora anaerobic bacteria reduces the severity of experimental acute colitis in BALB/c mice. Clin Exp Immunol. Apr. 2000;120(1):46-50.

Videla et al., Role of intestinal microflora in chronic inflammation and ulceration of the rat colon. Gut. Aug. 1994;35(8):1090-7.

Vignali et al., How regulatory T cells work. Nat Rev Immunol. Jul. 2008;8(7):523-32. doi: 10.1038/nri2343.

Vinderola et al., Effects of the oral administration of the exopolysaccharide produced by Lactobacillus kefiranofaciens on the gut mucosal immunity. Cytokine. Dec. 2006;36(5-6):254-60. Epub Mar. 23, 2007.

Viret et al., Molecular cloning and characterization of the genetic determinants that express the complete Shigella serotype D (*Shigella sonnei*) lipopolysaccharide in heterologous live attenuated vaccine strains. Mol Microbiol. Jan. 1993;7(2):239-52.

Wagner et al., Use of reporter cells to study endogenous retinoid sources in embryonic tissues. Methods Enzymol. 1997;282:98-107.

Wang et al., A bacterial carbohydrate links innate and adaptive responses through Toll-like receptor 2. J Exp Med. Dec. 25, 2006;203(13):2853-63. Epub Dec. 18, 2006.

Wang et al., Lipopolysaccharide: Biosynthetic pathway and structure modification. Prog Lipid Res. Apr. 2010;49(2):97-107. doi: 10.1016/j.plipres.2009.06.002. Epub Oct. 6, 2009.

(56) References Cited

OTHER PUBLICATIONS

Wang et al., Ozonolysis for selectively depolymerizing polysaccharides containing β-d-aldosidic linkages. Proc Natl Acad Sci U S A. Jun. 9, 1998; 95(12): 6584-6589.
Wang et al., Structural basis of the abscess-modulating polysaccharide A2 from Bacteroides fragilis. Proc Natl Acad Sci U S A. Dec. 5, 2000;97(25):13478-83.
Wang et al., Structure characterization of an abscessogenic capsular polysaccharide from Bacteriodes fragilis by NMR spectroscopy. XIX International Conference of NMR in Biological Systems. Florence, Italy. Aug. 20-25, 2000. Abstract.
Ward et al., The nucleotide sequence of the tnpA gene of Tn21, Nucleic Acids Research, vol. 15(4), 1987, 1799-1806.
Wehr et al., Anti-low-density lipoprotein antibodies in alcoholics without and with liver disease and in social drinkers. Alcohol Alcohol. Jan.-Feb. 1997;32(1):43-9.
Weinacht et al. Phase variation of the capsular polysaccharides of Bacteroides fragilis is dictated by site-specific recombinases. 2002 General Meeting of the American Society for Microbiology, May 19-23, 2002. Abstract.
Weintraub et al., Structural characterization of the lipid A component of Bacteroides fragilis strain NCTC 9343 lipopolysaccharide. Eur J Biochem. Aug. 1, 1989;183(2):425-31.
Wen et al., Innate immunity and intestinal microbiota in the development of Type 1 diabetes. Nature. Oct. 23, 2008;455(7216):1109-13. doi: 10.1038/nature07336. Epub Sep. 21, 2008.
Wessels et al., Structural Determination and Immunochemical Characterization of the Type V Group B *Streptococcus* Capsular Polysaccharide, The Journal of Biological Chemistry, 266:6714-6719, 1991.
Wessels et al., Structure and immunochemistry of an oligosaccharide repeating unit of the capsular polysaccharide of type III group B *Streptococcus*. A revised structure for the type III group B *streptococcal* polysaccharide antigen. J Biol Chem. Jun. 15, 1987;262(17):8262-7.
Wexler, Bacteroides: the good, the bad, and the nitty-gritty. Clin Microbiol Rev. Oct. 2007;20(4):593-621.
Whitfield, Biosynthesis and assembly of capsular polysaccharides in *Escherichia coli*. Annu Rev Biochem. 2006;75:39-68.
Wiegandt et al., Carbohydrate Components of Extraneuronal Gangliosides from Bovine and Human Spleen, and Bovine Kidney, European Journal of Biochemistry, 15:287-292, 1970.
Willer et al., Twin concordance and sibling recurrence rates in multiple sclerosis. Proc Natl Acad Sci U S A. Oct. 28, 2003;100(22):12877-82. Epub Oct. 20, 2003.
Wirtz et al., Mouse models of inflammatory bowel disease. Adv Drug Deliv Rev. Sep. 30, 2007;59(11):1073-83. Epub Aug. 16, 2007.
Woessner et al., Long-term antibiotic treatment with roxithromycin in patients with multiple sclerosis. Infection. Dec. 2006;34(6):342-4.
Wong et al., Activation of peripheral Th17 lymphocytes in patients with asthma. Immunol Invest. 2009;38(7):652-64.
Woodruff et al., Sudden-onset severe acute asthma: clinical features and response to therapy. Acad Emerg Med. Jul. 1998;5(7):695-701.
Wu et al., Gut-residing segmented filamentous bacteria drive autoimmune arthritis via T helper 17 cells. Immunity. Jun. 25, 2010;32(6):815-27. doi: 10.1016/j.immuni.2010.06.001.
Wujek et al., A carbohydrate polymer that effectively prevents epidural fibrosis at laminectomy sites in the rat. Exp Neurol. Nov. 1991;114(2):237-45.
Xavier et al., Commensal flora: wolf in sheep's clothing. Gastroenterology. Apr. 2005;128(4):1122-6.
Xavier et al., Unravelling the pathogenesis of inflammatory bowel disease. Nature. Jul. 26, 2007;448(7152):427-34.
Xie et al., Cancer in inflammatory bowel disease. World J Gastroenterol. Jan. 21, 2008;14(3):378-89.
Xu J et al., A genomic view of the human-Bacteroides thetaiotaomicron symbiosis. Science. Mar. 28, 2003;299(5615):2074-6.
Yamazaki et al., CCR6 regulates the migration of inflammatory and regulatory T cells. J Immunol. Dec. 15, 2008;181(12):8391-401.
Yamazaki et al., Dendritic cells are specialized accessory cells along with TGF—for the differentiation of Foxp3+ CD4+ regulatory T cells from peripheral Foxp3 precursors. Blood. Dec. 15, 2007;110(13):4293-302. Epub Aug. 15, 2007.
Yokoyama et al., Adhesion behavior of rat lymphocytes to poly(ether)-poly(amino acid) block and graft copolymers. J Biomed Mater Res. Sep. 1986;20(7):867-78.
Yoshii, Cytotoxic effects of acrylates and methacrylates: relationships of monomer structures and cytotoxicity. J Biomed Mater Res. Dec. 15, 1997;37(4):517-24.
Young et al., In vitro and in vivo characterization of Helicobacter hepaticus cytolethal distending toxin mutants. Infect Immun. May 2004;72(5):2521-7.
Zabad et al., The clinical response to minocycline in multiple sclerosis is accompanied by beneficial immune changes: a pilot study. Mult Scler. May 2007;13(4):517-26. Epub Feb. 9, 2007.
Zaleznik et al., A soluble suppressor T cell factor protects against experimental intraabdominal abscesses. J Clin Invest. Mar. 1985;75(3):1023-7.
Zaph et al., Commensal-dependent expression of IL-25 regulates the IL-23-IL-17 axis in the intestine. J Exp Med. Sep. 29, 2008;205(10):2191-8. doi: 10.1084/jem.20080720. Epub Sep. 1, 2008.
Zehnder et al., Extrarenal expression of 25-hydroxyvitamin d(3)-1 alpha-hydroxylase. J Clin Endocrinol Metab. Feb. 2001;86(2):888-94.
Zehnder et al., Expression of 25-hydroxyvitamin D3-1alpha-hydroxylase in the human kidney. J Am Soc Nephrol. Dec. 1999;10(12):2465-73.
Zhang et al., Degradation of Wood Polysaccharide Model Compounds During Ozone Treatment. Journal of Pulp and Paper Science. Jan. 1997;23(1):J23-J27.
Zhang et al., IL-10 is involved in the suppression of experimental autoimmune encephalomyelitis by CD25+CD4+ regulatory T cells. Int Immunol. Feb. 2004;16(2):249-56.
Zhao H et al. In vivo phase variation of MR/P fimbrial gene expression in Proteus mirabilis infecting the urinary tract. (1997) Mol Microbiol 23:1009-19.
Zhou et al., TGF-beta-induced Foxp3 inhibits T(H)17 cell differentiation by antagonizing RORgammat function. Nature. May 8, 2008;453(7192):236-40. doi: 10.1038/nature06878. Epub Mar. 26, 2008.
Zhu et al., Oral administration of type-II collagen peptide 250-270 suppresses specific cellular and humoral immune response in collagen-induced arthritis. Clin Immunol. Jan. 2007;122(1):75-84. Epub Oct. 11, 2006.
Geva-Zatorsky et al., Mining the Human Gut Microbiota for Immunomodulatory Organisms. Cell. Feb. 23, 2017;168(5):928-943.e11. doi: 10.1016/j.cell.2017.01.022. Epub Feb. 16, 2017.
U.S. Appl. No. 10/432,406, filed Nov. 20, 2003, Granted, U.S. Pat. No. 7,629,330.
U.S. Appl. No. 12/470,985, filed May 22, 2009, Granted, U.S. Pat. No. 8,008,276.
U.S. Appl. No. 10/814,620, filed Mar. 31, 2004, Abandoned, 2004-0219160.
U.S. Appl. No. 12/754,948, filed Apr. 6, 2010, Abandoned, 2011-0059125.
U.S. Appl. No. 13/316,744, filed Dec. 12, 2011, Abandoned, 2012-0315264.
U.S. Appl. No. 14/043,876, filed Oct. 2, 2013, Granted, U.S. Pat. No. 9,265,790.
U.S. Appl. No. 12/223,563, filed Apr. 3, 2009, Granted, U.S. Pat. No. 8,206,726.
U.S. Appl. No. 13/493,512, filed Jun. 11, 2012, Abandoned, 2012-0309955.
U.S. Appl. No. 14/131,812, filed Apr. 7, 2014, Granted, 2014-0243285.
U.S. Appl. No. 15/753,129, filed Feb. 15, 2018, Published, 2019-0046560.
EP17828599.5, Feb. 19, 2020, Extended European Search Report.

(56) References Cited

OTHER PUBLICATIONS

PCT/US2017/042282, Jan. 24, 2019, International Preliminary Report on Patentability.
PCT/US2017/042282, Oct. 2, 2017, International Search Report and Written Opinion.
U.S. Appl. No. 15/753,129, filed Feb. 15, 2018, Granted, 2019-0046560.
U.S. Appl. No. 17/088,547, filed Nov. 3, 2020, Published, 2021-0315923.
Chandler et al., Bacterial lipids: powerful modifiers of the innate immune response. F1000Res. Aug. 7, 2017;6:F1000 Faculty Rev-1334, doi: 10.12688/f1000research.11388.1.

* cited by examiner

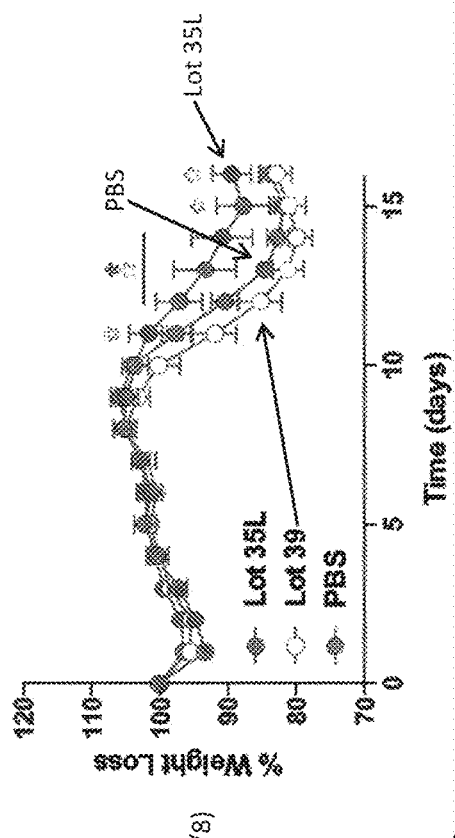
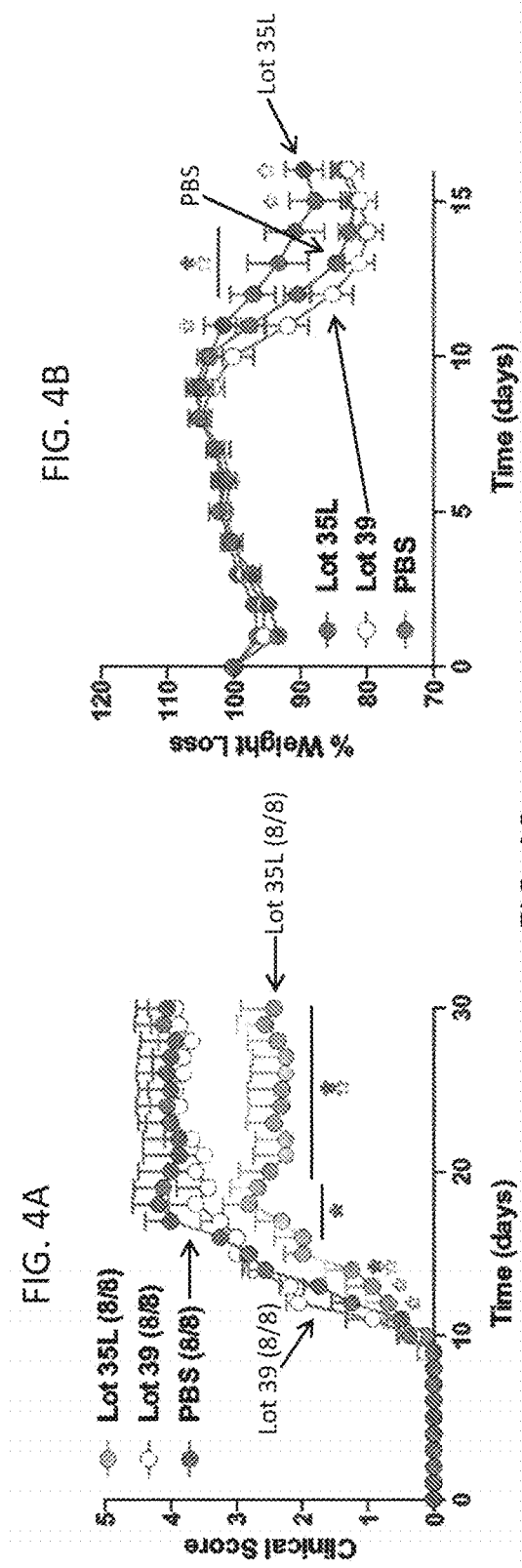
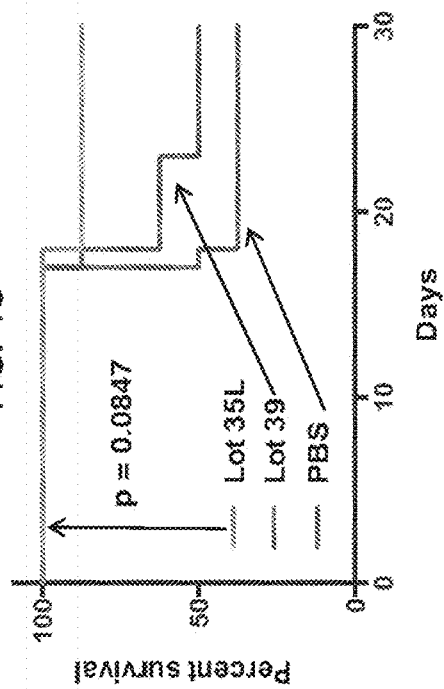

GLYCOLIPID COMPOSITIONS AND METHODS OF USE

CROSS-REFERENCE TO RELATED APPLICATIONS

This application is a national stage filing under 35 U.S.C. § 371 of International Application No. PCT/US2017/042282, filed Jul. 15, 2017, published under PCT Article 21(2) in English, and which claims the benefit under 35 U.S.C. § 119(e) of U.S. Provisional Application No. 62/362,630, entitled "GLYCOLIPID COMPOSITIONS AND METHODS OF USE," filed Jul. 15, 2016, the entire contents of each of which are incorporated by reference herein.

FIELD

The invention relates to glycolipids, compositions, methods of synthesis, isolation and/or purification, and methods of use thereof.

BACKGROUND

Polysaccharide A (PSA) of *Bacteroides fragilis* (*B. fragilis*) has been reported to be an immunomodulator with therapeutic and prophylactic activities. U.S. Pat. Nos. 5,679,654 and 5,700,787; Tzianabos A O et al. (2000) J Biol Chem 275:6733-40. As an example, PSA has been shown to provide protection from intestinal inflammatory diseases as well as systemic immune-mediated diseases such as the mouse model for multiple sclerosis, experimental autoimmune encephalomyelitis (EAE). PSA is one of eight capsular polysaccharides made by *B. fragilis*.

PSA was recently discovered to possess a lipid moiety. The lipid moiety was hypothesized to anchor the polysaccharide in the *B. fragilis* outer membrane. It was also recently discovered that this "lipidated PSA" was more potent than non-lipidated PSA (referred to herein as "PSA") forms provided in the prior art.

SUMMARY

The invention is based, in part, on the identification and characterization of the glycolipid moiety that is found conjugated to PSA using certain isolation methods. The invention is further premised, in part, on surprising finding that such glycolipid is able to stimulate the innate immune response and in particular activate antigen-presenting cells such as plasmacytoid dendritic cells. Based on this surprising finding, this disclosure contemplates and provides, among other things, use of the glycolipids as adjuvants in for example vaccine formulations.

The innate immunostimulatory property of the glycolipid is enhanced upon cleavage of the glycolipid moiety from the polysaccharide chain of PSA.

The disclosure therefore provides, in some aspects, glycolipids of defined chemical structure, as well as compositions comprising such glycolipids. Such compositions may be further defined by the purity and/or concentration of glycolipids contained therein.

Also provided are compositions of the glycolipids with antigens such as but not limited to bacterial antigens, including without limitation PSA and lipidated PSA. In some instances, such compositions comprise lipidated PSA and glycolipid in ratios ranging from 4:1 to 20:1 (w/w), or 4:1 to 15:1 (w/w), or 4:1 to 10:1 (w/w).

In one aspect, provided herein is a glycolipid comprising a tri-acylated, tetra-acylated or penta-acylated diglucosamine, and the diglucosamine may be optionally conjugated to an oligosaccharide. The glycolipid may be isolated intending that it is physically separated from other components including contaminants such as but not limited to components of *B. fragilis* cells. Isolation may also intend a degree of purity or concentration in a composition. The glycolipid unless otherwise stated is unconjugated to the polysaccharide chain of PSA (i.e., the polysaccharide comprised of repeating tetrasaccharides found in PSA and lipidated PSA). Thus, it is to be understood that if the acylated diglucosamine is conjugated to the oligosaccharide, such oligosaccharide is not the PSA polysaccharide, and such glycolipid is not PSA. The glycolipid may be formulated with such polysaccharide chain of PSA or it may be formulated with lipidated PSA or it may be formulated with another antigen or another polysaccharide bearing moiety, although it will typically be provided in an unconjugated or free form. Examples of such formulations include for example micelles or liposomes or other delivery vehicles that are amenable to lipid based agents.

In some embodiments, the diglucosamine is tetra-acylated or penta-acylated. In some embodiments, the tri-acylated, tetra-acylated or penta-acylated diglucosamine comprises acyl chains ranging in length from 14-17 carbons. In some embodiments, the tri-acylated, tetra-acylated or penta-acylated diglucosamine comprises acyl chains range in length from 15-17 carbons.

In some embodiments, the glycolipid is substantially free of other components found in a *B. fragilis* capsule or found in *B. fragilis* cells. In some embodiments, the glycolipid is substantially free of LPS. In some embodiments, the glycolipid is substantially free of polysaccharide including for example the repeating tetrasaccharide polysaccharide of PSA.

In some embodiments, the glycolipid is provided in purified form. In some embodiments, the glycolipid is provided an isolated form. In some embodiments, the glycolipid is provided in a micelle form or a liposome form, alone or optionally with other agents such as antigens, polysaccharides and the like. In some embodiments, the glycolipid is provided in a lyophilized form. Lyophilized forms glycolipid are particularly suitable for long-term storage, ranging from days, weeks, months or even years. In some embodiments, the glycolipid is provided in a form that is suitable for administration to a human, including an orally administered form or a parenterally administered form.

In some embodiments, the glycolipid is obtained or derived from *B. fragilis* cells, including *B. fragilis* cells that overexpress PSA relative to polysaccharide B (PSB), PSC, PSD, PSE, PSF, PSG and PSH. As used herein, obtained or derived intends that the glycolipid that is defined structurally herein is rendered using the isolation methods provided herein. It does not however intend that any naturally occurring counterpart of the glycolipid is structurally identical to the structure defined herein.

In some embodiments, at least one acyl chain is unmodified. In some embodiments, at least one acyl chain is modified, for example modified with a hydroxyl group. In some embodiments, at least one acyl chain is unmodified and at least one of the acyl chains is modified, for example modified with a hydroxyl group. In some embodiments, at least one acyl chain is modified with a hydroxyl group. In some embodiments, at least one acyl chain is C16:0-OH. In some embodiments, at least one acyl chain is C17:0-OH. In some embodiments, at least one acyl chain is C14:0. In some embodiments, at least one acyl chain is C15:0.

In some embodiments, at least one acyl chain is N-substituted. In some embodiments, at least one acyl chain is O-substituted. In some embodiments, at least one acyl chain is N-substituted and at least one acyl chain is O-substituted. In some embodiments, all of the acyl chains are N-substituted or all of the acyl chains are O-substituted.

In some embodiments, the diglucosamine is phosphorylated. In some embodiments, the diglucosamine is monophosphorylated. In some embodiments, the diglucosamine is not phosphorylated.

In some embodiments, the diglucosamine is conjugated to the oligosaccharide by an acid-labile bond. In some embodiments, the acid-labile bond is a ketosidic bond.

In some embodiments, the oligosaccharide comprises or contains 3-10 sugars (e.g., it may comprise 3 or more sugars). The oligosaccharide however is not the polysaccharide of PSA (i.e., it is not the zwitterionic tetrasaccharide moiety or repeated moiety shown in FIG. 1). In some embodiments, the oligosaccharide contains 2-10, 2-9, 3-9, 4-9, 5-9, 6-9, 7-9 or 8-9 sugars. In some embodiments, the oligosaccharide contains 6-9 sugars. In some embodiments, the oligosaccharide comprises galactose and/or glucose and/or fucose residues. Thus, the sugars of the oligosaccharide may be identical or different from each other.

In some embodiments, the oligosaccharide comprises one or two KDO residues. The oligosaccharide is not and does not comprise the repeating tetrasaccharide units of PSA.

In some embodiments, the glycolipid is formulated with a detergent or a bile salt. In some embodiments, the detergent or bile salt is present at or less than 1%, 0.5% or 0.1% (weight of detergent or bile salt/weight of glycolipid).

In some embodiments, the glycolipid is formulated with an antigen other than a lipidated PSA or a component of such lipidated PSA.

In some embodiments, the glycolipid is formulated with vaccine additives.

In some embodiments, the glycolipid is formulated with a non-naturally occurring preservative. In some embodiments, the glycolipid is formulated with a non-naturally occurring stabilizer. In some embodiments, the glycolipid is formulated with human albumin, phenol, glycerin or glycine.

In some embodiments, the glycolipid is formulated with thimerosal, aluminum hydroxide, benzethonium chloride, formaldehyde, formalin, glutaraldehyde, potassium phosphate, aluminum potassium sulfate, bovine extract, calf serum, ammonium sulfate, aluminum phosphate, non-human cells, Vero (monkey kidney) cells, human cells, MRC-5 (human diploid) cells, MRC-5 cellular proteins, and the like.

In some embodiments, the glycolipid is formulated for parenteral administration. In some embodiments, the glycolipid is formulated for oral administration.

Thus, also provided herein are compositions comprising any of the foregoing glycolipids. In some embodiments, the composition further comprises an antigen other than a lipidated PSA or a component of such lipidated PSA. In some embodiments, the composition comprises any of the foregoing glycolipids and lipidated PSA in non-naturally occurring weight/weight ratios such as but not limited to 1:75, 1:50, 1:25, 1:20, 1:10, 1:5, and the like.

In some embodiments, the composition further comprises a detergent or a bile salt. In some embodiments, the detergent or bile salt is present at or less than 1%, 0.5% or 0.1% (weight of detergent or bile salt/weight of glycolipid).

In some embodiments, the composition further comprises vaccine additives.

In some embodiments, the composition further comprises a non-naturally occurring preservative. In some embodiments, the composition further comprises a non-naturally occurring stabilizer. In some embodiments, the composition further comprises human albumin, phenol, glycerin or glycine.

In some embodiments, the composition further comprises thimerosal, aluminum hydroxide, benzethonium chloride, formaldehyde, formalin, glutaraldehyde, potassium phosphate, aluminum potassium sulfate, bovine extract, calf serum, ammonium sulfate, aluminum phosphate, non-human cells, Vero (monkey kidney) cells, human cells, MRC-5 (human diploid) cells, MRC-5 cellular proteins, and the like.

In some embodiments, any of the foregoing glycolipids or compositions is formulated for parenteral administration. In some embodiments, any of the foregoing glycolipids or compositions is formulated for oral administration.

Also provided herein is a composition comprising a lipidated polysaccharide A (PSA) and any of the foregoing glycolipids in a 4:1 to 20:1 ratio (w/w).

Also provided herein is a composition comprising a lipidated polysaccharide A (PSA) and at least 0.5% (w/w) of any of the foregoing glycolipids.

In some embodiments, the composition further comprises a pharmaceutically acceptable carrier.

In some embodiments, the composition further comprises another therapy such as an additional active agent or it is formulated for administration in combination with another therapy such as an additional active agent. In some embodiments, the other therapy is or comprises a cancer immunotherapy. In some embodiments, the cancer immunotherapy comprises administration of an antibody or antibody fragment thereof.

In some embodiments, the composition is formulated for parenteral administration. In some embodiments, the composition is formulated for oral administration.

Also provided herein is a composition comprising any one of the foregoing glycolipids and an antigen. In some embodiments, the composition is a vaccine.

In some embodiments, the antigen is a bacterial antigen. In some embodiments, the antigen is attenuated bacteria. In some embodiments, the antigen is a viral antigen. In some embodiments, the antigen is attenuated virus. In some embodiments, the antigen is a fungal antigen. In some embodiments, the antigen is a mycobacterial antigen. In some embodiments, the antigen is a parasitic antigen. In some embodiments, the antigen is a cancer antigen. In some embodiments, the antigen is a human protein. In some embodiments, the antigen is a human polysaccharide. In some embodiments, the composition is formulated for parenteral administration.

Also provided herein is a method of enhancing an innate immune response comprising administering, to a subject in need of an immune response, such as an enhanced immune response, and further such as an enhanced innate immune response, an effective amount of any of the foregoing glycolipids.

In some embodiments, the method further comprises administering a lipidated PSA in combination with another therapy. In some embodiments, the other therapy is or comprises a cancer immunotherapy. In some embodiments, the cancer immunotherapy comprises administration of an antibody or antibody fragment thereof.

Also provided herein is a method of inducing an immune response comprising administering, to a subject in need of immune response induction or modulation, an effective amount of any of the foregoing glycolipids.

In some embodiments, the method further comprises administering a lipidated PSA in combination with another therapy. In some embodiments, the other therapy is or comprises a cancer immunotherapy. In some embodiments, the cancer immunotherapy comprises administration of an antibody or antibody fragment thereof.

In some embodiments, the immune response is an innate immune response. In some embodiments, the immune response is an adaptive immune response.

Also provided herein is a method of inducing an immune response comprising administering, to a subject in need of immune response induction or modulation, an effective amount of any of the foregoing glycolipids, wherein the immune response comprises induction of interferon-beta, and the subject is experiencing or is likely to experience an interferon-beta responsive condition (e.g., a condition that has been shown to benefit from administration of exogenous interferon-beta and/or that can benefit from induction of interferon-beta in vivo). Such conditions include but are not limited to any of the autoimmune diseases provided herein. In some embodiments, the condition is multiple sclerosis (MS). In some embodiments, the condition is systemic lupus erythematosus.

Also provided herein is a method of inducing an immune response to an antigen comprising administering, to a subject in need of an antigen-specific immune response, an effective amount of any of the foregoing glycolipid and the antigen.

In some embodiments, the subject has or is at risk of developing a bacterial infection. In some embodiments, the antigen is a bacterial antigen. In some embodiments, the antigen is attenuated bacteria.

In some embodiments, the subject has or is at risk of developing a viral infection. In some embodiments, the antigen is a viral antigen. In some embodiments, the antigen is attenuated virus.

In some embodiments, the subject has or is at risk of developing a fungal infection. In some embodiments, the antigen is a fungal antigen.

In some embodiments, the subject has or is at risk of developing a mycobacterial infection. In some embodiments, the antigen is a mycobacterial antigen.

In some embodiments, the subject has or is at risk of developing a parasitic infection. In some embodiments, the antigen is a parasitic antigen.

In some embodiments, the subject has or is at risk of developing a cancer. In some embodiments, the antigen is a cancer antigen.

In some embodiments, the antigen is a human protein. In some embodiments, the antigen is a human polysaccharide.

In some embodiments, the method further comprises administering to the subject lipidated PSA.

Also provided herein is a micelle consisting essentially of any one or any combination of the foregoing glycolipids.

Also provided herein is a composition comprising a micelle consisting essentially of any one or any combination of the foregoing glycolipids and a detergent or bile salt. In some embodiments, the detergent or bile salt is present in a pharmaceutically acceptable amount. In some embodiments, the composition is a pharmaceutical composition. In some embodiments, formulated for parenteral administration.

In various embodiments, the glycolipid is free of non-lipidated PSA. In various embodiments, the glycolipid is free of lipidated PSA.

In various embodiments, the glycolipid is suitable for administration to a human.

In various embodiments, the composition is formulated for parenteral or enteral or oral administration to a subject. In various embodiments, the composition is formulated for lipophilic delivery, including for example in a liposome or in an oil-based delivery system. The various compositions provided herein may be formulated as a capsule or other discrete dosage form, including those intended for oral or enteral administration.

In another aspect, the invention provides an isolated glycolipid comprising a diglucosamine covalently conjugated to 3-5 acyl chains, each independently ranging in length from 14-17 carbons. The glycolipid may be any of the glycolipids provided herein, or a combination thereof. In various embodiments, the diglucosamine is covalently conjugated to 3-5 acyl chains. In various embodiments, the diglucosamine is covalently conjugated to 4 or 5 acyl chains. In various embodiments, the acyl chains range in length from 15-17 carbons. Other embodiments relating to the glycolipids are recited above and apply equally. It is to be understood that any of the aspects and embodiments described herein relating to glycolipids, including compositions and methods of use, embrace and contemplate glycolipids that comprise, consist or consist essentially of a disaccharide, such as a diglucosamine, covalently conjugated to 3-5 acyl chains, and optionally each chain may independently range in length from 4-17 carbons.

In another aspect, the invention provides a method comprising administering to a subject in need of immune response modulation a composition comprising a lipidated polysaccharide A (PSA) and any of the foregoing glycolipids in an effective amount.

In another aspect, the invention provides a method comprising administering to a subject in need of immune response modulation an effective amount of a composition comprising a lipidated polysaccharide A (PSA) and any of the foregoing glycolipids, in combination with an additional therapy.

In another aspect, the invention provides a method comprising administering to a subject in need of immune response modulation one or both of a composition comprising a lipidated polysaccharide A (PSA) and any of the foregoing glycolipids; and another therapy, so that the subject receives therapy with the composition and the other therapy in combination.

In some embodiments, the subject has or is at risk of developing cancer. In some embodiments, the subject is diagnosed as suffering from, susceptible to, and/or receiving therapy for cancer.

In some embodiments, the additional therapy is or comprises a cancer immunotherapy. In some embodiments, the cancer immunotherapy is or comprises an antibody or antibody fragment thereof.

In some embodiments, the step of administering comprises administering according to a regimen that has been demonstrated to achieve statistically significant improvement in immune function when administered to a relevant population of subjects. The relevant population of subjects may comprise subjects diagnosed as suffering from, susceptible to, and/or receiving therapy for cancer. In some embodiments, the improvement in immune function comprises modulation of an innate and/or adaptive immune response.

In some embodiments, the subject in need of immune response modulation is a subject in need of innate immune response modulation. In some embodiments, the subject in need of immune response modulation is a subject in need of adaptive immune response modulation. In some embodiments, the subject in need of immune response modulation is a subject in need of immune response stimulation.

In some embodiments, improvement in immune function comprises stimulation of an innate and/or adaptive immune response.

In some embodiments, the step of administering comprises administering an amount of the composition effective to achieve an improvement in immune function as compared to a subject who has not been administered the composition.

In some aspects, the acylated diglucosamine, such as but not limited to the tetra-acylated diglucosamine or the penta-acylated diglucosamine, may be administered to a subject experiencing or likely to experience a proinflammatory immune response, such as may occur for example during an E. coli infection or an infection by gram negative bacteria. The acylated diglucosamine may be conjugated to an oligosaccharide such as 3-10-mer oligosaccharide. The subject may be defined as one experiencing or likely to experience a gram negative bacterial infection, including but not limited to infection by any of the gram negative bacterial species provided herein.

It is to be understood that various foregoing aspects and embodiments overlap. It is intended that the embodiments recited above apply equally to the various aspects recited above.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE FIGURES

It is to be understood that the Figures are not necessarily to scale, emphasis instead being placed upon generally illustrating the various concepts discussed herein.

FIGS. 4A-4C show that PSA with higher levels of GLA provides better protection in an EAE model than PSA alone. The Figures show that a preparation comprising lipidated PSA and GLA (at an approximately 4:1 ratio, w/w, referred to herein as Lot 35L) protects in an EAE model system better than purified lipidated PSA lacking any free glycolipid (Lot 39). C57BL/6 mice were orally administered purified lipidated PSA (Lot 39), or a preparation comprising lipidated PSA and "free" GLA (Lot 35L), or PBS every other day starting from one week before inducing the disease. Mice were challenged subcutaneously with MOG 35-55 in Complete Freund's Adjuvant. On days 0 and 2 after challenge, the mice received intraperitoneal Bordetella pertussis toxin. Mice were monitored and scored daily for disease progression. FIG. 4A shows the clinical EAE score of the mice, with a score of 5 indicating death. FIG. 4B shows the % weight loss of the mice. Significance of the results using Lot 35L to Lot 39 or to PBS is indicated by white asterisks (Lot 39 (8/8) and grey asterisks (PBS (8/8)), respectively. FIG. 4C shows the percent survival of the mice. Lot 35L, which contains more free GLA as compared to Lot 39, reduced the severity of the disease and the cumulative disease score, and increased survival rate of the mice. The presence of free GLA enhanced the protective activity of lipidated PSA.

FIG. 6A shows the clinical EAE score of mice subjected to MOG-peptide induced EAE ($p<0.01$). Significance of the results using Lot 39 and GL together compared to GLA alone or Lot 39 alone is indicated by asterisks and circled asterisks (Lot 39), respectively, in FIG. 6A. FIG. 6B shows the % weight loss in the mice ($p<0.05$). FIG. 6C shows the percent survival of the mice. GLA alone failed to confer protection, while a reconstituted mixture of purified lipidated PSA and GLA (at a 4:1 w/w ratio) protected animals from EAE. FIG. 6D shows the cumulative disease scores calculated as the sum of all EAE clinical scores for each group.

FIG. 7A shows the clinical EAE score of mice subjected to MOG-peptide induced EAE ($p=0.001$ on day 15). FIG. 7B shows the cumulative scores calculated as the sum of all EAE clinical scores for each group. Delipidated PSA35 failed to confer protection, while PSA35 protected animals from EAE indicating the importance of the glycolipid in such protection. In these experiments, on the order of about 10 micrograms of the PSA35 preparation was administered per mouse, representing about 8 micrograms of lipidated PSA and about 2 micrograms of GLA. This amount was about 10-fold lower than the amounts used in the experiments of the preceding Figures.

DETAILED DESCRIPTION

Figure 1:
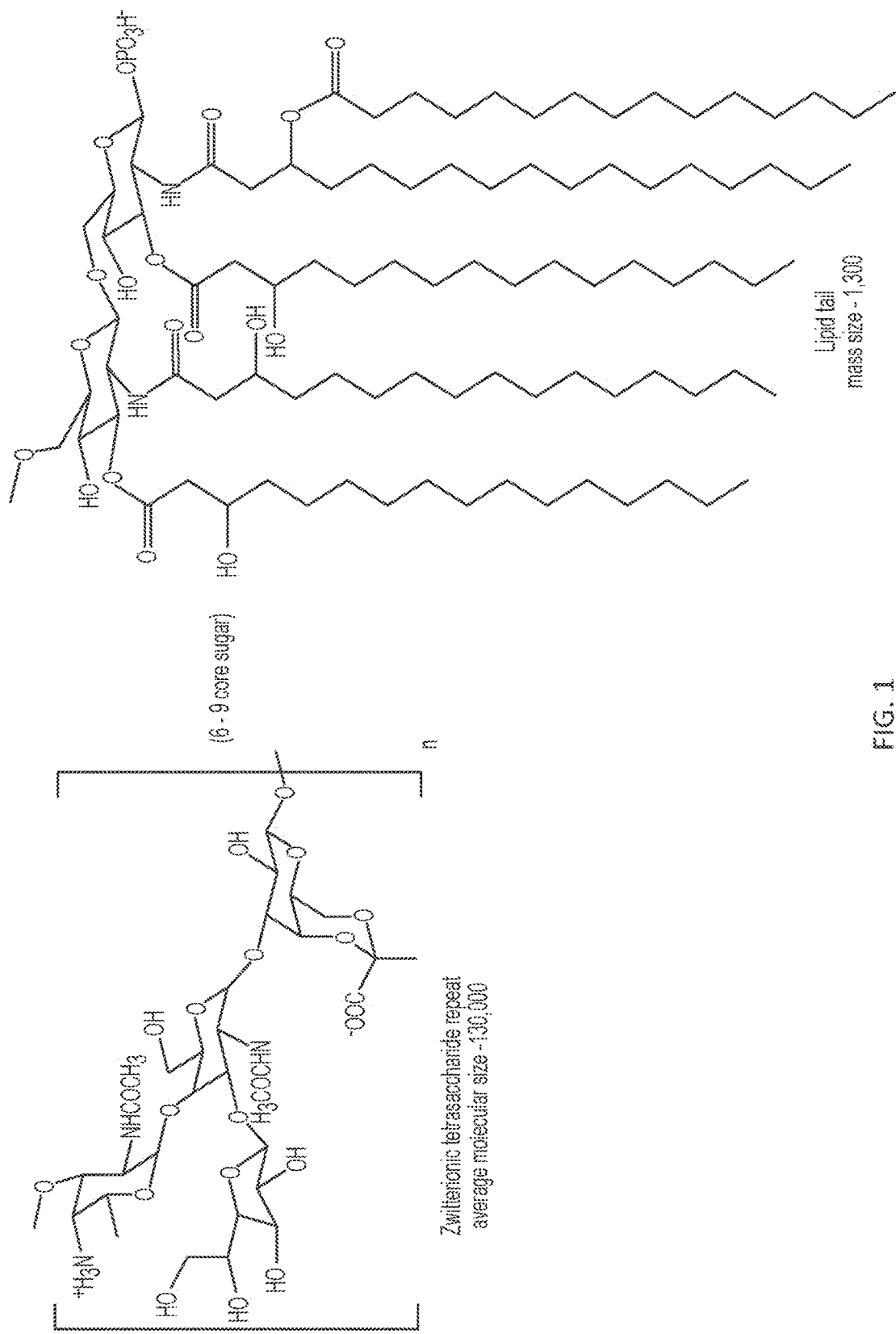
FIG. 1 is a proposed generic structure of isolated B. fragilis lipidated PSA. The structure includes a repeating tetrasaccharide unit having an average molecular weight of about 130 KDa, an oligosaccharide core unit comprising on average less 10 or fewer sugar residues, and a glycolipid. The glycolipid may comprise 3-5 acyl chains that may be N or O linked to a diglucosamine. The diglucosamine may be monophosphorylated or non-phosphorylated.

Provided herein are compositions and methods of use relating to a glycolipid antigen comprising a diglucosamine-containing glycolipid. The glycolipid antigen, referred to herein as GLA, minimally comprises a diglucosamine-containing glycolipid. The diglucosamine moiety may be monophosphorylated or non-phosphorylated (e.g., dephosphorylated). The glycolipid may comprise 3-5 acyl chains that are N- or O-linked to the diglucosamine.

The glycolipid may further be conjugated to an oligosaccharide, referred to herein as an oligosaccharide core unit. Such oligosaccharide may comprise 10 or fewer sugars. The sugars may be galactose, glucose and/or fucose. The oligosaccharides are typically conjugated to the diglucosamine via an acid-labile linkage such as but not limited to a ketosidic linkage.

Significantly, it has now been discovered, surprisingly, that the glycolipid is able to stimulate an innate immune response. This activity has been heretofore unrecognized. The finding is significant since it indicates that lipidated PSA is able to stimulate both innate and adaptive immune responses via different portions of its structure. Even more surprising is that free glycolipid, when combined with lipidated PSA, leads to enhanced protective activity in EAE mouse models. This suggests that free glycolipid is able to enhance immune responses to a greater degree than possible when used in its conjugated form. This disclosure provides methods of use of this glycolipid as an adjuvant together with PSA, whether or not lipidated, as well as a variety of other antigens. This newly discovered adjuvant activity indicates a role of the glycolipid in enhancing innate immunity, including when used alone, as well as in enhancing adaptive immunity when used together with an antigen. Examples of this latter application include use as an adjuvant for vaccines, and well as in immuno-oncology.

The glycolipid has been obtained from manipulation of *B. fragilis* cells. The starting material was a non-naturally, mutant occurring strain of *B. fragilis* that overexpresses PSA but not other capsular polysaccharides. The purification protocol may include a phenol/water extraction, and DNAse, RNase and pronase treatments. If the material is then treated with deoxycholate (DOC), the glycolipid comprising the oligosaccharide core unit is obtained. DOC treatment therefore separates the glycolipid from lipidated PSA. If however the material is treated instead with acid hydrolysis, the acid-labile linkage between the oligosaccharide core unit and the acyl-substituted diglucosamine is cleaved and the free acyl-substituted diglucosamine is obtained. If instead a purification is performed that does not involve either DOC treatment or acid hydrolysis (e.g., column chromatography), then the resulting preparation comprises about 20% (w/w) free glycolipid and about 80% (w/w) PSA including lipidated PSA. One such preparation is used in the experiments described herein, and is referred to as 35L or PSA35L or Lot 35L. As used herein, a "free" glycolipid refers to a glycolipid that is not covalently attached to a tetrasaccharide unit of PSA (i.e., it does not comprise the polysaccharide portion of PSA that is comprised of repeating tetrasaccharide units).

Structural analysis showed this lipid to belong to the class of lipid A molecules normally found in Gram negative bacteria. GLA, as it is referred to in this disclosure, comprises a glucosamine disaccharide with 3 to 5 acyl chains covalently bound to the sugars. It can be a monophosphorylated or non-phosphorylated at the diglucosamine. One of the glucosamine residues is linked to an oligosaccharide core of 10 or fewer sugars, including 9, 8, 7 or less sugars, by an acid labile bond such as a ketosidic bond.

Figure 5:
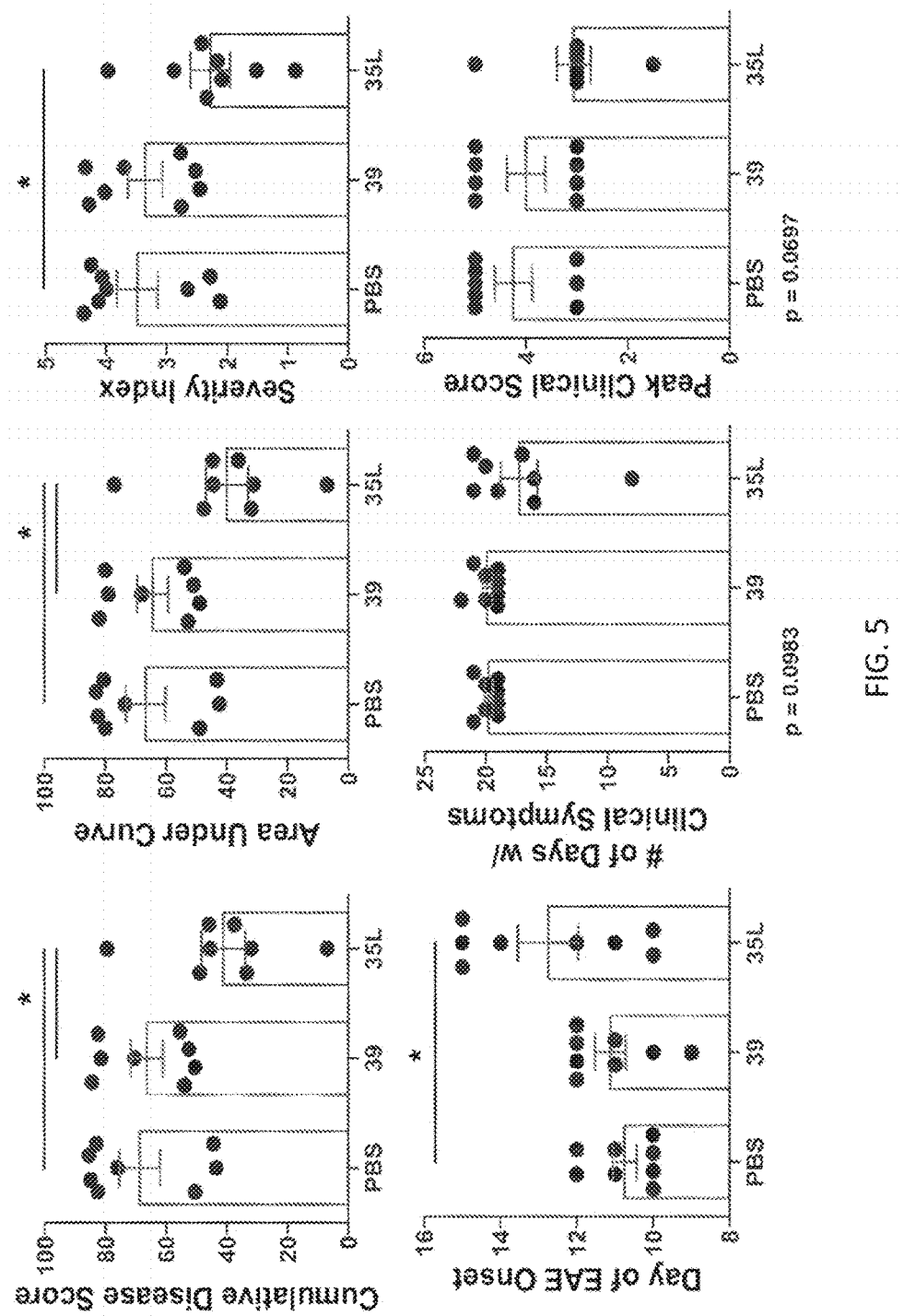
FIG. 5 provides various metrics using the same EAE mouse model as described for FIGS. 4A-4C to show that PSA with higher levels of GLA provides better protection in the EAE model than PSA alone. The statistical significance of the three parameters in the top row and the parameter in lower left were all $p<0.01$. For example, the upper left plot shows the cumulative disease scores calculated as the sum of all EAE clinical scores for each group of mice. Purified lipidated PSA is indicated as 39 and a mixture of purified lipidated PSA and free GLA, in a roughly 4:1 w/w mixture, is indicated as 35L. In these experiments, about 100 micrograms of lipidated PSA (39) were used per mouse. Similarly about 100 micrograms of the 35L preparation were used per mouse, corresponding to about 80 micrograms of lipidated PSA and 20 micrograms of GLA.
Figure 6B:
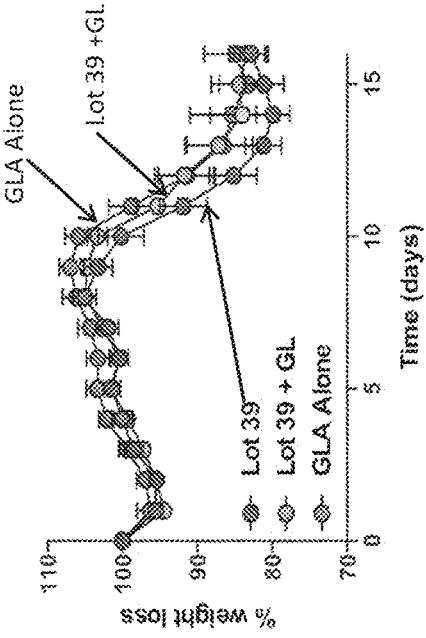
FIGS. 6A-6D show that GLA acts as an adjuvant for lipidated PSA. The experiment was performed as explained for FIGS. 4A-4C. Lot 39 refers to purified lipidated PSA. GLA alone refers to purified GLA. Lot 39 and GL refers to a preparation made by combining Lot 39 and GLA in roughly a 4:1 w/w ratio. Similar results were obtained using a ratio of about 100:1.
Figure 6D:
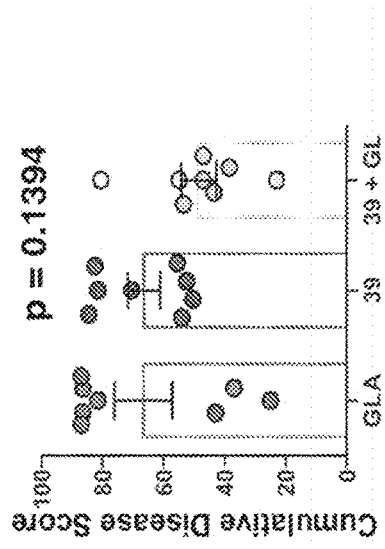
Figure 6A:
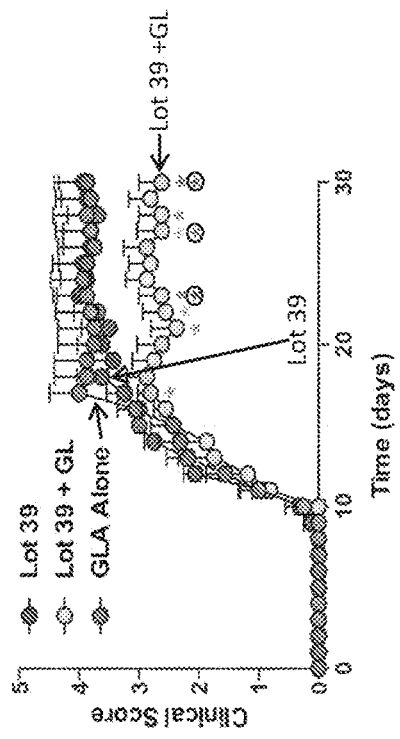
Figure 6C:
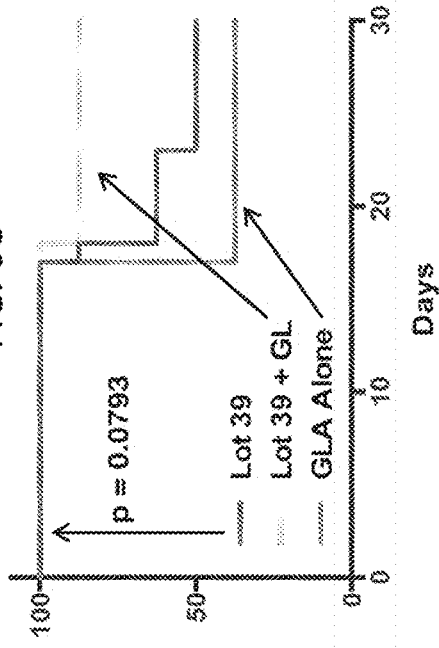
Figure 7B:
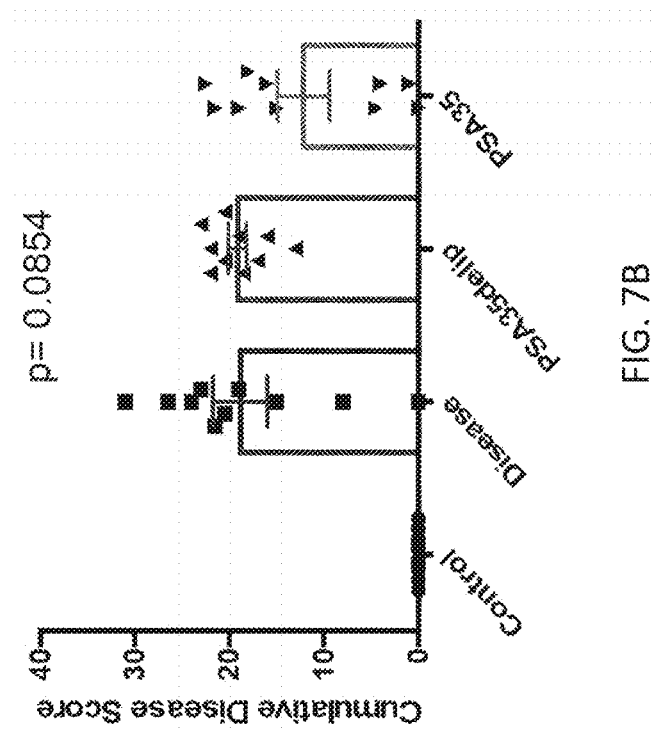
FIGS. 7A-7B show that a delipidated PSA preparation (referred to as PSA35 delip) cannot protect in EAE. PSA35 refers to a preparation that comprises lipidated PSA and free GLA. PSA35 delip refers to a preparation of PSA35 that has been acid hydrolyzed to cleave the lipid moiety from lipidated PSA and has also undergone a lipid extraction with organic solvent chloroform in order to remove all free lipid including all released lipid. PSA35 delip likely comprises the repeating tetrasaccharide polysaccharide chain of PSA conjugated to the oligosaccharide core unit. It lacks the diglucosamine-containing glycolipid. The experiment was performed as explained in FIGS. 4A-4C.
Figure 7A:
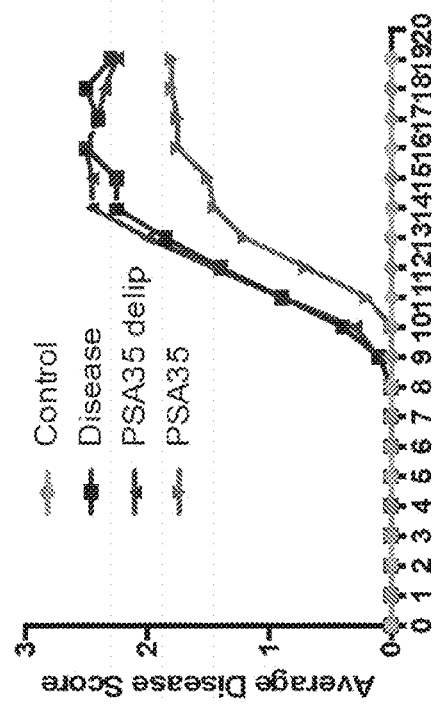
Figure 8:
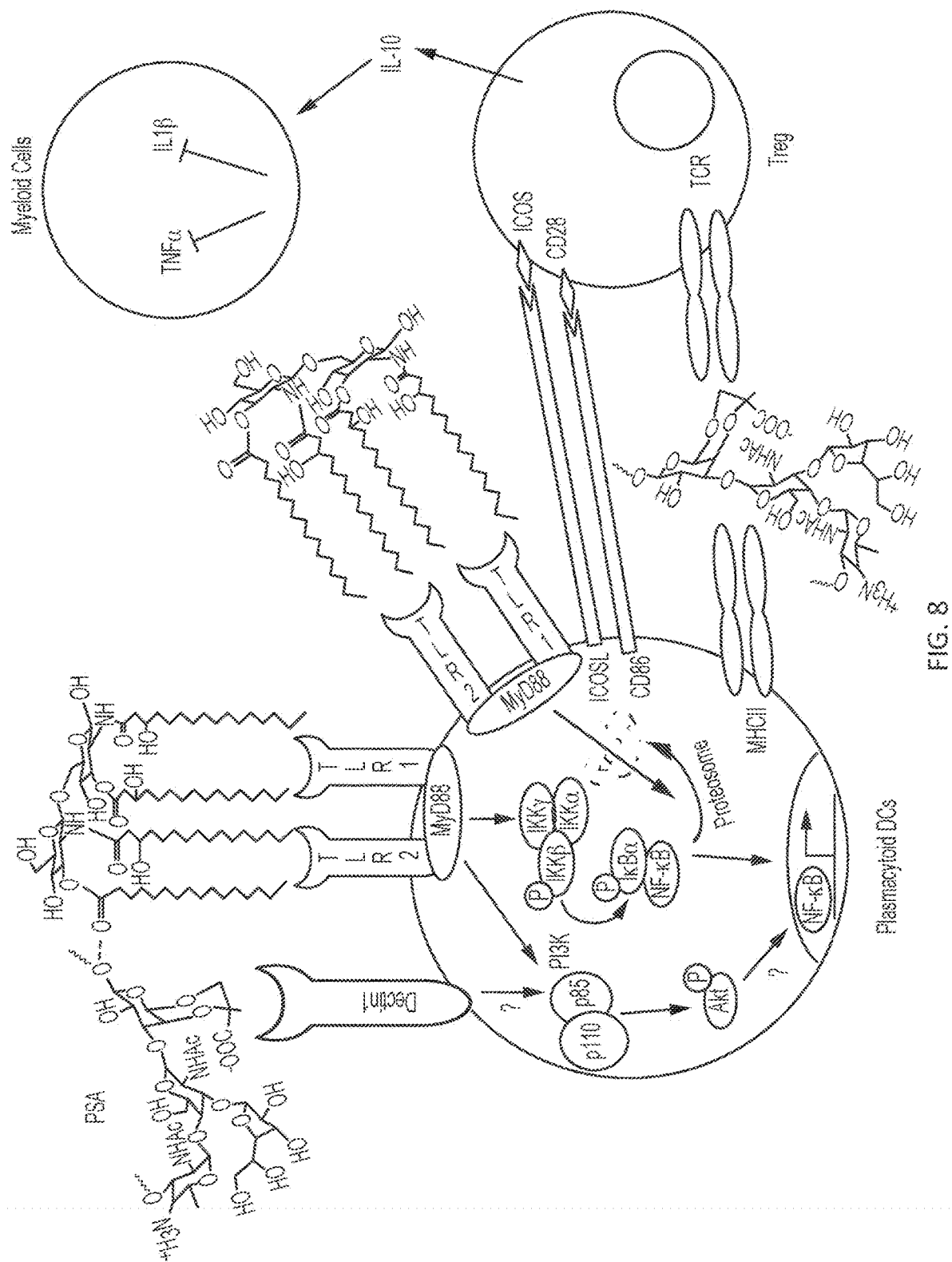
FIG. 8 is a schematic of a model of lipidated PSA induced immunomodulation. In this model, free GLA are shown to bind to a TLR2/1 dimer via the acyl chains, thereby stimulating an innate immune response. Although not shown, the free GLA may comprise the oligosaccharide core unit.
Figure 9:
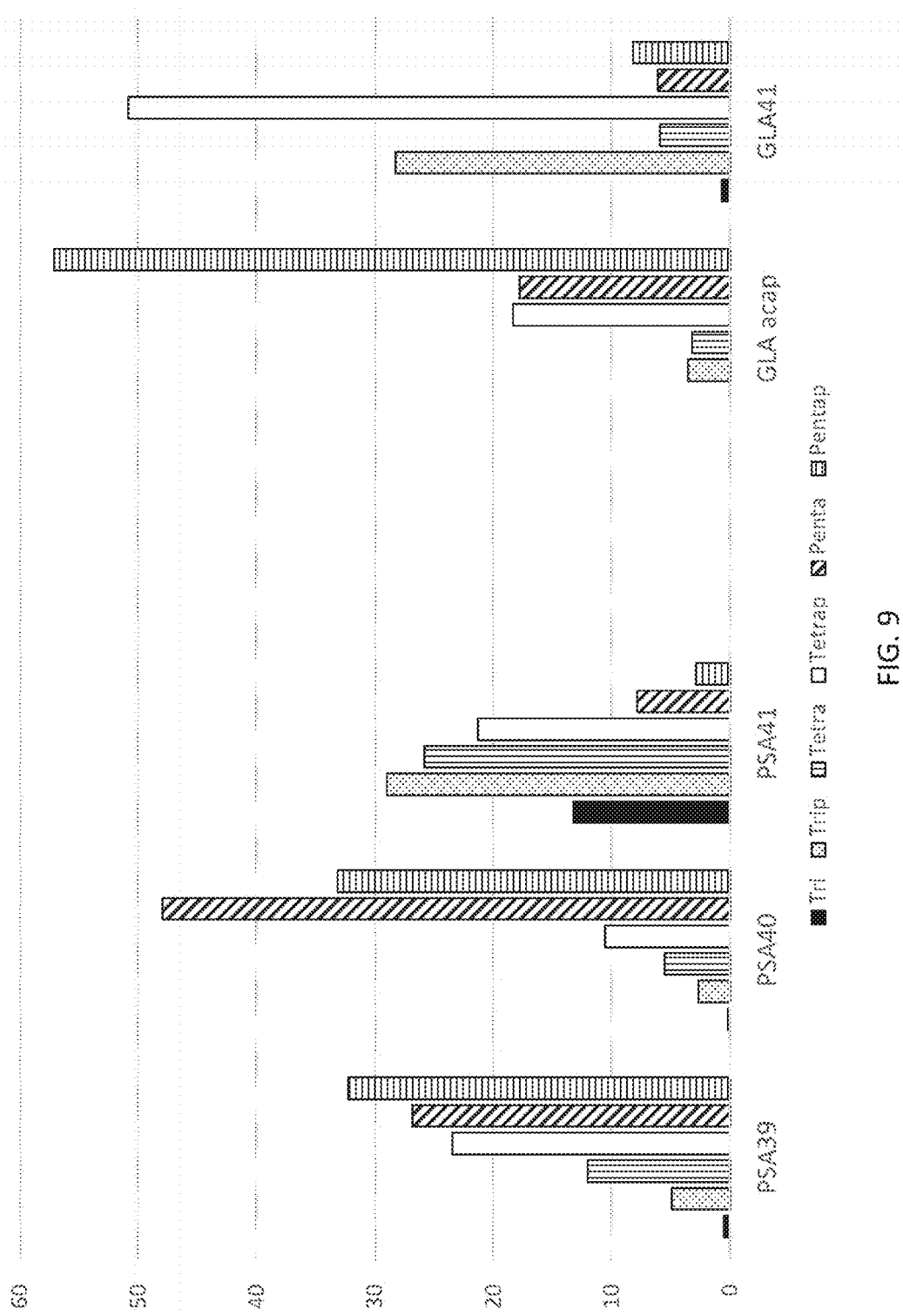
FIG. 9 shows the lipid profile of various lots of PSA (PSA39, PSA40 and PSA41) and GLA (GLA acap which was derived from an unencapsulated mutant and GLA41). Each lot was tested for the presence of tri-acylated, tri-acylated and phosphorylated, tetra-acylated, tetra-acylated and phosphorylated, penta-acylated, and penta-acylated and phosphorylated glycolipid moieties. The bars represent the amount of each glycolipid moiety as a percentage of the total lipid (y-axis). It is clear that each preparation contains the same lipid species but in different percentages. In particular, PSA41 and GLA41 contain the same lipid species, although the lipids do not appear to be similarly distributed between the PSA and GLA lots.
Figure 10:
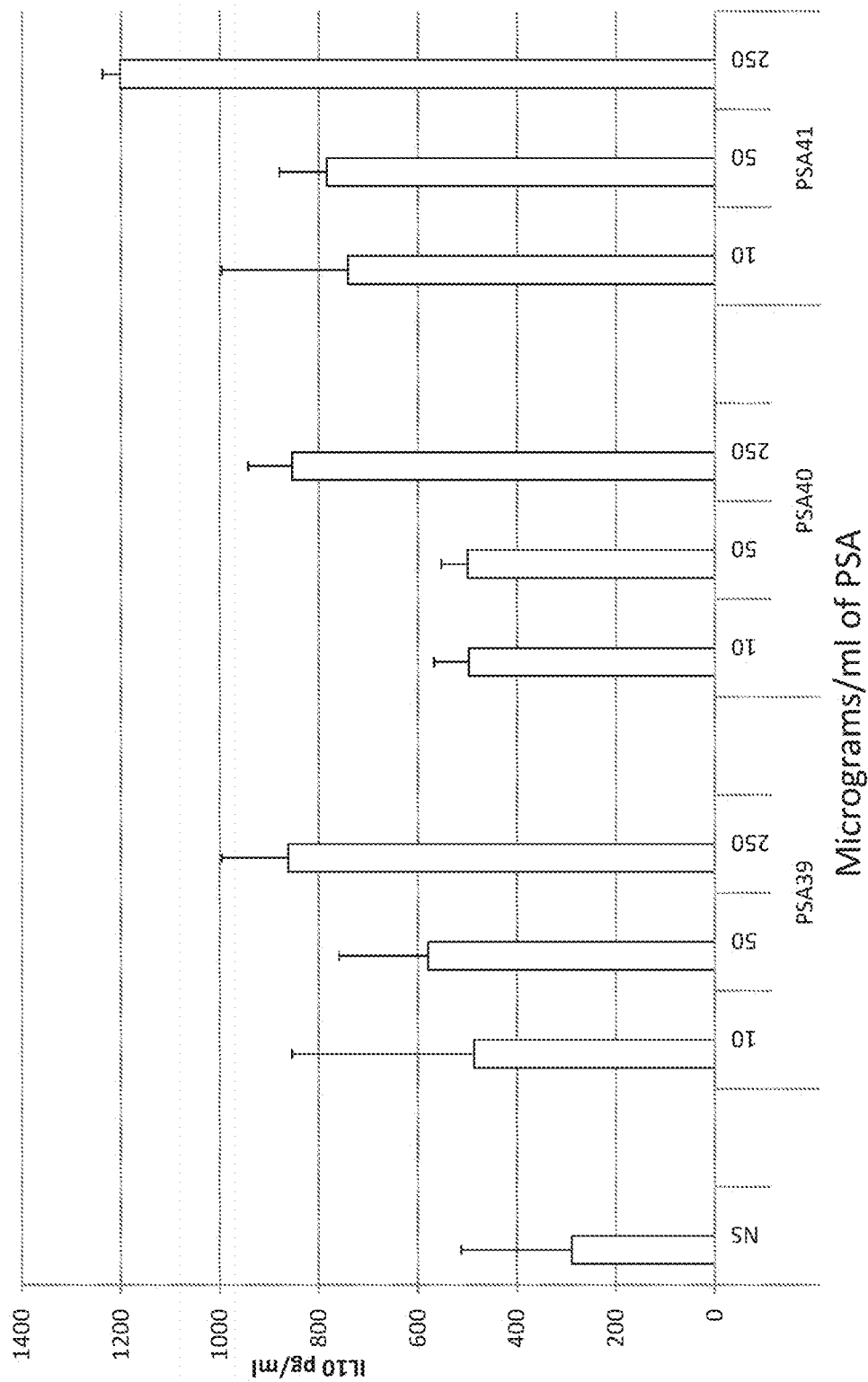
FIG. 10 shows an in vitro dose response (IL-10 production) of SpDC+T cells co-cultured with dendritic cells and exposed to 10, 50 and 250 mg/ml of PSA39, PSA40 and PSA41. PSA41 appears more potent in its ability to induce IL-10 as compared to other two preparations.
Figure 11:
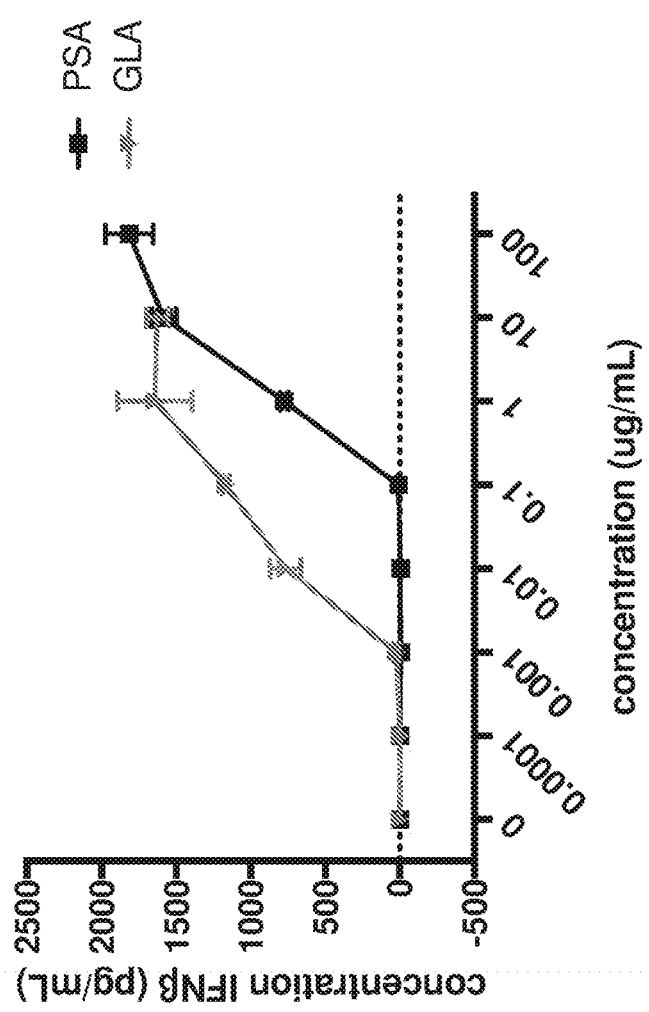
FIG. 11 shows that interferon-$\beta$ is induced by B. fragilis glycolipid whether or not attached to PSA. Model antigen presenting cells in the form of bone marrow derived dendritic cells (BMDCs) were stimulated for 6 hours with B. fragilis polysaccharide A (PSA) or the purified glycolipid anchor (GLA unencapsulated mutant), followed by collection of supernatants. A cytokine ELISA was used to detect levels of interferon-$\beta$ (IFN$\beta$) in the supernatants. PSA doses are shown stoichiometrically. The two curves would be superimposed if plotted on a molar basis because GLA is about 1% of a PSA molecule (i.e., 100 micrograms of PSA contain about 1 microgram of GLA).
Figure 12:
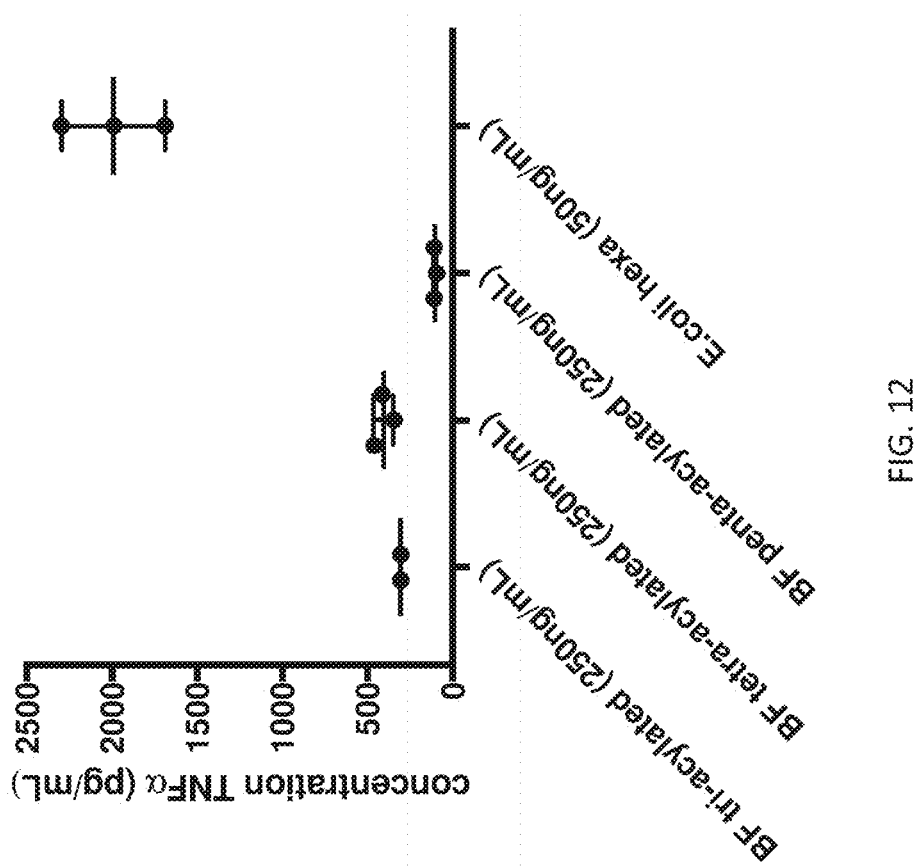
FIG. 12 shows that different acylation structures of B. fragilis GLA induce low levels of pro-inflammatory cytokines such as TNF$\alpha$. Model antigen presenting cells in the form of bone marrow derived dendritic cells (BMDCs) were stimulated for 6 hours with tri-, tetra- or penta-acylated B. fragilis GLA or hexa-acylated E. coli lipid A, followed by collection of supernatants. A cytokine ELISA was used to detect levels of TNF$\alpha$ in the supernatants. The three GLA species differ in their ability to induce TNF$\alpha$, but they all induce a much lower level of TNF$\alpha$ as compared to E. coli lipid A.
Figure 13:
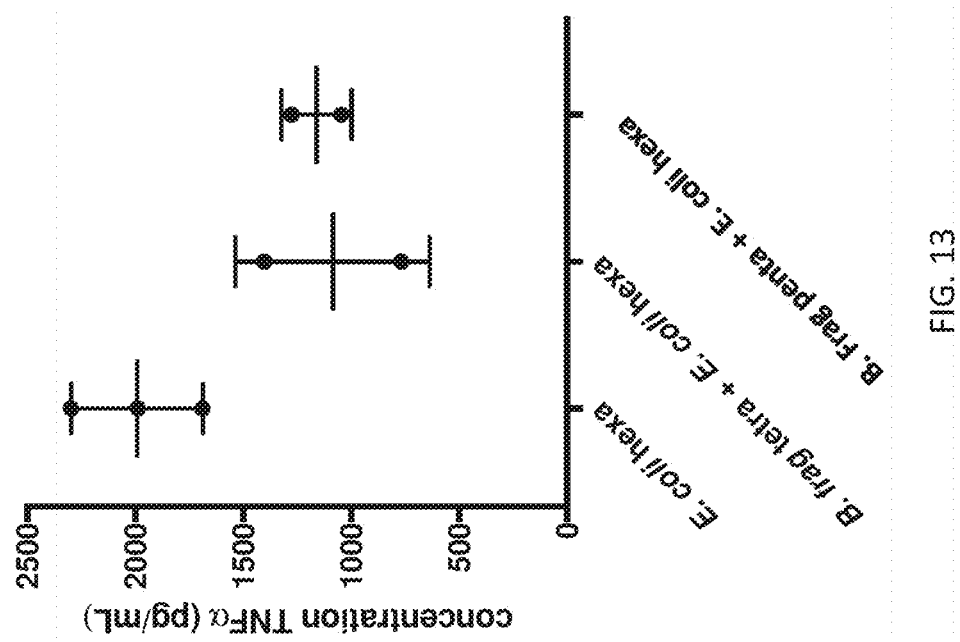
FIG. 13 shows that tetra-acylated and penta-acylated B. fragilis lipid A antagonize production of pro-inflammatory TNF$\alpha$ secretion by E. coli hexa-acylated lipid A. Model antigen presenting cells in the form of bone marrow derived dendritic cells (BMDCs) were stimulated for 6 hours with purified tetra-acylated B. fragilis GLA and hexa-acylated E. coli lipid A (in a 5:1 ratio) or with purified penta-acylated B. fragilis GLA and hexa-acylated E. coli lipid A (in a 5:1 ratio), followed by collection of supernatants. A cytokine ELISA was used to detect levels of TNF$\alpha$ in the supernatants. Both the tetra-acylated and penta-acylated GLA were able to suppress the pro-inflammatory response to lipid A. This suggests a suppressive activity that may be useful, among other things, in treating gram negative bacterial infection.

In order to enhance the harvest of intact glycolipid, the acid hydrolysis step was eliminated and lots were prepared with lipidated PSA and the free glycolipid. Such preparations are identified herein as 35L or PSA35L. These preparations were further analyzed and found to comprise on average about a 4:1 ratio of lipidated PSA to free GLA (w/w). In the in vivo EAE model, treatment with the 35L preparation delayed the EAE clinical outcome, and reduced the severity and the cumulative scores of the disease as compared to a purified lipidated PSA preparation referred to herein as PSA39 (DOC treated lipidated PSA preparation that did not contain free lipid (FIG. 4A, FIG. 5 upper left corner, and FIG. 4C). Next a mixture of free lipid and lipidated PSA was reconstituted at a 4:1 ratio (w/w), and this mixture was tested in the same experiment. The reconstituted mixture, referred to herein as "Lot 39+GL" conferred protection similar to that seen with 35L (FIGS. 6A, 6C and 6D). Moreover, when the PSA35L preparation (comprising lipidated PSA and free lipid in a 4:1 w/w ratio) was hydrolyzed and delipidated after purification, it lost its ability to protect (FIGS. 7A-7B).

Figure 3:
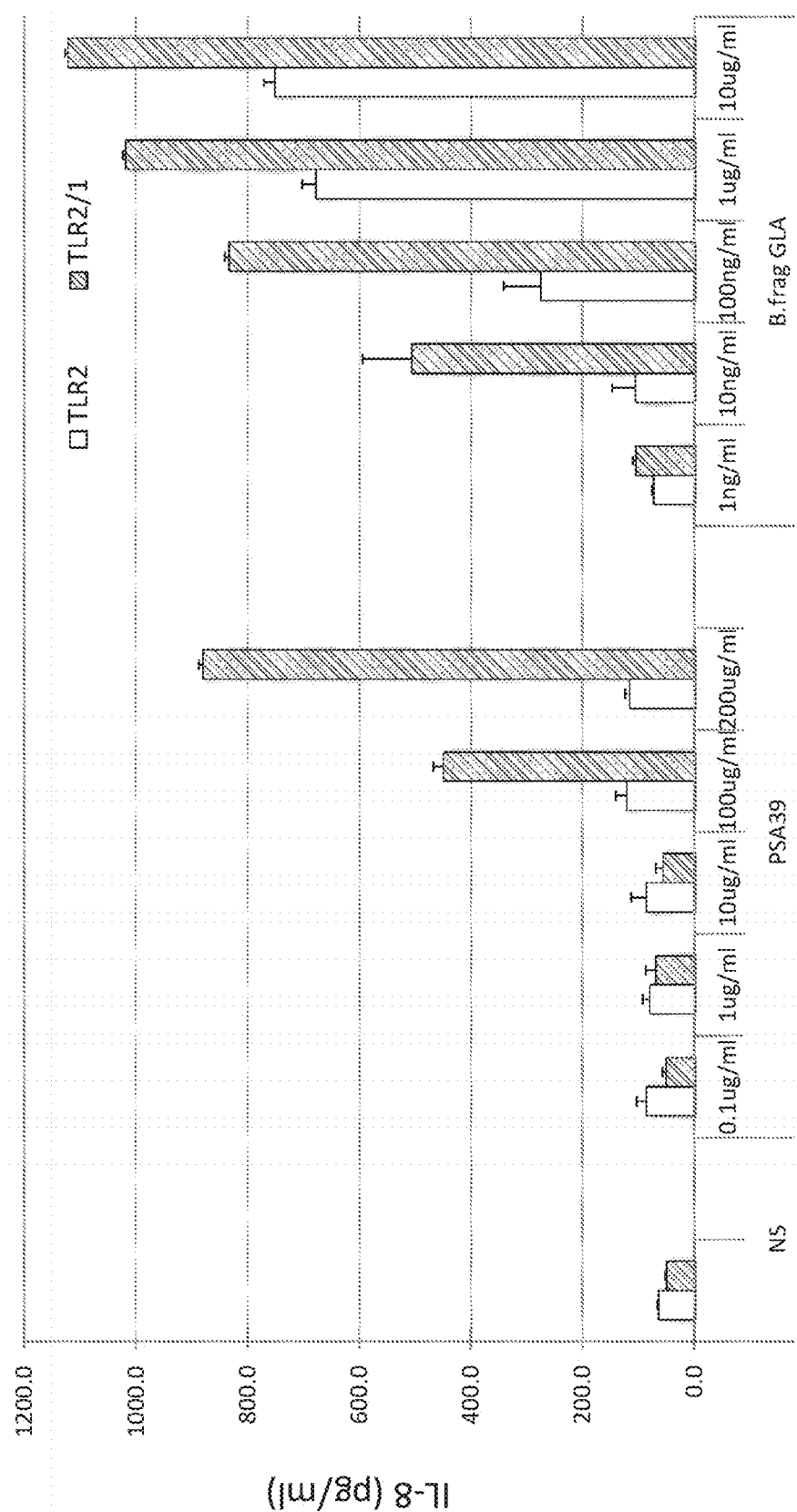
FIG. 3 is a bar graph showing that B. fragilis GLA activates TLR2 similar to lipidated PSA. The graph further shows that GLA can activate TLR2 at much lower concentrations as compared to lipidated PSA. The graph shows IL-8 production in HEK cells that are stably transfected with TLR2 only (white, or first bar of each pair of bars) or transfected with TLR2 and TLR1 (diagonal striped, or second bar of each pair of bars) in response to purified lipidated PSA that does not contain any free lipid (referred to as PSA39) and B. fragilis GLA alone. HEK cells overexpressing TLR2 and TLR2/1 were stimulated with PSA39 or B. frag GLA for 24 hours and IL-8 levels in the culture supernatant were measured with ELISA. The Figure shows that far less (e.g., about 20 fold less to about 100 fold less) GLA preparation is needed to stimulate the same level of IL-8 expression from the HEK cells. For example, the 100 ng/ml of GLA induces about 100-fold more IL-8 than does the 10 microgram/ml of PSA39, even though the latter dose contains about 100 nanograms of GLA. TLR2 activation plays a role in innate immunity, so the ability of GLA to stimulate TLR2 indicates that GLA is able to stimulate innate immunity. The ability of lipidated PSA (PSA39) to stimulate TLR2 may be due to its glycolipid moiety which comprises only about 1% of the mass of the lipidated PSA.

Further analysis revealed that GLA activates TLR2/TLR1 expressing HEK cells in a fashion similar to that seen with lipidated PSA (FIG. 3).

Taken together, the data suggest that GLA acts as an adjuvant to induce innate immunity. Such activity may occur through engagement and signaling of the TLR2/TLR1 heterodimer complex, and it likely enhances immune responses to PSA. In addition, the findings indicate use of GLA in enhancing immune responses to other antigens including but not limited to bacterial antigens, cancer antigens, and the like.

Provided herein is the structural identification and characterization of the glycolipid moiety of lipidated PSA. It has been found in accordance with this disclosure that these glycolipids are comprised of a diglucosamine substituted with three, four or five acyl chains. The glycolipid in some instances further comprises an oligosaccharide core unit conjugated to the diglucosamine via an acid-labile ketosidic bond. This glycolipid has been shown to activate an innate immune response and to enhance an immune response to lipidated PSA.

The glycolipid structure will now be described in greater detail in the context of lipidated PSA.

Lipidated PSA

A form of lipidated PSA isolated from mutant *B. fragilis* cells comprises a polysaccharide component conjugated, at its reducing end, an oligosaccharide core unit, and a diglucosamine conjugated to 3-5 acyl chains. As described in greater detail herein, the innate immunostimulatory activity appears attributable to the diglucosamine substituted with acyl chains. The oligosaccharide core unit, by virtue of its hydrophilicity, helps to render the lipid component more water soluble. Thus, while the immunostimulatory activity is believed to exist in the acyl chains, typically the GLA of this disclosure will further comprise the oligosaccharide core unit in order to facilitate its dissolution in an aqueous solution, such as but not limited to a pharmaceutical formulation.

Polysaccharide Component

The polysaccharide component of lipidated PSA, referred to herein as PSA, comprises a tetrasaccharide repeating unit shown below. It possesses zwitterionic behavior as conferred by a positive charge on its free amine group and a negative charge on its free carboxyl group (per repeating tetrasaccharide unit). Its naturally occurring state has been reported to comprise over 60 tetrasaccharide repeating units (e.g., up to and including in some instances about 100, or about 200, or about 300 repeated units on average), and it has an average molecular size of about 150 kD (with a range of about 75 kD to 240 kD).

The repeating tetrasaccharide unit of PSA has a structure as follows:

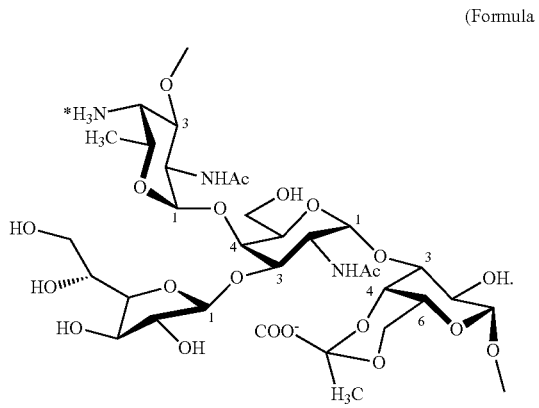

(Formula I)

The tetrasaccharide repeating unit may also be expressed as follows:

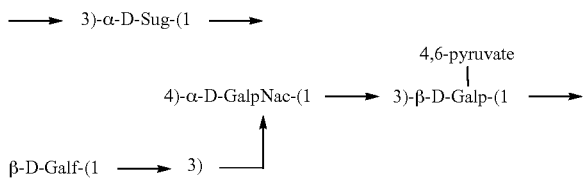

Synthetic forms of lipidated PSA may comprise comprising various ranges of tetrasaccharide units (e.g., 1-60, 1-50, 1-40, 1-30, 1-20, 1-10, 1-9, 1-8, 1-7, 1-6, or 1-5 tetrasaccharide units). Such shorter variants can be obtained by depolymerizing naturally occurring lipidated PSA or by depolymerizing PSA obtained from lipidated PSA. PSA can be depolymerized using for example chemical means (e.g., using reactive oxygen species or reactive nitrogen species such as but not limited to nitrogen monoxide, as described in Duan and Kasper, Glycobiology, 2011, 21(4):401-409), mechanical means, and/or enzymatic means that are known in the art.

The invention further contemplates synthetic forms of lipidated PSA comprising more than 300 repeating tetrasaccharide units, including without limitation 350, 400, 500, 600, 700, 800, 900 or 1000 units or more.

As described herein, the polysaccharide component may be covalently conjugated to the glycolipid, or in certain synthetic forms it may be unconjugated to the glycolipid. If covalently conjugated, it may be conjugated via a glycosidic bond to the oligosaccharide core unit. In other embodiments, it may be conjugated via a ketosidic bond or other acid labile bond or via a bond such as an ester, an amide, or an ether bond to form a non-naturally occurring lipidated PSA.

Glycolipid Component

Figure 2:
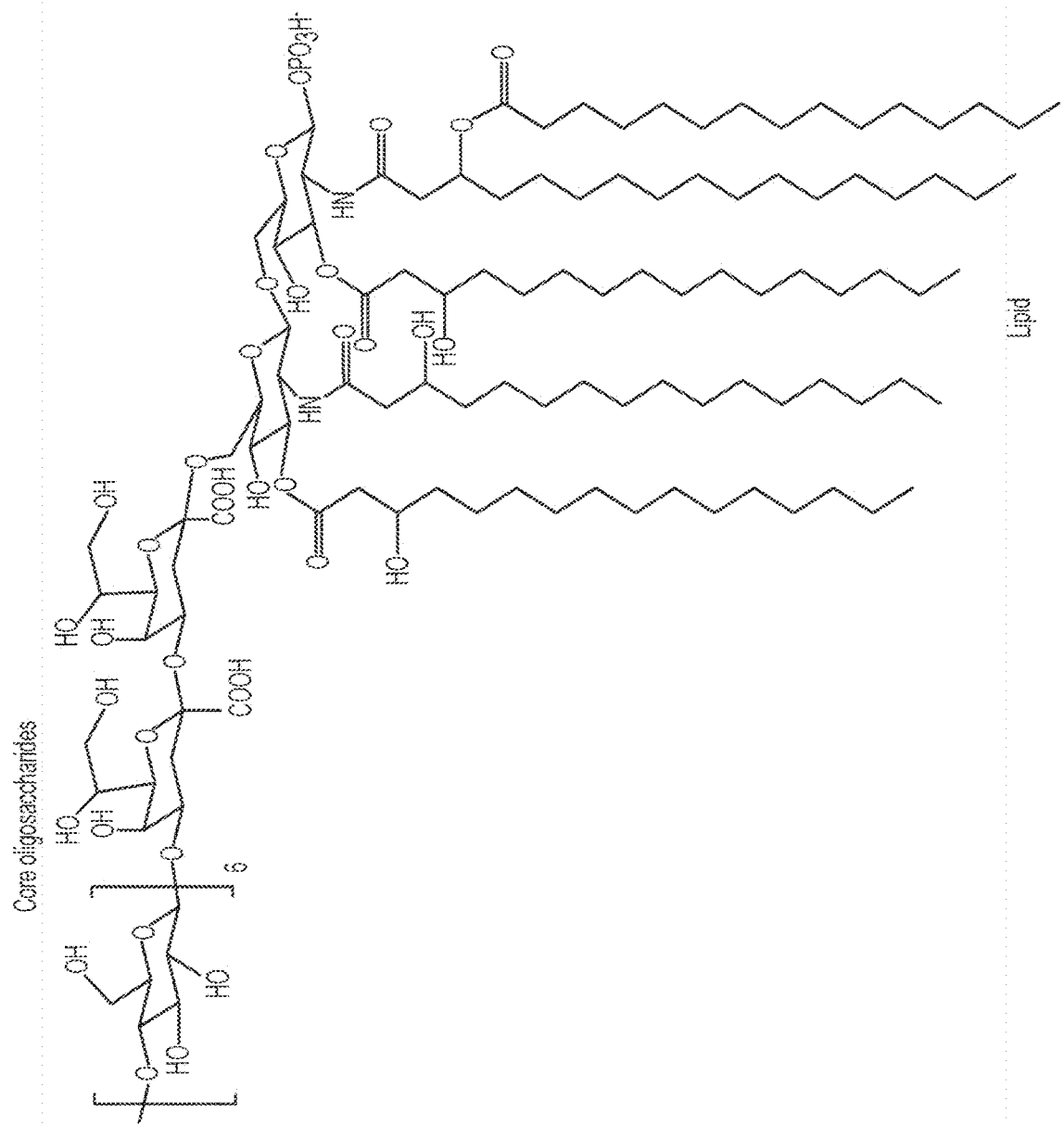
FIG. 2 is one embodiment of a proposed generic structure of isolated B. fragilis glycolipid antigen (referred to herein as GLA) with no repeating tetrasaccharide attached. The structure includes a core oligosaccharide unit attached to a diglucosamine-comprising glycolipid moiety having 5 acyl chains. One glucosamine is phosphorylated. The linkage between the diglucosamine and the core oligosaccharide unit is an acid-labile ketosidic linkage. When the oligosaccharide core unit is linked to the repeating tetrasaccharide units of PSA (not shown), this occurs through a glycosidic linkage. The oligosaccharide core unit may comprise galactose, glucose or fucose sugars. It may further contain KDO residues that connect the diglucosamine to the remaining sugars of the core unit. As illustrated, it comprises 6 galactose units conjugated to 2 KDO residues conjugated, through a ketosidic linkage, to a diglucosamine conjugated to 5 acyl chains. The diglucosamine is monophosphorylated. As taught herein, though, the glycolipid may be non-phosphorylated, the diglucosamine may be tri- or tetra-acylated, and there may be variation in the oligosaccharide core unit in terms of number and nature of sugars. Accordingly, GLA may minimally comprise the diglucosamine linked to a plurality of acyl chains (e.g., 3-5 chains).

The glycolipid component comprises a diglucosamine substituted with one or more acyl chains, and preferably 3, 4 or 5 acyl chains. An exemplary diglucosamine in the context of a glycolipid is provided in FIG. 2. It is now recognized in accordance with this disclosure that the diglucosamine is conjugated to the oligosaccharide core unit via a ketosidic bond that is acid-labile and thus susceptible to stringent hydrolysis.

The disaccharide may be conjugated to one or more acyl chains, including three, four, or five acyl chains in some instances via for example ester or amide linkages, and thus may be referred to as "O" substituted (or O-linked) or "N" substituted (or N-linked) respectively. In some instances, each glycolipid (or GLA, as used herein) comprises three, four or five acyl chains. Accordingly, the glycolipid may be referred to herein as tri-acylated, tetra-acylated or penta-acylated forms.

The acyl chains may range in length from 14 to 17 carbons, in some instances. The acyl chains may be unmodified or they may be modified. If modified, the acyl chains may be hydroxy-modified. Thus, in some instances, the glycolipid may comprise one or more acyl chains characterized as C14:0, C14:0-OH, C15:0, C15:0-OH, C16:0, C16:0-OH, C17:0, and C17:0-OH.

A single preparation of glycolipid may yield a number glycolipid species that differ from each other with respect to acyl chain number. The exact composition of a glycolipid may be determined using mass spectrometry (MS), wherein different glycolipid species give rise to different and discernable spectra.

Examples of different penta-acylated species include:
(1) one chain of C16:0-OH, three chains of C17:0-OH, and one chain of C15:0,
(2) two chains of C16:0-OH, two chains of C17:0-OH, and one chain of C15:0,
(3) three chains of C16:0-OH, one chain of C17:0-OH, and one chain of C15:0,
(4) four chains of C16:0-OH, and one chain of C15:0, and
(5) four chains of C16:0-OH, and one chain of C14:0.

Various species of tetra-acylated and tri-acylated species are similarly contemplated.

It will therefore be appreciated glycolipids of this disclosure, whether isolated from *B. fragilis* or generated de novo, and whether conjugated or unconjugated to an oligosaccharide core unit, may comprise any of the foregoing combinations of acyl chains, without limitation:
(1) C16:0-OH acyl chain(s) only,
(2) C17:0-OH acyl chain(s) only,
(3) C16:0-OH and C17:0-OH chain(s) only,
(4) C16:0-OH and C17:0-OH and C15:0 chain(s) only,
(5) C16:0-OH and C17:0-OH and C14:0 chain(s).

The number of each type of chain may vary, and may include without limitation the following options
(1) 0-4 C16:0-OH chains,
(2) 0-4 C17:0-OH chains,
(3) 0 or 1 C14:0 chains, and
(4) 0 or 1 C15:0 chains.

The foregoing examples are not to be considered limiting, and rather the invention contemplates various combinations, and combinations of the foregoing, to be used in compositions provided herein.

The invention provides defined glycolipid mixtures, having known, and thus optionally pre-defined, glycolipid content and composition, and optionally known and/or pre-defined polysaccharide (e.g., PSA) to glycolipid ratios or non-PSA antigen to glycolipid ratios. Thus, the glycolipids of this disclosure may be characterized in terms of any of these structural features, thereby further distinguishing these products from those of the prior art, and where necessary from naturally occurring products. For example, based on the teachings provided herein, the invention provides compositions comprising glycolipids that are only or predominantly (e.g., greater than 50%, or at least 55%, at least 60%, at least 65%, at least 70%, at least 75%, at least 80%, at least 85%, at least 90%, or at least 95%) tri-acylated, or tetra-acylated, or penta-acylated, or some combination thereof including but not limited to tetra- and penta-acylated. Such chemically defined compositions were not heretofore contemplated or possible.

Isolated Forms

The preparations provided herein can be characterized by their content of released or free glycolipids. Such content can be about 30%, 25%, 20%, 15%, 10%, 5%, 4%, 3%, 2%, 1% or less. Such content can be less than 35%, less than 30%, less than 25%, less than 20%, less than 15%, less than 10%, less than 5%, less than 4%, less than 3%, less than 2%, less than 1%, less than 0.5%, less 0.1%, less than 0.05%, less than 0.001%, less than 0.0005%, less than 0.0001% (w/w of released glycolipid to lipidated PSA). The amount of glycolipid may be determined for example using the gel electrophoresis methods or mass spec methods. The glycolipid may also be considered to be pure (i.e., it is free or substantially free of contaminant). The degree of purity may be at least 70%, 75%, 80%, 85%, 90%, 95%, 96%, 97%, 98%, 99%, 99.1%, 99.2%, 99.3%, 99.4%, 99.5%, 99.6%, 99.7%, 99.8%, or 99.9%, or higher.

Accordingly, the invention provides compositions comprising glycolipids including compositions comprising isolated glycolipid at a purity and/or a concentration that has not been heretofore achieved. Also provided are compositions comprising or consisting essentially of particular species of glycolipid or particular subsets of species of glycolipid. These species may be characterized and thus distinguished from other species and from bulk glycolipid in terms of their lipid and oligosaccharide components. The lipid components may be characterized by the number, position and type of acyl chains they possess. For example, a composition may comprise at least 70%, 75%, 80%, 85%, 90%, 95%, or more of a tri-acetylated, tetra-acetylated and/or penta-acetylated glycolipid.

The compositions may be defined by their degree of purity, for example with respect to their glycolipid components, or with respect to their content of contaminants such as non-lipidated PSA. The compositions may be defined by their concentration of glycolipid components, or by their ratio of glycolipid to other components.

Synthetic Forms

The invention further provides additional synthetic, non-naturally occurring species of glycolipids.

Glycolipid Compositions

Isolated intends that the glycolipid (or other agent) is provided in a more pure form or a more concentration form compared to its synthesized or obtained form. An "isolated" glycolipid may be a glycolipid that is prepared or obtained from *B. fragilis*, and is physically separated from a natural environment (e.g., a *B. fragilis* cell, components of the *B. fragilis* cell, and/or components of the *B. fragilis* cell capsular complex such as but not limited to PSB). It does not intend that any naturally occurring product has the same structure of glycolipid as described herein.

In some embodiments, the compositions are substantially free of naturally occurring contaminants such as nucleic acids (e.g., DNA and RNA), proteins, and other components of *B. fragilis* and/or the *B. fragilis* capsule. Substantially free, as used herein, intends that these contaminants represent about or less than 5%, less than 1%, less than 0.5%, or less than 0.1% (or less) by weight (weight of the contaminant to weight of the glycolipid). In some instances, such contaminants may be undetectable.

Various compositions may or may not contain LPS. LPS may be present in an amount of about 0.5% (w/w of LPS relative to other components in a composition).

Some compositions may comprise at least about 20%, 25%, 30%, 35%, 40%, 45%, 50%, 55%, 60%, 65%, 70%, 75%, 80%, 85%, 90%, 95%, 96%, 97%, 98%, 99%, or more (w/w) of glycolipid.

Some compositions may comprise at least about 95%, 96%, 97%, 98%, 99%, or more (w/w) of lipidated PSA and less than 5%, less than 4%, less than 3%, less than 2%, less than 1%, less than 0.5%, or less of free, released glycolipid.

Methods of Use

Also provided are methods of using the various forms of glycolipid in vitro and in vivo. The various glycolipid forms herein can be used as immunomodulators including immunostimulators, particularly in view of their enhanced ability to stimulate antigen presenting cells such as plasmacytoid dendritic cells. These forms are contemplated for use in vitro and in vivo. In vitro uses include use as an analytical tool (e.g., for screening assays) and as an assay standard or control (e.g., as a positive control or a comparator in an in vitro assay such as a IL-8 induction assay). In vivo uses include uses in animal models and also in human and non-human subjects to treat or prevent conditions that would benefit from such immunomodulation including immunostimulation. Such conditions include those in which an enhanced innate and/or adaptive immune response is beneficial. Other conditions include but are not limited to autoimmune disorders (e.g., multiple sclerosis and inflammatory bowel disease).

The glycolipid component may be used as a single agent, or it may be used in combination with other agents such as antigens or cells such as antigen-presenting cells. It may be used to stimulate antigen-presenting cells in vivo or in vitro. One application may involve obtaining antigen-presenting cells from a subject, stimulating such cells ex vivo with the glycolipid of this disclosure with or without antigen, followed by re-introduction of such cells with and without glycolipid and/or antigen to the subject. Alternatively, the glycolipid may be administered to a subject with and/or without antigen. Such immunization or vaccination protocols may involve several administrations of glycolipid and/or antigen. The administration of the glycolipid and the antigen may occur simultaneously (typically occurs if they are formulated together), or substantially simultaneously (typically occurs if they are formulated and administered separately but still within a short period of time in order to work in concert in a subject), and/or they may be formulated and administered separately (e.g., the glycolipid is administered before or after the antigen, including for example hours, days and/or weeks before or after).

The invention further contemplates use of the free polysaccharide component of lipidated PSA (i.e., a chain of repeating tetrasaccharide units that is not conjugated to the glycolipid component of lipidated PSA (including where such glycolipid comprises the oligosaccharide core unit) and the free glycolipid component obtained from lipidated PSA.

As another example, the polysaccharide and glycolipid may be used together in an unconjugated form.

The invention further contemplates use of the free PSA (i.e., a chain of repeating tetrasaccharide units that is not conjugated to the glycolipid (including where such glycolipid comprises the oligosaccharide core unit) and free glycolipid obtained from lipidated PSA.

In vivo uses include but are not limited to those involving human subjects. For example, in vivo uses include administration of the glycolipid and compositions thereof to a non-human subject in order to modulate an immune response, for example as a positive control or a comparator.

Infections

The glycolipids and compositions thereof may be administered to a subject having or at risk of having an infection such as a bacterial infection, a viral infection, a fungal infection, a parasitic infection, or a mycobacterial infection. In these aspects, the glycolipids may be used and/or administered with another therapeutic such as an anti-bacterial agent, an anti-viral agent, an anti-fungal agent, an anti-parasitic agent, or anti-mycobacterial agent. In these and other aspects, the glycolipids may be used and/or administered with an antigen in order to induce or enhance an immune response directed to the antigen (i.e., an antigen-specific immune response). Such antigens include bacterial antigens, viral antigens, fungal antigens, parasitic antigens, and mycobacterial antigens.

Anti-bacterial agents include broad spectrum antibiotics, narrow spectrum antibiotics, or limited spectrum antibiotics. The anti-bacterial agent may also be a cell wall synthesis inhibitor, cell membrane inhibitor, protein synthesis inhibitor, nucleic acid synthesis or functional inhibitor or a competitive inhibitor.

Anti-viral agents include immunoglobulin, amantadine, interferon, nucleoside analogue, nonnucleoside analogue, biflavanoid and protease inhibitor, although it is not so limited. In one embodiment, the protease inhibitor is indinavir, saquinavir, ritonavir, and nelfinavir. In another embodiment, the biflavanoid is robustaflavone, amentoflavone, or a derivative or salt thereof. In yet another embodiment, the non-nucleoside analogue is selected from the group consisting of delavirdine, nevirapine, efavirenz, alpha-interferon, recombinant CD4, amantadine, rimantadine, ribavirin and vidarabine.

Anti-fungal agents include imidazole, FK 463, amphotericin B, BAY 38-9502, MK 991, pradimicin, UK 292, butenafine, chitinase and 501 cream.

Anti-parasitic agents include albendazole, amphotericin B, benznidazole, bithionol, chloroquine HCl, chloroquine phosphate, clindamycin, dehydroemetine, diethylcarbamazine, diloxanide furoate, eflornithine, furazolidaone, glucocorticoids, halofantrine, iodoquinol, ivermectin, mebendazole, mefloquine, meglumine antimoniate, melarsoprol, metrifonate, metronidazole, niclosamide, nifurtimox, oxamniquine, paromomycin, pentamidine isethionate, piperazine, praziquantel, primaquine phosphate, proguanil, pyrantel pamoate, pyrimethanmine-sulfonamides, pyrimethanmine-sulfadoxine, quinacrine HCl, quinine sulfate, quinidine gluconate, spiramycin, stibogluconate sodium (sodium antimony gluconate), suramin, tetracycline, doxycycline, thiabendazole, tinidazole, trimethroprim-sulfamethoxazole, and tryparsamide.

Anti-mycobacterial agent include anti-tuberculosis agent such as isoniazid, rifampin, rifabutin, rifapentine, pyrazinamide, ethambutol, (+)calanolide A, (−)-calanolide A, (−)-soulattrolide, (−)-costatolide or (−)-7,8-dihydrosoulattrolide. Other anti-mycobacterial agents include streptomycin, dapsone, clarithromycin, ciprofloxacin, clofazamine, azithromycin, ethionamide, amikacin or resorcinomycin A.

Subjects to be treated according to this disclosure may have or may be at risk of developing a bacterial infection. Examples of bacterial infections to be treated according to this disclosure include but are not limited to an *E. coli* infection, a Staphylococcal infection, a Streptococcal infection, a *Pseudomonas* infection, *Clostridium difficile* infection, *Legionella* infection, *Pneumococcus* infection, *Haemophilus* infection, *Klebsiella* infection, *Enterobacter* infection, *Citrobacter* infection, *Neisseria* infection, *Shigella* infection, *Salmonella* infection, *Listeria* infection, *Pasteurella* infection, *Streptobacillus* infection, *Spirillum* infection, *Treponema* infection, *Actinomyces* infection, *Borrelia* infection, *Corynebacterium* infection, *Nocardia* infection, *Gardnerella* infection, *Campylobacter* infection, *Spirochaeta* infection, *Proteus* infection, *Bacteroides* infection, *H. pylori* infection, and anthrax infection.

In some embodiments, the subjects may have or may be at risk of developing a gram-negative bacterial infection. Gram negative bacteria include but are not limited to *Escherichia coli* (*E. coli*), *Pseudomonas aeruginosa*, *Neisseria meningitides*, *Neisseria gonorrhoeae*, *Chlamydia trachomatis*, *Yersinia pestis*, Non-typable *Hemophilus influenzae*, *Hemophilus ducreyi*, *Helicobacter pylori*, *Campylobacter jejuni; Bacteroides fragilis*, *B. thetaiotamicron*, *B vulgatis*, *Citrobacter rodentium*, *Haemophilus influenza*, *Vibrio cholerae*, *Salmonella shigella*, *Salmonella enteritidis*, *Salmonella enterica serovar typhi*, *Salmonella enterica serovar typhimurium*, *Klebsiella pneumoniae*, *Legionella pneumophila*, *Proteus mirabilis*, *Enterobacter cloacae*, and *Serratia marcescens*. In some embodiments, the tetra- and penta-acylated glycolipids provided herein, and compositions thereof, are used to treat gram-negative bacterial infections, such as any of the foregoing.

In some embodiments, the subject is experiencing sepsis.

In some embodiments, the subject does not have and is not at risk of developing a *B. fragilis* infection. In some embodiments, the subject does have or is at risk of developing a *B. fragilis* infection or a condition associated with type of infection.

Subjects to be treated according to this disclosure may have or may be at risk of developing a mycobacterial infection. Examples of mycobacterial infections to be treated according to this disclosure include but are not limited to tuberculosis or leprosy respectively caused by the *M. tuberculosis* and *M. leprae* species.

Subjects to be treated according to this disclosure may have or may be at risk of developing a viral infection. Examples of viral infections to be treated according to this disclosure include but are not limited to a Zika infection, an HIV infection, a Herpes simplex virus 1 infection, a Herpes simplex virus 2 infection, cytomegalovirus infection, hepatitis A virus infection, hepatitis B virus infection, hepatitis C virus infection, human papilloma virus infection, Epstein Barr virus infection, rotavirus infection, adenovirus infection, influenza A virus infection, respiratory syncytial virus infection, varicella-zoster virus infections, small pox infection, monkey pox infection, and SARS infection.

Subjects to be treated according to this disclosure may have or may be at risk of developing a parasitic infection. Examples of parasitic infections to be treated according to this disclosure include but are not limited to candidiasis, ringworm, histoplasmosis, blastomycosis, paracoccidioidomycosis, crytococcosis, aspergillosis, chromomycosis, mycetoma infections, pseudallescheriasis, and tinea versicolor infection. Still other parasitic infections that may be treated using the glycolipids of this disclosure include amebiasis, *Trypanosoma cruzi* infection, *Fascioliasis, Leishmaniasis, Plasmodium* infections, *Onchocerciasis, Paragonimiasis, Trypanosoma brucei* infection, *Pneumocystis* infection, *Trichomonas vaginalis* infection, *Taenia* infection, *Hymenolepsis* infection, *Echinococcus* infections, *Schistosomiasis*, neurocysticercosis, *Necator americanus* infection, and *Trichuris trichuria* infection.

Immune Therapies

The glycolipids and compositions thereof may be used to enhance immune therapies for a number of indications, both in a therapeutic and a prophylactic sense. Immune therapies include but are not limited to passive immune therapies such as immunoglobulin administration, and active immune therapies such as vaccination with antigens alone or antigens in the context of dendritic cells. The methods are intended to treat or prevent various indications that would benefit from an enhanced immune response.

In some embodiments, the immune response that is stimulated is a cell-mediated immune response involving antigen presenting cells and optionally T cells such as Treg cells. In some embodiments, the immune response is an innate immune response, while in others it is an adaptive immune response, while in yet others it is a combined innate and adaptive immune response. The immune response may, in some instances, be antigen specific.

The immune therapy may involve administration of an antibody or antigen-binding antibody fragment. The antibody or antigen-binding fragment thereof may be specific for a tumor vasculature molecule. Tumor vasculature molecules include but are not limited to endoglin, ELAM-1, VCAM-1, ICAM-1, ligand reactive with LAM-1, MHC class II antigens, aminophospholipids such as phosphatidylserine and phosphatidylethanolamine, VEGFR1 (Flt-1) and VEGFR2 (KDR/Flk-1). Antibodies to endoglin include TEC-4 and TEC-11. Antibodies that inhibit VEGF include 2C3 (ATCC PTA 1595). Other antibodies that are specific for tumor vasculature include antibodies that react to a complex of a growth factor and its receptor such as a complex of FGF and the FGFR or a complex of TGFβ and the TGFβR. Antibodies of this latter class include GV39 and GV97.

In a related embodiment, the antibody or antibody fragment is selected from the group consisting of trastuzumab, alemtuzumab (B cell chronic lymphocytic leukemia), gemtuzumab ozogamicin (CD33+ acute myeloid leukemia), hP67.6 (CD33+ acute myeloid leukemia), infliximab (inflammatory bowel disease and rheumatoid arthritis), etanercept (rheumatoid arthritis), rituximab, tositumomab, MDX-210, oregovomab, anti-EGF receptor mAb, MDX-447, anti-tissue factor protein (TF), (Sunol); ior-c5, c5, edrecolomab, ibritumomab tiuxetan, anti-idiotypic mAb mimic of ganglioside GD3 epitope, anti-HLA-Dr10 mAb, anti-CD33 humanized mAb, anti-CD52 humAb, anti-CD1 mAb (ior t6), MDX-22, celogovab, anti-17-1A mAb, bevacizumab, daclizumab, anti-TAG-72 (MDX-220), anti-idiotypic mAb mimic of high molecular weight proteoglycan (I-Mel-1), anti-idiotypic mAb mimic of high molecular weight proteoglycan (I-Mel-2), anti-CEA Ab, hmAbH11, anti-DNA or DNA-associated proteins (histones) mAb, Gliomab-H mAb, GNI-250 mAb, anti-CD22, CMA 676), anti-idiotypic human mAb to GD2 ganglioside, ior egf/r3, anti-ior c2 glycoprotein mAb, ior c5, anti-FLK-2/FLT-3 mAb, anti-GD-2 bispecific mAb, antinuclear autoantibodies, anti-HLA-DR Ab, anti-CEA mAb, palivizumab, bevacizumab, alemtuzumab, BLyS-mAb, anti-VEGF2, anti-Trail receptor; B3 mAb, mAb BR96, breast cancer; and Abx-Cbl mAb.

The antibody or antibody fragment may be an anti-HER2 antibody, such as trastuzumab. The antibody or antibody fragment may be an anti-CD20 antibody, such as rituximab.

In still another aspect, provided herein is a method for shortening a vaccination course. As used herein, "shortening a vaccination course" refers to reducing either the number of vaccine administrations (e.g., by injection) or the time between vaccine administrations. This is accomplished by stimulating a more robust immune response in the subject. The method may involve, in one embodiment, administering to a subject in need of immunization a glycolipid in an amount effective to induce an antigen-specific immune response to a vaccine administered in a vaccination course, wherein the vaccination course is shortened by at least one immunization. In other embodiments, the vaccination course is shortened by one immunization, two immunizations, three immunizations, or more. The method may involve, in another embodiment, administering to a subject in need of immunization a glycolipid of this disclosure in an amount effective to induce an antigen-specific immune response to a vaccine administered in a vaccination course, wherein the vaccination course is shortened by at least one day. In other embodiments, the vaccination course is shortened by one day, two days, three days, four days, five days, six days, one week, two weeks, three weeks, four weeks, one month, two months or more. In one embodiment, the glycolipid is administered substantially simultaneously with the vaccine.

Immunizations that can be modified in this way include but are not limited to newborn immunizations for HBV; immunizations at for example two months of age for Polio, DTaP, Hib, HBV, *Pneumococcus*; immunizations at for example four months of age for Polio, DTaP, Hib, *Pneumococcus*; immunizations at for example six months of age for Polio, DTaP, Hib, HBV, *Pneumococcus*; immunizations at for example 12-15 months of age for Hib, *Pneumococcus*, MMR, Varicella; immunizations at for example 15-18 months of age for DtaP; immunizations at for example 4-6 years of age for Polio, DPT, MMR; immunizations at for example 11-12 years of age for MMR; immunizations at for example 14-16 years of age for tetanus-diphtheria (i.e., Td) (with a repeat as a booster every 10 years).

As an example, a recommended vaccination course for tetanus/diphtheria includes a primary immunization series given in adults if not received as a child, followed by routine booster doses of tetanus-diphtheria (Td) every 10 years. The method of the invention will allow for a shortened series of vaccinations at the first time point, and may in some instances obviate the need for booster shots later on. As another example, hepatitis vaccination commonly requires three administrations spaced at least two weeks, and sometimes one month, apart in order to develop full immunity. Using the methods of the invention, it is possible to either reduce the number of injections from three to two or one, or to reduce the time in between injections from weeks or months to days or weeks. Vaccination courses that can be shortened by the method of the invention include but are not limited to: HBV: Hepatitis B vaccine (3 total doses currently recommended); Polio: Inactivated polio vaccine (4 total doses currently recommended); DTaP: Diphtheria/tetanus/ acellular *Pertussis* (3-in-1 vaccine; 5 total doses currently recommended); Hib: *Haemophilus influenzae* type b conjugate vaccine (4 total doses currently recommended); *Pneumococcus* (Prevnar): Protects against certain forms of *Strep. Pneumoniae* (3 total doses recommended); MMR: measles/ mumps/rubella (3-in-1 vaccine; 2 total doses recommended); Td: Adult tetanus/diphtheria (2-in-1 vaccine; for use in people over age 7). In another embodiment, the glycolipids can be used together with oral polio vaccine.

Cancer

The glycolipids and compositions thereof may be administered to a subject having or at risk of developing cancer. The cancer may be one for which a cancer antigen is known.

Examples of cancer that may be treated according to this disclosure include basal cell carcinoma, biliary tract cancer; bladder cancer; bone cancer; brain cancer; breast cancer; cervical cancer; choriocarcinoma; CNS cancer; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia; acute myeloid leukemia, acute lymphoid leukemia, chronic myeloid leukemia, chronic lymphoid leukemia, liver cancer; small cell lung cancer; non-small cell lung cancer; lymphoma, Hodgkin's lymphoma; Non-Hodgkin's lymphoma; melanoma; myeloma; neuroblastoma; oral cavity cancer; ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; and cancer of the urinary system.

The glycolipids and compositions thereof may be administered with another therapeutic agent or modality such as but not limited to antibody or other biologic, chemotherapy, radiation, surgery and the like. The glycolipids and compositions thereof may be administered with a cancer antigen or a cancer immunotherapy such as an antibody specific for a cancer antigen.

The chemotherapy may be selected from the group consisting of aldesleukin, asparaginase, bleomycin sulfate, carboplatin, chlorambucil, cisplatin, cladribine, cyclophosphamide, cytarabine, dacarbazine, dactinomycin, daunorubicin hydrochloride, docetaxel, doxorubicin, doxorubicin hydrochloride, epirubicin hydrochloride, etoposide, etoposide phosphate, floxuridine, fludarabine, fluorouracil, gemcitabine, gemcitabine hydrochloride, hydroxyurea, idarubicin hydrochloride, ifosfamide, interferons, interferon-α2a, interferon-α2b, interferon-αn3, interferon-α1b, interleukins, irinotecan, mechlorethamine hydrochloride, melphalan, mercatopurine, methotrexate, methotrexate sodium, mitomycin, mitoxantrone, paclitaxel, pegaspargase, pentostatin, prednisone, profimer sodium, procabazine hydrochloride, taxol, taxotere, teniposide, topotecan hydrochloride, vinblastine sulfate, vincristine sulfate or vinorelbine tartrate.

The cancer immunotherapy may include an antibody or antibody fragment specific for a cell surface molecule. Cell surface molecules that may be targeted with the antibody or antibody fragment include but are not limited to HER 2, CD20, CD33, EGF receptor, HLA markers such as HLA-DR, CD52, CD1, CEA, CD22, GD2 ganglioside, FLK2/FLT3, VEGF, VEGFR, and the like.

The antibody or antibody fragment may be specific for a cancer antigen. Cancer antigens that may be targeted with the antibody or antibody fragment include but are not limited to HER 2 (p185), CD20, CD33, GD3 ganglioside, GD2 ganglioside, carcinoembryonic antigen (CEA), CD22, milk mucin core protein, TAG-72, Lewis A antigen, ovarian associated antigens such as OV-TL3 and MOv18, high Mr melanoma antigens recognized by antibody 9.2.27, HMFG-2, SM-3, B72.3, PR5C5, PR4D2, and the like. Other cancer antigens are described in U.S. Pat. No. 5,776,427.

Cancer antigens can be classified in a variety of ways. Cancer antigens include antigens encoded by genes that have undergone chromosomal alteration. Many of these antigens are found in lymphoma and leukemia. Even within this classification, antigens can be characterized as those that involve activation of quiescent genes. These include BCL-1 and IgH (Mantel cell lymphoma), BCL-2 and IgH (Follicular lymphoma), BCL-6 (Diffuse large B-cell lymphoma), TAL-1 and TCRδ or SIL (T-cell acute lymphoblastic leukemia), c-MYC and IgH or IgL (Burkitt lymphoma), MUN/IRF4 and IgH (Myeloma), PAX-5 (BSAP) (Immunocytoma).

Other cancer antigens that involve chromosomal alteration and thereby create a novel fusion gene and/or protein include RARα, PML, PLZF, NPM or NuMA (Acute promyelocytic leukemia), BCR and ABL (Chronic myeloid/acute lymphoblastic leukemia), MLL (HRX) (Acute leukemia), E2A and PBX or HLF (B-cell acute lymphoblastic leukemia), NPM, ALK (Anaplastic large cell leukemia), and NPM, MLF-1 (Myelodysplastic syndrome/acute myeloid leukemia).

Other cancer antigens are specific to a tissue or cell lineage. These include cell surface proteins such as CD20, CD22 (Non-Hodgkin's lymphoma, B-cell lymphoma, chronic lymphocytic leukemia (CLL)), CD52 (B-cell CLL), CD33 (acute myelogenous leukemia (AML)), CD10 (gp100) (common (pre-B) acute lymphocytic leukemia and malignant melanoma), CD3/T-cell receptor (TCR) (T-cell lymphoma and leukemia), CD79/B-cell receptor (BCR) (B-cell lymphoma and leukemia), CD26 (epithelial and lymphoid malignancies), human leukocyte antigen (HLA)-DR, HLA-DP, and HLA-DQ (lymphoid malignancies), RCAS1 (gynecological carcinomas, bilary adenocarcinomas and ductal adenocarcinomas of the pancreas), and prostate specific membrane antigen (prostate cancer).

Tissue- or lineage-specific cancer antigens also include epidermal growth factor receptors (high expression) such as EGFR (HER1 or erbB1) and EGFRvIII (brain, lung, breast, prostate and stomach cancer), erbB2 (HER2 or HER2/neu) (breast cancer and gastric cancer), erbB3 (HER3) (adenocarcinoma), and erbB4 (HER4) (breast cancer).

Tissue- or lineage-specific cancer antigens also include cell-associated proteins such as tyrosinase, melan-A/MART-1, tyrosinase related protein (TRP)-1/gp75 (malignant melanoma), polymorphic epithelial mucin (PEM) (breast tumors), and human epithelial mucin (MUC1) (breast, ovarian, colon and lung cancers).

Tissue- or lineage-specific cancer antigens also include secreted proteins such as monoclonal immunoglobulin (multiple myeloma and plasmacytoma), immunoglobulin light chains (Multiple Myeloma), α-fetoprotein (liver carcinoma), kallikreins 6 and 10 (ovarian cancer), gastrin-releasing peptide/bombesin (lung carcinoma), and prostate specific antigen (prostate cancer).

Still other cancer antigens are cancer testis (CT) antigens that are expressed in some normal tissues such as testis and in some cases placenta. Their expression is common in tumors of diverse lineages and as a group the antigens form targets for immunotherapy. Examples of tumor expression of CT antigens include MAGE-A1, -A3, -A6, -A12, BAGE, GAGE, HAGE, LAGE-1, NY-ESO-1, RAGE, SSX-1, -2, -3, -4, -5, -6, -7, -8, -9, HOM-TES-14/SCP-1, HOM-TES-85 and PRAME. Still other examples of CT antigens and the cancers in which they are expressed include SSX-2, and -4 (Neuroblastoma), SSX-2 (HOM-MEL-40), MAGE, GAGE, BAGE and PRAME (Malignant melanoma), HOM-TES-14/SCP-1 (Meningioma), SSX-4 (Oligodendroglioma), HOM-TES-14/SCP-1, MAGE-3 and SSX-4 (Astrocytoma), SSX member (Head and neck cancer, ovarian cancer, lymphoid tumors, colorectal cancer and breast cancer), RAGE-1, -2, -4, GAGE-1, -2, -3, -4, -5, -6, -7 and -8 (Head and neck squamous cell carcinoma (HNSCC)), HOM-TES14/SCP-1, PRAME, SSX-1 and CT-7 (Non-Hodgkin's lymphoma), and PRAME (Acute lymphoblastic leukemia (ALL), acute myelogenous leukemia (AML) and chronic lymphocytic leukemia (CLL)).

Other cancer antigens are not specific to a particular tissue or cell lineage. These include members of the carcinoembryonic antigen (CEA) family: CD66a, CD66b, CD66c, CD66d and CD66e. These antigens can be expressed in many different malignant tumors and can be targeted by immunotherapy. Still other cancer antigens are viral proteins and these include Human papilloma virus protein (cervical cancer), and EBV-encoded nuclear antigen (EBNA)-1 (lymphomas of the neck and oral cancer). Still other cancer antigens are mutated or aberrantly expressed molecules such as but not limited to CDK4 and beta-catenin (melanoma).

Autoimmune Diseases

Also contemplated are methods of modulating immune responses in a subject by administering to such subject the glycolipid described herein. The subject may be one having or likely to develop an aberrant immune response. The aberrant immune response may be an enhanced immune response and the glycolipid acts to down-regulate the immune response. Enhanced immune responses are typically associated with inflammatory conditions, such as but not limited to autoimmune diseases. Autoimmune diseases, autoimmune disorders and autoimmune conditions are used interchangeably herein.

Accordingly, the compositions comprising glycolipid as a single agent or in combination with an antigen other than lipidated PSA, may be used to modulate (e.g., down-regulate) certain immune responses in subjects having or at risk of developing autoimmune diseases. As will be understood by those of ordinary skill in the art, subjects having autoimmune diseases typically experience one or more "events" or recurrences associated with the autoimmune disease. For example, a subject having inflammatory bowel disease may experience temporally isolated attacks of the disease, characterized by the presence of symptoms or increased severity of symptoms. The invention contemplates that the compositions may be used in such subjects to reduce the likelihood of such future recurrences of the disease or to reduce the severity of symptoms associated with the disease (e.g., pain, fever, discomfort, fatigue, etc.). Thus, the compositions may be administered prior to such recurrence, and in this manner may be chronically administered, optionally at a regular frequency. Examples include once a day, once every 2, 3, 4, 5 or 6 days, or once a week, etc. The invention also contemplates that the compositions may be administered to the subject during a recurrence in order to reduce the severity of symptoms or shorten the time of the recurrence.

Thus, as an example, the invention provides a method comprising administering to a subject at risk of a recurrence of a condition associated with inflammation an effective amount of the glycolipid as a single agent or in combination with an antigen such as or alternative to PSA or lipidated PSA. The method may reduce the likelihood of a recurrence of the condition or may reduce the frequency of future recurrences. The method may reduce the severity of symptoms associated with the condition, whether such symptoms are present in the first manifestation, in a recurrence, or chronically.

Autoimmune diseases are known in the art. Examples of autoimmune diseases include but are not limited to multiple sclerosis, inflammatory bowel disease including Crohn's Disease and ulcerative colitis, rheumatoid arthritis, psoriasis, type I diabetes, uveitis, Celiac disease, pernicious anemia, Srojen's syndrome, Hashimoto's thyroiditis, Graves' disease, systemic lupus erythamatosis, acute disseminated encephalomyelitis, Addison's disease, Ankylosing spondylitis, Antiphospholipid antibody syndrome, Guillain-Barre syndrome, idiopathic thrombocytopenic purpura, Goodpasture's syndrome, Myasthenia gravis, Pemphigus, giant cell arteritis, aplastic anemia, autoimmune hepatitis, Kawaski's disease, mixed connective tissue disease, Ord throiditis, polyarthritis, primary biliary sclerosis, Reiter's syndrome, Takaysu's arteritis, vitiligo, warm autoimmune hemolytic anemia, Wegener's granulomatosis, Chagas' disease, chronic obstructive pulmonary disease, and sarcoidosis.

In important embodiments, the autoimmune disease is multiple sclerosis. In other important embodiments, the autoimmune disease is an inflammatory bowel disease including but not limited to ulcerative colitis and Crohn's disease. In other embodiments, the autoimmune disease may be rheumatoid arthritis or type I diabetes.

In some instances, the compositions of the invention may be administered to a subject who has yet to manifest an autoimmune disease (including symptoms thereof) yet is at risk of developing such as disease based on a known genetic or familial predisposition. Such a subject may have one or more family members that are afflicted with the disease.

In some instances, the compositions of the invention are administered to subject having or at risk of developing graft-versus-host disease. Administration may occur prior to, during and/or after transplantation of an organ or tissue (including blood or a blood product) into the subject.

In still other instances, the compositions may be administered to subjects having or at risk of developing a conditions associated with inflammation.

As an example, the composition may be administered to a subject having asthma. As will be understood in the art, subjects having asthma typically experience asthmatic attacks or events characterized by impaired breathing. The invention contemplates that the compositions described herein may be administered acutely (e.g., a single large dose) or chronically (e.g., repeated, smaller doses) to asthmatic subjects. Accordingly, in some instances, the compositions may be administered prior to an asthmatic attack in order to prevent the occurrence of the attack, reduce the frequency of attacks, and/or to lessen the severity of the attack. In some instances, the compositions may be administered during an attack in order to reduce its severity and/or reduce its duration.

Another condition associated with inflammation is a post-surgical adhesion. The invention contemplates administration of the compositions described herein to subjects having or at risk of developing a post-surgical adhesion. The compositions may be administered prior to, during, and/or immediately following surgery, or any combination thereof including but not limited to prior to and during surgery, in order to prevent the occurrence of such adhesions and/or reduce their severity. The compositions may be administered repeatedly following surgery, including for example every day, every two days, every three days, etc. for a week, two weeks, three weeks, a month, or several months post-surgery.

Another condition associated with inflammation is an abscess, including but not limited to an abdominal abscess as may occur upon leakage of intestinal contents into the peritoneum. In these instances, the subjects being treated may also be administered anti-bacterial agents such as antibiotics.

Thus, as another example, a method is provided that comprises administering to a subject having or at risk of developing an abscess an effective amount of the glycolipid (separate from the polysaccharide component of PSA) or compositions thereof. In some embodiments, the glycolipid is administered prior to development of an abscess and/or prior to the manifestation of symptoms associated with an abscess. In some embodiments, the glycolipid is administered after an abscess has been detected or diagnosed and/or after symptoms associated with an abscess are manifested.

A subject intends any subject that would benefit from administration of a composition of the invention or that could be administered the composition of the invention. In important embodiments, the subject is a human subject. The subject may also be a companion animal such as a dog or cat, agricultural livestock such as horses, cattle, pigs, sheep, etc., laboratory animals such as mice, rats, rabbits, monkeys, etc., or animals such as those maintained in zoos or otherwise in captivity.

A variety of administration routes are available. The particular mode selected will depend, of course, upon the particular condition being treated, the severity of the condition being treated, and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, inhalation (e.g., inhaler or nebulization), or parenteral routes. The term "parenteral" includes subcutaneous, intravenous, intramuscular, intraperitoneal, or infusion.

Formulations

When administered, the agents (e.g., glycolipids) of this disclosure are formulated as pharmaceutically acceptable compositions or preparations. Such compositions or preparations may routinely contain pharmaceutically acceptable carriers, concentrations of salt, buffering agents, preservatives, other immune modulators, and optionally other therapeutic agents. The term "pharmaceutically-acceptable carrier" as used herein, and described more fully below, means one or more compatible solid or liquid filler, diluents or encapsulating substances which are suitable for administration to a human or other animal. The term "carrier" denotes an organic or inorganic ingredient, natural or synthetic, with which the active agent(s) is combined to facilitate administration, long-term storage, stability and the like. The active agents of the present invention may be comingled with the other components of the pharmaceutical compositions, in a manner such that there is no interaction which would substantially impair the desired pharmaceutical efficacy.

The pharmaceutical compositions may be presented in unit dosage form and may be prepared by any of the methods known in the art of pharmacy. All methods include the step of bringing the active agents into association with a carrier which constitutes one or more accessory ingredients. In general, the compositions are prepared by uniformly and intimately bringing the active agent(s) into association with a liquid carrier, a finely divided solid carrier, or both, and then, if necessary, shaping the product. Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion. Solid forms may be coated for example enterically coated.

The active agent(s) may be administered per se (neat) or in the form of a pharmaceutically acceptable salt. Pharmaceutically acceptable salts may be used for in vivo applications as well as in vitro applications. Non-pharmaceutically acceptable salts may be used to prepare pharmaceutically acceptable salts thereof and are not excluded from the scope of the invention. Pharmaceutically acceptable salts include, but are not limited to, those prepared from the following acids: hydrochloric, hydrobromic, sulphuric, nitric, phosphoric, maleic, acetic, salicyclic, p-toluene sulphonic, tartaric, citric, methane sulphonic, formic, malonic, succinic, naphthalene-2-sulphonic, and benzene sulphonic. Also, pharmaceutically acceptable salts can be prepared as alkyline metal or alkyline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Compositions suitable for parenteral administration conveniently comprise a sterile aqueous preparation of the active agent(s), which can be isotonic with the blood of the recipient. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables. Carrier formulations suitable for subcutaneous, intramuscular, intraperitoneal intravenous, etc. administrations may be found in Remington's Pharmaceutical Sciences, Mack Publishing Company, Easton, Pa.

In some embodiments, the glycolipid is formulated with a detergent such as but not limited to Tween or a bile salt such as but not limited to deoxycholate (e.g., sodium deoxycholate) in order to limit or prevent aggregation. Such detergent or bile salt may be used at a low concentration such that it is still pharmaceutically acceptable. For example, it may be present at about or less than 0.0001%. 0.0005%, 0.001%. 0.002%, 0.005%, 0.01%, 0.02%, 0.05%, 0.07%, 0.1%, 0.2%, 0.3%, 0.4%, 0.5%. 0.6%, 0.7%, 0.8%, 0.9%, 1%, 2%, 3%, 4%, 5%, or more.

The pharmaceutical preparations, as described above, are administered in effective amounts. For therapeutic applications, it is generally that amount sufficient to achieve a medically desirable result. In general, a therapeutically effective amount is that amount necessary to delay the onset of, inhibit the progression of, or halt altogether the particular condition being treated, including reducing the likelihood, frequency and/or severity of a recurrence of the condition. As an example, the effective amount may be that amount which serves to reduce, alleviate, or delay the onset of the symptoms (e.g., pain, fever, etc.) of the disorder being treated or prevented. The effective amount will depend upon the mode of administration, the particular condition being treated and the desired outcome. It will also depend upon the stage of the condition, the severity of the condition, the age and physical condition of the subject being treated, the nature of concurrent therapy (if any), the duration of the treatment, the specific route of administration and like factors within the knowledge and expertise of the medical practitioner. For prophylactic applications, it is that amount sufficient to delay the onset of, inhibit the progression of, or halt altogether the particular condition being prevented, and may be measured by the amount required to prevent the onset of symptoms.

Generally, doses of active agent(s) of the present invention may be from about 0.01 mg/kg per day to 1000 mg/kg per day, preferably from about 0.1 mg/kg to 200 mg/kg and most preferably from about 0.2 mg/kg to about 20 mg/kg, in one or more dose administrations daily, for one or more days. It is expected that doses ranging from 1-500 mg/kg, and preferably doses ranging from 1-100 mg/kg, and even more preferably doses ranging from 1-50 mg/kg, will be suitable. The preferred amount can be determined by one of ordinary skill in the art in accordance with standard practice for determining optimum dosage levels of the agent. It is generally preferred that a maximum dose is the highest safe dose according to sound medical judgment be used.

In some instances, the total daily dose for a human subject may range from about 50-100 micrograms of the glycolipid.

The pharmaceutical preparation may be administered alone or in conjunction with one or more other active agents.

The pharmaceutical preparation may be used or administered in conjunction with active agents that are suitable for autoimmune disorders such as multiple sclerosis, Crohn's disease, ulcerative colitis, asthma, rheumatoid arthritis, and the like.

An example of such agents include anti-inflammatory agents. Examples include steroids and corticosteroids such as cortisone; non-steroidal anti-inflammatory drugs such as aspirin, salsalate, celecoxib, diclofenac, etodolac, ibuprofen, indomethacin, ketoprofen, ketorolac, nabumetone, naproxen, oxaprozin, piroxicam, sulindac, and tolmetin; aminosalicylates such as sulfasalazine and 5-aminosalicylates including mesalamine, balsalazide, and olsalazine; azathioprine; mercaptopurine; cyclosporine; beta interferons; glatiramer acetate; dimethyl fumarate; fingolimod; mitoxantrone; disease-modifying antirheumatic drugs (DMARDs) such as methotrexate, leflunomide, hydroxychloroquine and sulfasalazine.

Another example of such agents include antibodies or antibody fragments. Examples include TNF alpha inhibitors such as infliximab (Remicade), adalimumab (Humira), and golimumab (Simponi); natalizumab (Tysabri), vedolizumab (Entyvio); ustekinumab (Stelara); abatacept (Orencia); anakinra (Kineret); certolizumab (Cimzia), etanercept (Enbrel), rituximab (Rituxan), tocilizumab (Actemra), and tofacitinib (Xeljanz).

The invention contemplates that the combined use of glycolipid together with standard treatments such as those recited above will allow a lower dose of the standard treatment to be used for the same or better therapeutic effect, and/or will result in reduced incidence and/or severity of side effects associated with such standard treatments.

In some embodiments, the subject is also administered an anti-bacterial agent such as an antibiotic. In one embodiment the pharmaceutical preparation is formulated or given in conjunction with one or more anti-bacterial agents including antibiotics selected from the group consisting of penicillin G, penicillin V, ampicillin, amoxicillin, bacampicillin, cyclacillin, epicillin, hetacillin, pivampicillin, methicillin, nafcillin, oxacillin, cloxacillin, dicloxacillin, flucloxacillin, carbenicillin, ticarcillin, avlocillin, mezlocillin, piperacillin, amdinocillin, cephalexin, cephradine, cefadoxil, cefaclor, cefazolin, cefuroxime axetil, cefamandole, cefonicid, cefoxitin, cefotaxime, ceftizoxime, cefmnenoxine, ceftriaxone, moxalactam, cefotetan, cefoperazone, ceftazidme, imipenem, clavulanate, timentin, sulbactam, neomycin, erythromycin, metronidazole, chloramphenicol, clindamycin, lincomycin, vancomycin, trimethoprim-sulfamethoxazole, aminoglycosides, quinolones, tetracyclines and rifampin.

The following Examples are included for purposes of illustration and are not intended to limit the scope of the invention.

EXAMPLES

Example 1

Isolation of Glycolipid

Briefly, B. fragilis was grown in anaerobic conditions. The capsular complex from B. fragilis was isolated with hot phenol/water extraction. The polysaccharide fraction was precipitated with ethanol after DNAse, RNase and pronase treatments. The precipitate was subjected to size exclusion chromatography in order to separate polysaccharide constituents. The fractions of interest were analyzed and pooled, then dialyzed and lyophilized. The purity of glycolipid can be assessed by nuclear magnetic resonance spectroscopy and mass spectroscopy.

The isolation and purification process is provided below in greater detail.

The B. fragilis delta44 mutant strain was derived experimentally from strain 9343 and upon further characterization it was found to over-express PSA relative to PSB. Delta44 was plated onto a blood agar plate and grown overnight at 37° C. A swab from a heavily colonized plate was subcultured into a 500 ml starter culture of peptone yeast broth. The starter culture was inoculated into 16 liter culture of the same media and pH was titrated to neutrality with 5M NaOH. An anaerobic gas mix was bubbled into the sealed culture.

After an overnight culture maintained at pH 7, bacteria were checked by Gram stain and subculture. Organisms were collected by centrifugation at 8,000×g for 20 minutes. Bacterial pellets were washed two times with saline yielding approximately one liter of bacterial pellet.

The bacterial pellet was suspended in 68° C. melted crystalline phenol to a final concentration of phenol of about 37% v/v (yielding a phenol/water preparation) and mixed for 30 minutes at 68° C. followed by stirring at 4° C. for 48 hours. The phenol/water preparation was aliquoted into glass bottles which were then centrifuged at 1500 rpm. The upper water layer was harvested. Any residual phenol contained in the harvested aqueous phase was extracted with an equal volume of ethyl ether. The ether phase was then removed using a separatory funnel and any residual ether in the aqueous phase was evaporated, yielding the final aqueous phase from the phenol/water preparation.

The aqueous phase was dialyzed versus water with multiple changes over 5 days at 4° C. and subsequently lyophilized until it was nearly dry (approximately 5 ml water remaining). A solution of 0.05M Tris with magnesium, calcium and sodium azide (total volume 61 ml) was added to the lyophilized product to bring the total volume to about 66 ml.

To the dissolved product was added 10 ml of Tris buffer with DNase (0.07 mg/ml) and RNase (0.33 mg/ml). The entire suspension was filtered through a 0.45 micron filter and the filtrate was stirred at 37° C. The DNase/RNase treatment was repeated by adding fresh enzymes to the mixture, at similar concentrations, and stirred for two hours.

The mixture was then combined with 25 mg pronase in 10 ml Tris/magnesium/calcium solution, and the mixture stirred for 24 hours at 37° C. This step was repeated.

The polysaccharide fraction was precipitated by adding 5 volumes of ethanol at 4° C. to the mixture. The solution was then centrifuged at 12,000×g for 30 minutes to pellet the polysaccharide fraction. The supernatant was removed and the pellet was resuspended in 392 ml type 1 H$_2$O.

The dissolved fraction was then dialyzed against two changes of 16 liters type 1 H$_2$O at 4° C. The volume was reduced by lyophilization to approximately 50 mls. Twenty ml aliquots were chromatographed on a 5×200 cm column of S400 suspended in PBS and 1% sodium deoxycholate, and fractions were collected. Fractions were tested by double diffusion in agar with an antibody that reacts with both lipidated and non-lipidated PSA to determine where lipidated PSA eluted. Aliquots were tested for UV absorption at 280 nm and it was determined that these fractions had no UV absorbable material (e.g., no nucleic acids, no proteins).

Fractions were then pooled, concentrated and dialyzed against type 1 $H_2O$ on a Minitan concentrator (Millipore) with 10,000 mw cutoff membranes until conductivity of 100 ml was less than 50 μS. The final product was then lyophilized.

Polysaccharide and glycolipid purity and structure was determined by proton nuclear magnetic resonance spectroscopy on a 600 MHz spectrometer and mass spectroscopy. For MALDI-TOF-TOF and LC-MS analysis, the sample was resuspended to 10 μg/μL in 2% acetic acid and heated at 90 degrees for 90 minutes. For MALDI-TOF-TOF analysis, samples were mixed 1:1 to 1% matrix (CHCA or DHB) solution and directly loaded to stainless steel MALDI plate. For LC-MS analysis, samples did or did not undergo liquid-liquid extraction (chloroform-water) step, and then were dried and resuspended in 50:50 isopropanol:acetonitrile and injected. The acid treatment in this step results in the cleavage of the oligosaccharide core unit from the acyl-substituted diglucosamine.

An animal model of multiple sclerosis (EAE) may be used to study the immunological activity of glycolipid in vivo. In this model, mice are treated with glycolipid (on the order of about 75-100 μg per mouse) or control (saline, PBS) every three days starting 6 days before EAE induction. Mice are challenged subcutaneously with 250 μg of $MOG_{33-55}$ (Peptides International) in 200 μl of complete Freund's adjuvant (Sigma). On days 0 and 2 after challenge, mice receive intraperitoneal injections of 250 ng of Bordetella pertussis toxin (List Biological Laboratories). Disease is scored on an established 0 to 5 scale, with 5 being advanced neurological disease. Mice are monitored and scored daily for disease progression.

Example 2

Preparation of Lipids for Chemical Analysis

For the experiments shown in FIGS. 9-13, the following procedure was used to prepare glycolipids. Semi-purified B. fragilis glycolipids or overnight-grown bacterial pellet was resuspended in 100 mM acetic acid/sodium acetate buffer (pH 4.5) with 1% sodium dodecylsulfate (SDS) solution at 1-10 mg/mL concentration. The mixture was heated at 95° C. for 30 minutes and cooled. Solution was added with the same volume of chloroform and methanol, shaken well and spun at 1000 g for 10 mins for phase separation. Lower organic phases, containing hydrolyzed GLA, were collected and dried under nitrogen stream and resuspended in 65% isopropanol solution. These samples were injected to reverse-phase HPLC (Phenomenex Kintex C8, 150 mm×4.6 mm×5 um) with the 65-90% gradient of IPA with 10 mM ammonium formate. Fractions were collected, re-analyzed with LC-MS for quantitation and resuspended in DMSO or 0.05% tween-20 PBS solution for in vitro/in vivo experiments.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of enhancing an innate immune response comprising
    (a) administering, to a subject in need of an innate immune response, an effective amount of a glycolipid comprising a tri-acylated, tetra-acylated or penta-acylated diglucosamine conjugated to an oligosaccharide; or
    (b) administering, to a subject in need of an innate immune response, an effective amount of a glycolipid comprising a tri-acylated, tetra-acylated or penta-acylated diglucosamine conjugated to an oligosaccharide, and a lipidated polysaccharide A (PSA) in combination with another therapy,
    wherein the glycolipid is substantially free of LPS; and
    wherein the glycolipid is either
        (a) unphosphorylated; or
        (b) monophosphorylated at the C1 position of the reducing end glucosamine.

2. A method of inducing an immune response to an antigen comprising
    (a) administering, to a subject in need of an antigen-specific immune response, an effective amount of a glycolipid comprising a tri-acylated, tetra-acylated or penta-acylated diglucosamine conjugated to an oligosaccharide and the antigen; or
    (b) administering, to a subject in need of an antigen-specific immune response, an effective amount of a glycolipid comprising a tri-acylated, tetra-acylated or penta-acylated diglucosamine conjugated to an oligosaccharide, the antigen, and lipidated polysaccharide A (PSA),
    wherein the glycolipid is substantially free of LPS; and
    wherein the glycolipid is either
        (a) unphosphorylated; or
        (b) monophosphorylated at the C1 position of the reducing end glucosamine.

3. The method of claim 2, wherein the subject has or is at risk of developing a bacterial infection, a viral infection, a fungal infection, a mycobacterial infection, a parasitic infection or a cancer.

4. The method of claim 1, wherein the subject has or is at risk of developing a bacterial infection, a viral infection, a fungal infection, a mycobacterial infection, a parasitic infection or a cancer.

5. The method of claim 1, wherein the subject has or is at risk of developing a viral infection.

6. The method of claim 1, wherein the tri-acylated, tetra-acylated or penta-acylated diglucosamine comprises acyl chains ranging in length from 14-17 carbons.

7. The method of claim 1, wherein the glycolipid is substantially free of other components found in a B. fragilis capsule, substantially free of polysaccharide, in purified form, in an isolated form, and/or in a lyophilized form.

8. The method of claim 1, wherein the glycolipid is in a micelle form or a liposome form.

9. The method of claim 1, wherein at least one acyl chain is unmodified or modified with a hydroxyl group.

10. The method of claim 1, wherein at least one acyl chain is C16:0-OH, C17:0-OH, C14:0, C15:0, N-substituted or O-substituted.

11. The method of claim 1, wherein the diglucosamine is phosphorylated and/or is conjugated to the oligosaccharide by an acid-labile bond.

12. The method of claim 1, wherein the oligosaccharide comprises galactose and/or glucose and/or fucose residues and/or 1 to 2 KDO residues.

13. The method of claim 1, wherein the glycolipid is administered in a composition further comprising any one selected from the group consisting of:
    (i) a detergent or a bile salt;
    (ii) a non-naturally occurring preservative;
    (iii) a non-naturally occurring stabilizer;
    (iv) human albumin, phenol, glycerin or glycine;
    (v) thimerosal, aluminum hydroxide, benzethonium chloride, formaldehyde, formalin, glutaraldehyde, potassium phosphate, aluminum potassium sulfate, bovine extract, calf serum, ammonium sulfate, aluminum phosphate, non-human cells, Vero (monkey kidney) cells, human cells, MRC-5 (human diploid) cells, and/or MRC-5 cellular proteins;
    (vi) a lipidated polysaccharide A (PSA), wherein the lipidated polysaccharide A (PSA) and the glycolipid are in a 4:1 to 20:1 ratio (w/w);
    (vii) a lipidated polysaccharide A (PSA), wherein there is at least 0.5% (w/w) of the glycolipid;
    (viii) an antigen, and
    (ix) an antigen and a lipidated PSA.

14. The method of claim 13, wherein the detergent or bile salt is present at or less than 1%, 0.5% or 0.1% weight of detergent or bile salt as a percentage of weight of glycolipid.

15. The method of claim 1, wherein the glycolipid is formulated for parenteral administration or oral administration.

16. The method of claim 13, wherein the antigen is a bacterial antigen, attenuated bacteria, a viral antigen, attenuated virus, a fungal antigen, a mycobacterial antigen, a parasitic antigen, a cancer antigen, a human protein or a human polysaccharide.

17. The method of claim 13, wherein the antigen is a viral antigen or an attenuated virus.

18. A method comprising
   (a) administering to a subject in need of immune response modulation a composition comprising a lipidated polysaccharide A (PSA) and a glycolipid comprising a tri-acylated, tetra-acylated or penta-acylated diglucosamine conjugated to an oligosaccharide in an effective amount; or
   (b) administering to a subject in need of immune response modulation an effective amount of a composition comprising a lipidated polysaccharide A (PSA) and a glycolipid comprising a tri-acylated, tetra-acylated or penta-acylated diglucosamine conjugated to an oligosaccharide, in combination with an additional therapy,
   wherein the glycolipid is substantially free of LPS; and wherein the glycolipid is either
      (a) unphosphorylated; or
      (b) monophosphorylated at the C1 position of the reducing end glucosamine.

19. The method of claim 18, wherein the subject in need of immune response modulation is a subject in need of innate immune response modulation, a subject in need of adaptive immune response modulation or a subject in need of immune response stimulation.

\* \* \* \* \*